US011136317B2

(12) United States Patent
Aissaoui et al.

(10) Patent No.: US 11,136,317 B2
(45) Date of Patent: Oct. 5, 2021

(54) NADPH OXIDASE 4 INHIBITORS

(71) Applicant: ACTELION PHARMACEUTICALS LTD, Allschwil (CH)

(72) Inventors: Hamed Aissaoui, Allschwil (CH); Martin Bolli, Allschwil (CH); Christoph Boss, Allschwil (CH); Sylvia Richard-Bildstein, Allschwil (CH); Patrick Sieber, Allschwil (CH)

(73) Assignee: Actelion Pharmaceuticals LTD, Allschwil (CH)

( * ) Notice: Subject to any disclaimer, the term of this patent is extended or adjusted under 35 U.S.C. 154(b) by 0 days.

(21) Appl. No.: 16/777,308

(22) Filed: Jan. 30, 2020

(65) Prior Publication Data
US 2020/0165235 A1 May 28, 2020

Related U.S. Application Data

(63) Continuation of application No. 15/739,083, filed as application No. PCT/IB2016/053672 on Jun. 21, 2016, now Pat. No. 10,584,118.

(30) Foreign Application Priority Data

Jun. 22, 2015 (WO) .................. PCT/IB2015/054662

(51) Int. Cl.
C07D 413/12 (2006.01)
C07D 413/14 (2006.01)
C07D 417/12 (2006.01)
C07D 263/54 (2006.01)
C07D 263/58 (2006.01)
C07D 277/62 (2006.01)
C07D 417/14 (2006.01)
C07D 471/10 (2006.01)
C07D 491/107 (2006.01)
A61P 11/00 (2006.01)
A61P 35/04 (2006.01)

(52) U.S. Cl.
CPC ............ C07D 413/12 (2013.01); A61P 11/00 (2018.01); A61P 35/04 (2018.01); C07D 263/54 (2013.01); C07D 263/58 (2013.01); C07D 277/62 (2013.01); C07D 413/14 (2013.01); C07D 417/12 (2013.01); C07D 417/14 (2013.01); C07D 471/10 (2013.01); C07D 491/107 (2013.01)

(58) Field of Classification Search
CPC .. C07D 277/62; C07D 413/12; C07D 413/14; C07D 417/12; C07D 417/14; C07D 471/10; C07D 491/107; C07D 263/54; C07D 263/58
See application file for complete search history.

(56) References Cited

U.S. PATENT DOCUMENTS

2009/0163464 A1   6/2009   Black et al.

FOREIGN PATENT DOCUMENTS

| CA | 2 669 635 | 5/2008 |
| CN | 101686967 A | 3/2010 |
| CN | 102762563 A | 10/2012 |
| WO | WO 1999/24035 | 5/1999 |
| WO | WO 2001/85722 | 11/2001 |
| WO | WO 2002/079753 | 10/2002 |
| WO | WO 2005/086904 | 9/2005 |
| WO | WO 2006/066173 | 6/2006 |
| WO | WO 2007/025897 | 3/2007 |
| WO | WO 2007/091106 | 8/2007 |
| WO | WO 2007/095124 | 8/2007 |
| WO | WO 2007/110364 | 10/2007 |
| WO | WO 2008/059854 | 5/2008 |
| WO | WO 2008/113856 A1 | 9/2008 |
| WO | WO 2009/085945 | 7/2009 |
| WO | WO 2011/101804 A1 | 8/2011 |
| WO | WO 2011/112602 | 9/2011 |
| WO | WO 2011/159124 | 12/2011 |
| WO | WO 2012/166951 | 12/2012 |
| WO | WO 2013/037499 | 3/2013 |
| WO | WO 2013/068972 | 5/2013 |
| WO | WO 2013/090227 A1 | 6/2013 |

OTHER PUBLICATIONS

Abdala-Valencia et al., "Nonhematopoietic NADPH oxidase regulation of lung eosinophilia and airway hyperresponsiveness in experimentally induced asthma", Am J Physiol Lung Cell Mol Physiol., vol. 292, p. L1111-L1125, (2007).
Ago et al., "Upregulation of Nox4 by Hypertrophic Stimuli Promotes Apoptosis and Mitochondrial Dysfunction in Cardiac Myocytes", Circulation Research, vol. 106, p. 1253-1264. (2010).
Amara et al., "NOX4/NADPH oxidase expression is increased in pulmonary fibroblasts from patients with idiopathic pulmonary fibrosis and mediates TGFb1-induced fibroblast differentiation into myofibroblasts", Thorax, vol. 65, p. 733-738, (2010).
Aoyama et al., "Nicotinamide Adenine Dinucleotide Phosphate Oxidase in Experimental Liver Fibrosis: GKT137831 as a Novel Potential Therapeutic Agent", Hapatology, vol. 56(6), p. 2316-2327, (2012).

(Continued)

Primary Examiner — Susanna Moore
(74) Attorney, Agent, or Firm — Hoxie & Associates LLC

(57) ABSTRACT

The invention relates to 2,5-disubstituted benzoxazole and benzothiazole derivatives of Formula (I)

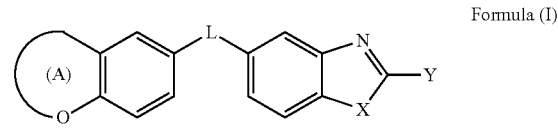

Formula (I)

wherein L, X, Y, and ring (A) are as described in the description, their preparation and their use as pharmaceutically active compounds. Said compounds may be useful for the prevention or treatment of diseases or disorders associated with impaired reactive oxygen species (ROS) production, and/or for the prevention or treatment of various fibrotic diseases.

15 Claims, No Drawings

(56) References Cited

OTHER PUBLICATIONS

Babelova et al., "Role of Nox4 in murine models of kidney disease", Free Radical Biology and Medicine, vol. 53 p. 842-853, (2012).

Barman et al., "NADPH Oxidase 4 Is Expressed in Pulmonary Artery Adventitia and Contributes to Hypertensive Vascular Remodeling", Arterioscler Thromb Vasc Biol., vol. 34, p. 1704-1715, (2014).

Bhandarkar et al., "Fulvene-5 potently inhibits NADPH oxidase 4 and blocks the growth of endothelial tumors in mice", J. Clin. Invest., vol. 119, p. 2359-2365, (2009).

Bauer et al., "Proteomic and Functional Investigation of the Colon Cancer Relapse—Associated Genes NOX4 and ITGA3", Journal of Proteome Research, vol. 13, p. 4910-4918, (2014).

Bedard et al., "The NOX Family of ROS-Generating NADPH Oxidases: Physiology and Pathophysiology", Physiol Rev., vol. 87, p. 245-313, (2007).

Boudreau et al., "Nox4 involvement in TGF-beta and SMAD3-driven induction of the epithelial-to mesenchymal transition and migration of breast epithelial cells", Free Radic Biol Med., vol. 53(7), p. 1489-1499, (2012).

Carnesecchi et al., "A Key Role for NOX4 in Epithelial Cell Death During Development of Lung Fibrosis", Antioxidants & Redox Signaling, vol. 15(3), p. 607-619, (2011).

Chang et al., "Nox4 inhibition enhances the cytoxicity of cisplatin in human renal cancer cells", Journal of Experimental Therapeutis and Oncology, vol. 10, p. 9-18, (2012).

Chen et al., "Regulation of ROS signal transduction by NADPH oxidase 4 localization", J. Cell Biol., vol. 181(7), p. 1129-1139, (2008).

Clempus et al., "Nox4 Is Required for Maintenance of the Differentiated Vascular Smooth Muscle Cell Phenotype", Vascular Biology, vol. 27, p. 42-48, (2007).

Colmenero et al., "Hepatic Expression of Candidate Genes in Patients With Alcoholic Hepatitis: Correlation With Disease Severity", Gastroenterology, vol. 132, p. 687-697, (2007).

Cooney et al., "Cellular and temporal expression of NADPH oxidase (NOX) isotypes after brain injury", Journal of Neuroinflammation, vol. 10, p. 155 (1-13), (2013).

Craige et al., "NADPH Oxidase 4 Promotes Endothelial Angiogenesis Through Endothelial Nitric Oxide Synthase Activation", Circulation, vol. 124, p. 731-740, (2011).

Cucoranu et al., "NAD(P)H Oxidase 4 Mediates Transforming Growth Factor-1—Induced Differentiation of Cardiac Fibroblasts Into Myofibroblasts", Cellular Biology—Circulation Research, vol. 97, p. 900-907, (2005).

Fitzgerald et al., "Nox4 Mediates Renal Cell Carcinoma Cell Invasion through Hypoxia-Induced Interleukin 6- and 8-Production", PLOS One, vol. 7(1), p. e30712, (2012).

Gorin et al., "Targeting NADPH oxidase with a novel dual Nox1/Nox4 inhibitor attenuates renal pathology in type 1 diabetes", Am J Physiol Renal Physiol., vol. 308, p. F1276-F1287, (2015).

Green et al., "The Nox4 Inhibitor GKT137831 Attenuates Hypoxia-Induced Pulmonary Vascular Cell Proliferation", Am J Respir Cell Mol Biol., vol. 47(5), p. 718-726, (2012).

Greene et al., "Protective Groups in Organic Synthesis", P.G.M. Wuts, Wiley-Interscience, (1999).

Hausner et al., "Synthesis of 5- and 6-substituted 2-(4 dimethylaminophenyl)-1, 3-benzoxazoles and their in vitro and in vivo evaluation as imaging agents for amyloid plaque", Bioorganic & Medicinal Chemistry Letters, vol. 19, p. 543-545, (2009).

Hayat et al., "Synthesis and Inhibition Effects on 5-HT6 Receptor of Benzothiazole Derivatives", Bull. Korean Chem. Soc., vol. 34(2), p. 495-499, (2013).

Hecker et al., "NADPH oxidase-4 mediates myofibroblast activation and fibrogenic responses to lung injury", Nature Medicine, vol. 15(9), p. 1077-1081, (2009).

Hecker et al., "Reversal of Persistent fibrosis in aging by targeting Nox4-Nrf2 Redox imbalance", Science Transitional Medicine, vol. 6, p. 1-12 (2014).

Hiraga et al., "Nox4-derived ROS Signaling Contributes to TGF-β-induced Epithelial-mesenchymal Transition in Pancreatic Cancer Cells", Anticancer Research, vol. 33, p. 4431-4438, (2013).

Hsieh et al., "Imaging the Impact of Nox4 in Cycling Hypoxia-mediated U87 Glioblastoma Invasion and Infiltration", Mol Imaging Biol., vol. 14, p. 489-499, (2012).

Hsieh et al., "NADPH Oxidase Subunit 4-Mediated Reactive Oxygen Species Contribute to Cycling Hypoxia-Promoted Tumor Progression in Glioblastoma Multiforme", PLoS One, vol. 6(9), p. e23945, (2011).

Im et al., "Molecular targeting of NOX4 for neuropathic pain after traumatic injury of the spinal cord", Cell Death and Disease, vol. 3, p. e426, (2012).

Infranger et al., "Silencing Nox4 in the Paraventricular Nucleus Improves Myocardial Infarction—Induced Cardiac Dysfunction by Attenuating Sympathoexcitation and Periinfarct Apoptosis", Circulation Research, vol. 106, p. 1763-1774, (2010).

Jarman et al., "An Inhibitor of NADPH Oxidase-4 Attenuates Established Pulmonary Fibrosis in a Rodent Disease Model", American Journal of Respiratory Cell and Molecular Biology, vol. 50(1), p. 158-169, (2013).

Jha et al., "Genetic Targeting or Pharmacologic Inhibition of NADPH Oxidase Nox4 Provides Renoprotection in Long-Term Diabetic Nephropathy", J Am Soc Nephrol., vol. 25, p. 1237-1254, (2014).

Kallenborn-Gerhardt et al., "NADPH Oxidase-4 Maintains Neuropathic Pain after Peripheral Nerve Injury", The Journal of Neuroscience, vol. 32(30), p. 10136-10145, (2012).

Kallenborn-Gerhardt et al., "NOXious signaling in pain processing", Pharmacology & Therapeutics vol. 137, p. 309-317, (2013).

Katz et al., "Benzoxazole derivatives. I. 2-Mercaptobenzoxazoles", J. Org. Chem. vol. 19, p. 758-766, (1954).

Kleinschnitz et al., "Post-Stroke Inhibition of Induced NADPH Oxidase Type 4 Prevents Oxidative Stress and Neurodegeneration", PLoS Biol., vol. 8(9), p. e1000479 (1-13), (2010).

Kuroda et al., "NADPH oxidase 4 (Nox4) is a major source of oxidative stress in the failing heart", PNAS, vol. 107(35), p. 15565-15570, (2010).

Li et al., "Inhibition of Reactive Oxygen Species by Lovastatin Downregulates Vascular Endothelial Growth Factor Expression and Ameliorates Blood-Retinal Barrier Breakdown in db/db Mice", Diabetes, vol. 59, p. 1528-1538, (2010).

Li et al., "NADPH Oxidase 4-Derived H2O2 Promotes Aberrant Retinal Neovascularization via Activation of VEGF Receptor 2 Pathway in Oxygen-Induced Retinopathy", Journal of Diabetes Research, vol. 2015, p. 1-14, (2015).

Li et al., "Reciprocal activation between IL-6/STAT3 and NOX4/Akt signalings promotes proliferation and survival of non-small cell lung cancer cells", Oncotarget, vol. 6(2), p. 1031-1048, (2015).

Li et al., "The NADPH Oxidase NOX4 Drives Cardiac Differentiation: Role in Regulating Cardiac Transcription Factors and MAP Kinase Activation", Molecular Biology of the Cell, vol. 17, p. 3978-3988, (2006).

Maalouf et al., "Nox4-derived reactive oxygen species mediate cardiomyocyte injury in early type 1 diabetes", Am J Physiol Cell Physiol., vol. 302, p. C597-C604, (2012).

Maranchie et al., "Nox4 Is Critical for Hypoxia-Inducible Factor 2-A Transcriptional Activity in von Hippel-Lindau—Deficient Renal Cell Carcinoma", Cancer Res., vol. 65(20), p. 9190-9193, (2005).

Martin et al., "Benzoxazole piperidines as selective and potent somatostatin receptor subtype 5 antagonists", Bioorganic & Medicinal Chemistry Letters, vol. 19, p. 6106-6113, (2009).

Masamune et al., "NADPH oxidase plays a crucial role in the activation of pancreatic stellate cells", Am J Physiol Gastrointest Liver Physiol., vol. 294, p. G99-G108, (2008).

Mittal et al., "Hypoxia-Dependent Regulation of Nonphagocytic NADPH Oxidase Subunit NOX4 in the Pulmonary Vasculature", Circulation Research, vol. 101, p. 258-267, (2007).

Murti et al., "Synthesis and Antimicrobial Screening of Substituted 2-Mercaptobenzothiazole", Journal of Pharmaceutical Research, vol. 7(3), p. 153-15Ö5, (2008).

(56) References Cited

OTHER PUBLICATIONS

Ongarora et al., "Benzoheterocyclic amodiaquine analogues with potent antiplasmodial activity: Synthesis and pharmacological evaluation", Bioorganic & Medicinal Chemistry Letters, vol. 22, p. 5046-5050, (2012).
Peters et al., "TGF-β directs trafficking of the epithelial sodium channel ENaC which has implications for ion and fluid transport in acute lung injury", PNAS, p. E374-E383, (2013).
Piera-Velazquez et al., "Role of Cellular Senescence and NOX4-Mediated Oxidative Stress in Systemic Sclerosis Pathogenesis", Curr Rheumatol Rep., vol. 17, p. 1-11, (2015).
Psathakis et al., "Exhaled markers of oxidative stress in idiopathic pulmonary fibrosis", European Journal of Clinical Investigation, vol. 36, p. 362-367, (2006).
Remington, The Science and Practice of Pharmacy, 21st Edition (2005), Part 5, "Pharmaceutical Manufacturing" [published by Lippincott Williams & Wilkins].
Rynearson et al., "2-Aminobenzoxazole ligands of the hepatitis C virus internal ribosome entry site", Bioorganic & Medicinal Chemistry Letters vol. 24, p. 3521-3525, (2014).
Sampson et al., "ROS Signaling by NOX4 Drives Fibroblast-to-Myofibroblast Differentiation in the Diseased Prostatic Stroma", Mol Endocrinol, vol. 25(3), p. 503-515, (2011).
Sancho et al., "NADPH Oxidase NOX4 Mediates Stellate Cell Activation and Hepatocyte Cell Death during Liver Fibrosis Development", PLoS ONE, vol. 7(9), p. e45285 (1-13), (2012).
Schröder et al., "Nox4 Acts as a Switch Between Differentiation and Proliferation in Preadipocytes", Arterioscler Thromb Vasc Biol., vol. 29, p. 239-245, (2009).
Shimada et al., "ROS generation via NOX4 and its utility in the cytological diagnosis of urothelial carcinoma of the urinary bladder", BMC Urology, vol. 11(22), p. 1-12, (2011).
Shono et al., "Enhanced expression of NADPH oxidase Nox4 in human gliomas and its roles in cell proliferation and survival", Int. J. Cancer, vol. 123, p. 787-792, (2008).
Sobhakumari et al., "NOX4 mediates cytoprotective autophagy induced by the EGFR inhibitor erlotinib in head and neck cancer cells", Toxicol Appl Pharmacol., vol. 272, p. 736-745, (2013).
Stahl et al., "Handbook of Pharmaceutical Salts Properties, Selection, and Use", IUPAC-Wiley-VCH, p. 329-350, (2008).
Sturrock et al., "Nox4 mediates TGF-1-induced retinoblastoma protein phosphorylation, proliferation, and hypertrophy in human airway smooth muscle cells", Am J Physiol Lung Cell Mol Physiol., vol. 292, p. L1543-L1555, (2007).
Thallas-Bonke et al., "Nox-4 deletion reduces oxidative stress and injury by PKC-a-associated mechanisms in diabetic nephropathy", Physiol Rep, vol. 2 (11), p. e12192, (2014).
Tsou et al., "Effect of Oxidative Stress on Protein Tyrosine Phosphatase 1B in Scleroderma Dermal Fibroblasts", Arthritis & Rheumatism, vol. 64(6), p. 1978-1989, (2012).
Vallet et al., "Neuronal Expression of the NADPH Oxidase NOX4, and Its Regulation in Mouse Experimental Brain Ischemia", Neuroscience vol. 132, p. 233-238, (2005).
Waghray et al., "Hydrogen peroxide is a diffusible paracrine signal for the induction of epithelial cell death by activated myofibroblasts", The FASEB Journal, vol. 19(7), p. 854-85, (2005).
Wang et al., "Modeling the mitochondrial cardiomyopathy of Barth syndrome with induced pluripotent stem cell and heart-on-chip technologies", Nature Medicine, vol. 20(6), p. 616-623, (2014).
Weyemi et al., "NADPH oxidase 4 is a critical mediator in Ataxia telangiectasia disease", PNAS, vol. 112(7), p. 2121-2126, (2015).
Wouters et al., "Pharmaceutical Salts and Co-crystals", RSC Drug Discovery, (2012).
Xia et al., "Reactive Oxygen Species Regulate Angiogenesis and Tumor Growth through Vascular Endothelial Growth Factor", Cancer Res., vol. 67(22), p. 10823-10830, (2007).
Yang et al., "Expression of Nox4 in Osteoclasts", Journal of Cellular Biochemistry vol. 92, p. 238-248, (2004).
Zhang et al., "NOX4 promotes non-small cell lung cancer cell proliferation and metastasis through positive feedback regulation of PI3K/Akt signaling", Oncotarget, vol. 5(12), p. 4392-4405, (2014).
Zhao et al., "NADPH Oxidase 4 Induces Cardiac Fibrosis and Hypertrophy Through Activating Akt/mTOR and NFκB Signaling Pathways", Circulation, vol. 131(7), p. 643-655, (2015).
Zhu et al., "A Convenient Synthesis of 2-Mercapto and 2-Chlorobenzothiazoles", J. Heterocyclic Chem., vol. 42, p. 727, (2005).

NADPH OXIDASE 4 INHIBITORS

CROSS REFERENCE TO RELATED APPLICATIONS

This application is a continuation of U.S. patent application Ser. No. 15/739,083, filed on Dec. 21, 2017, which is a United States Application under 35 U.S.C. 371 claiming benefit of PCT Application No. PCT/IB2016/053672, filed on Jun. 21, 2016, which claims the benefit of PCT Application No. PCT/IB2015/054662, filed on Jun. 22, 2015, the contents of each of which are incorporated herein by reference.

The present invention relates to NADPH oxidase 4 inhibitors of Formula (I) and their use as active ingredients in the preparation of pharmaceutical compositions. The invention also concerns related aspects including processes for the preparation of the compounds, pharmaceutical compositions containing a compound of the Formula (I), and their use as compounds treating fibrotic diseases or disorders associated with impaired reactive oxygen species (ROS) production, either alone or in combination with other active compounds or therapies.

ROS are oxygen-derived small molecules that are formed upon incomplete reduction of oxygen and include, besides superoxide anion [$.O_2$—], hydrogen peroxide [$H_2O_2$], hydroxyl —[HO.], -alkoxyl- [RO.], peroxyl- [ROO.], and hydroperoxyl radicals [HOO.]. $.O_2$— can further react with nitric oxide to form peroxynitrite or dismutate, either spontaneously or catalyzed by superoxide dismutase, to $H_2O_2$. $H_2O_2$ is further catalyzed to hypochlorous acid by peroxidase-mediated reaction or to hydroxyl radical by the iron-catalyzed Fenton reaction.

ROS can interact with nucleic acids, proteins, lipids, carbohydrates, but also with other small inorganic molecules. Depending on their nature ROS can modulate a multitude of reversible redox-sensitive signaling pathways, such as those downstream of growth factor receptors. In addition to regulating diverse physiological processes ROS can be toxic to cells since ROS can also irreversibly destroy or alter the function of target molecules and thereby induce oxidative stress.

NADPH oxidases (NOX) are enzymes that transport electrons across cell—and organelle membranes. NADPH-derived electrons are first transported to a bound flavin adenine nucleotide (FAD), which in turn passes electrons sequentially to the two heme groups bound to the transmembrane alpha helices of the NOX proteins and ultimately to oxygen to generate .O2-. The biological function of NOX enzymes is therefore the generation of ROS. Seven members of the NOX family have been identified in humans: NOX1, NOX2, NOX3, NOX4, NOX5, as well as the dual NADPH oxidases/peroxidases Duox1 and Duox2 (Bedard, K., Krause, K. H. The NOX family of ROS-generating NADPH oxidases: physiology and pathophysiology. Physiol Rev (2007), 87(1), 245-313)

NOX4 is ubiquitously expressed in non-phagocytic cells with high expression in the proximal and distal tubules of the kidney. Moderate NOX4 mRNA levels are found in various cell types such as, but not limited to, endothelial cells, smooth muscle cells, fibroblasts, hepatic stellate cells, hepatocytes, hematopoietic stem cells, osteoclasts, keratinocytes, neurons, astrocytes, microglia and in various cancer cells (Babelova, A. et al., Role of NOX4 in murine models of kidney disease. Free Radic Biol Med (2012) 53(4):842-53; Bedard, K., Krause, K. H. Physiol Rev (2007), 87(1), 245-313).

Induction of NOX4 has been linked to the differentiation of mesenchymal cells such as myofibroblasts, adipocytes, smooth muscle cells and cardiac myocytes (Clempus, R. E., et al. NOX4 is required for maintenance of the differentiated vascular smooth muscle cell phenotype. Arterioscler Thromb Vasc Biol 27, 42-48 (2007); Cucoranu, I., et al. NAD(P)H oxidase 4 mediates transforming growth factor-beta1-induced differentiation of cardiac fibroblasts into myofibroblasts. Circ Res 97, 900-907 (2005); Li, J., et al. The NADPH oxidase NOX4 drives cardiac differentiation: Role in regulating cardiac transcription factors and MAP kinase activation. Mol Biol Cell 17, 3978-3988 (2006); Schroder, K. et al. NOX4 acts as a switch between differentiation and proliferation in preadipocytes. Arterioscler Thromb Vasc Biol 29, 239-245 (2009)).

Increased NOX4 activity has been implicated in a number of pathologies including fibrotic diseases and/or diseases or disorders associated with an impaired reactive oxygen species (ROS) production.

Fibrosis involves the synthesis and deposition of extracellular matrix components such as collagens, fibrillins, proteoglycans and adhesion molecules. In fibrotic diseases healthy tissue is lost due to replacement by fibrotic scar tissue. This leads to disruption of tissue architecture and, hence, to compromised organ function. A key event in the onset of fibrotic disease is the differentiation of fibroblast cells into extracellular matrix synthesizing myofibroblasts. This differentiation can be initiated by soluble mediators such as, but not limited to, transforming growth factor-beta1 (TGF-β1). These pro-fibrotic stimuli can trigger resident fibroblasts to produce ROS by either activating or inducing NOX enzymes. These ROS have been shown to amplify the pro-fibrotic signal that results in the differentiation of fibroblasts to myofibroblasts with increased extracellular matrix synthesis, proliferation and survival of these cells (Cucoranu, I., et al. Circ Res 97, 900-907 (2005)).

Diseases in which fibrosis plays a significant pathogenic role include, but are not limited to, pulmonary fibrosis, scleroderma (systemic sclerosis), pancreatic fibrosis, liver fibrosis, diabetic nephropathy, cardiac fibrosis and heart failure.

NOX4 expression is increased in lungs of and in fibroblasts isolated from IPF patients and in rodents subjected to bleomycin-induced lung injury (Amara, N. et al., NOX4/NADPH oxidase expression is increased in pulmonary fibroblasts from patients with idiopathic pulmonary fibrosis and mediates TGFβ1-induced fibroblast differentiation into myofibroblasts. Thorax 65, 733-738 (2010); Hecker, L. et al., NADPH oxidase-4 mediates myofibroblast activation and fibrogenic responses to lung injury. Nat Med 15, 1077-1081 (2009)). Fibroblasts isolated from lungs of patients with idiopathic pulmonary fibrosis (IPF) generate extracellular $H_2O_2$ in response to TGF-β and thereby induce loss of viability and death of co-cultured small airway epithelial cells (Waghray, M. et al., Hydrogen peroxide is a diffusible paracrine signal for the induction of epithelial cell death by activated myofibroblasts. FASEB J 19, 854-856 (2005)). Genetic or pharmacological targeting of NOX4 abrogates fibrogenesis in rodent models of lung injury (Carnesecchi, S. et al., A key role for NOX4 in epithelial cell death during development of lung fibrosis. Antioxid Redox Signal (2011); Hecker, L. et al., Reversal of persistent fibrosis in aging by targeting NOX4-NRF2 redox imbalance. Sci Transl Med 6, 231-247 (2014); Jarman, E. R. et al., An Inhibitor of NADPH Oxidase-4 Attenuates Established Pulmonary Fibrosis in a Rodent Disease Model. Am J Respir Cell Mol Biol, 50(1):158-169 (2013)). Thus, NOX4 plays an important role in lung fibrosis and therapeutic targeting of NOX4 can be an effective strategy for the treatment of fibrotic lung diseases and/or disorders.

Numerous studies have shown increased ROS production by various cells in systemic sclerosis (SSc), as well as elevated ROS levels in plasma from SSc patients (Piera-Velazquez et al., Role of cellular senescence and NOX4-mediated oxidative stress in systemic sclerosis pathogenesis. Curr Rheumatol Rep 17, 473 (2015)). In SSc fibroblasts protein tyrosine phosphatase 1B (PTP1B) activity was significantly reduced while platelet-derived growth factor receptor (PDGFR) phosphorylation was increased (Tsou, P. S. et al., Effect of oxidative stress on protein tyrosine phosphatase 1B in scleroderma dermal fibroblasts. Arthritis Rheum 64, 1978-1989 (2012)). NOX4-mediated oxidation and inactivation of PTP1B serves as a regulatory switch for intracellular tyrosine kinase signaling (Chen, K. et al., Regulation of ROS signal transduction by NADPH oxidase 4 localization. J Cell Biol 181, 1129-1139 (2008)). Thus, NOX4-mediated oxidative inactivation of PTP1B leading to pronounced PDGFR activation may be involved in the pathogenesis of scleroderma providing a rationale for treating SSc patients with a pharmacological NOX4 inhibitor.

Oxidative stress is implicated in pancreatic fibrosis and activated pancreatic stellate cells (PSCs) play an important role in this disease. The activation of PSCs is NOX-dependent and thus, NOX enzymes are potential targets for treatment of pancreatic fibrosis (Masamune, A. et al., NADPH oxidase plays a crucial role in the activation of pancreatic stellate cells. Am J Physiol Gastrointest Liver Physiol 294, G99-G108 (2008)).

Liver fibrosis is the result of chronic liver disease and characterized by activation of hepatic stellate cells (HSCs). NOX4 mediates activation of HSC which are a major source of extracellular matrix components. Hepatic gene expression analysis in patients with alcoholic hepatitis and in patients with hepatitis C virus-derived fibrosis showed strongly elevated NOX4 (Colmenero, J. et al., Hepatic expression of candidate genes in patients with alcoholic hepatitis: correlation with disease severity. Gastroenterology 132, 687-697 (2007)). Increased NOX4 expression was also observed in animal models of liver fibrosis (Sancho, P. et al., NADPH Oxidase NOX4 Mediates Stellate Cell Activation and Hepatocyte Cell Death during Liver Fibrosis Development. PLoS One 7(9), e45285 (2012)). Use of a pharmacological NOX1/4 inhibitor effectively decreased liver fibrosis in two mouse models (Aoyama, T. et al., Nicotinamide adenine dinucleotide phosphate oxidase (NOX) in experimental liver fibrosis: GKT137831 as a novel potential therapeutic agent. Hepatology 56(6):2316-27 (2012)). Targeting NOX4 with a pharmacological inhibitor might thus be beneficial in liver disease associated with fibrosis.

Diabetic nephropathy, or chronic kidney disease, is an associated co-morbidity of diabetes. Diabetic mellitus causes increased ROS formation in the kidney that result in glomerular damage and ultimately leads to renal failure. Pharmacological inhibition and genetic deletion of NOX4 effectively improved the outcome in mouse models of diabetic nephropathy (Jha, J. C. et al., Genetic Targeting or Pharmacologic Inhibition of NADPH Oxidase NOX4 Provides Renoprotection in Long-Term Diabetic Nephropathy. J Am Soc Nephrol 25(6):1237-54 (2014); Thallas-Bonke, V. et al., NOX-4 deletion reduces oxidative stress and injury by PKC-alpha-associated mechanisms in diabetic nephropathy. Physiol Rep 2 2(11). pii: e12192 (2014)) supporting the use of NOX4 inhibitors in diabetic nephropathy.

Diabetic patients have an increased risk of developing cardiomyopathy which ultimately can lead to heart failure. Hyperglycemia can trigger the formation of ROS resulting in myocardial collagen deposition and fibrosis. NOX4-derived ROS of left ventricular origin have been shown to contribute to cardiomyopathy in a rat model for type 1 diabetes (Maalouf, R. M. et al., NOX4-Derived Reactive Oxygen Species Mediate Cardiomyocyte Injury In Early Type 1 Diabetes. Am J Physiol Cell Physiol 302(3):C597-604 (2011)). Prevention of oxidative stress by means of inhibition of NOX4 could thus provide a therapeutic benefit for treatment of diabetic cardiomyopathy.

ROS are increased in the hypertrophic heart and in heart failure patients and the expression of NOX4 is increased in response to hypertrophic stimuli and aging (Ago, T. et al., Upregulation of NOX4 by hypertrophic stimuli promotes apoptosis and mitochondrial dysfunction in cardiac myocytes. Circ Res 106, 1253-1264 (2010)). Upregulation of NOX4 in the myocardium causes remodeling of the heart with increased cardiac fibrosis and hypertrophy (Zhao, Q. D. et al., NADPH Oxidase 4 Induces Cardiac Fibrosis and Hypertrophy Through Activating Akt/mTOR and NFkappaB Signaling Pathways. Circulation 131(7):643-55 (2015)). In response to pressure overload caused by transverse aortic constriction, mice with cardiac-specific deletion of NOX4 gene showed blunted ROS production, attenuated cardiac hypertrophy, better cardiac function and less fibrosis compared with wild-type mice (Kuroda, J. et al., NADPH oxidase 4 (NOX4) is a major source of oxidative stress in the failing heart. Proc Natl Acad Sci USA 107, 15565-15570 (2010)). This supports the idea that treatment of patients suffering from cardiac hypertrophy and cardiac fibrosis progressing towards heart failure might benefit from interventions targeting NOX4.

Impaired reactive oxygen species (ROS) production may be linked to hypertension, asthma, acute respiratory distress syndrome (ARDS), myocardial infarction and heart failure, myopathies such as Barth syndrome, stroke, traumatic brain injury, neuropathic pain, ataxia telangiectasia, ocular diseases, such as diabetic renopathy, and various forms of cancer.

In lungs from patients with idiopathic pulmonary arterial hypertension (IPAH), NOX4 transcript levels were increased (Mittal, M. et al., Hypoxia-dependent regulation of nonphagocytic NADPH oxidase subunit NOX4 in the pulmonary vasculature. Circ Res 101, 258-267 (2007)). NOX4 expression is increased in animal models of PH (Barman, S. A. et al., NADPH Oxidase 4 Is Expressed in Pulmonary Artery Adventitia and Contributes to Hypertensive Vascular Remodeling. Arterioscler Thromb Vasc Biol 34(8):1704-15 (2014)) and pharmacological inhibition of NOX4 attenuates hypoxia-induced vascular remodeling in a mouse model for PH (Green, D. E. et al., The NOX4 Inhibitor, GKT137831, Attenuates Hypoxia-Induced Pulmonary Vascular Cell Proliferation. Am J Respir Cell Mol Biol 47(5):718-26 (2012)). These results support an important role for NOX4 in the vascular remodeling associated with development of pulmonary hypertension.

Infiltration of eosinophils into the lung is one of the hallmarks of asthma. NOX-derived ROS in the endothelium are necessary for eosinophil recruitment during allergic airway inflammation (Abdala-Valencia, H. et al., Nonhematopoietic NADPH oxidase regulation of lung eosinophilia and airway hyperresponsiveness in experimentally induced asthma. Am J Physiol Lung Cell Mol Physiol 292, L1111-1125 (2007)). Asthma is considered an airway obstruction that can be reversed by bronchodilators, but in a number of patients, the condition is characterized by progressive airway remodeling. A pathological feature of this process is enlargement of the bronchial smooth muscle mass, which increases with progression from moderate to severe asthma. NOX4 was shown to promote TGF-β1-induced proliferation and hypertrophy of human airway smooth muscle cells. Therefore, TGF-β1- and NOX4-mediated signaling may play a pivotal pathogenic role in the development of bronchial smooth muscle remodeling in asthma (Sturrock, A. et al., NOX4 mediates TGF-β1-induced retinoblastoma protein phosphorylation, proliferation, and hypertrophy in human airway smooth muscle cells. Am J Physiol Lung Cell Mol Physiol 292, L1543-1555 (2007)).

The acute respiratory distress syndrome (ARDS) is a disease with high mortality, no drug therapy, and poorly understood pathogenesis. The hallmark of ARDS is persistent pulmonary edema. TGF-β levels have been found elevated in lavage fluids of patients with ARDS and TGF-β has been shown to promote lung fluid imbalance in a Bleomycin-induced lung injury model for ADRS. TGF-β effects on lung fluid accumulation has been linked to ROS generated by NOX4 and mice with a genetic deletion of the NOX4 gene were fully protected in this animal model. Thus, NOX4 activity might be targeted in an attempt to normalize alveolar fluid clearance in affected patients (Peters, D. M. et al., TGF-β directs trafficking of the epithelial sodium channel ENaC which has implications for ion and fluid transport in acute lung injury. Proc Natl Acad Sci USA 111(3):E374-83 (2013)).

NOX4 acts as an oxygen sensor and induction of NOX4 in ischemia has been associated with various diseases and/or disorders. Morbidity and mortality associated with acute myocardial infarction (MI) and heart failure are associated with uncontrolled neurohormonal excitation that can lead to cardiovascular deterioration. ROS generated in the paraventricular nucleus (PVN) are causally linked to sympathetic overactivity and declining cardiac function after MI. NOX4 has been identified as the primary source of ROS in the PVN after MI (Infanger, D. W. et al., Silencing NOX4 in the paraventricular nucleus improves myocardial infarction-induced cardiac dysfunction by attenuating sympathoexcitation and periinfarct apoptosis. Circ Res 106, 1763-1774 (2010)). Antioxidant therapies targeted to the hypothalamus may provide a novel strategy for the treatment of MI-induced heart failure.

Barth syndrome (BTHS) is a genetic cardiac and skeletal mitochondrial myopathy. Using induced pluripotent stem cell-derived cardiomyocytes (iPSC-CMs) it has been shown that ROS production was markedly enhanced in these cells. Suppression of excessive ROS in BTHS iPSC-CMs normalized sarcomere organization and contractility of these cells, indicating that prevention of excessive ROS generation might be a target for future therapeutic intervention in myopathies, more specifically in BTHS (Wang, G. et al., Modeling the mitochondrial cardiomyopathy of Barth syndrome with induced pluripotent stem cell and heart-on-chip technologies. Nat Med 20, 616-623 (2014)).

Excessive ROS are suspected to cause tissue damage and neuronal death post stroke. In a model of acute ischemic stroke in which mice are subjected to transient middle cerebral artery occlusion NOX4 has been identified to be a key contributor and a major source of oxidative stress. Deletion of the NOX4-coding gene in mice, as well as inhibiting the ROS-generating activity of NOX with a small molecule inhibitor, reduced brain damage and improved neurological function (Kleinschnitz, C. et al., Post-stroke inhibition of induced NADPH oxidase type 4 prevents oxidative stress and neurodegeneration. PLoS Biol 8(9). pii: e1000479 (2010)). Therefore, NOX4 inhibition is considered a potential treatment for acute stroke.

NOX4 was found to be expressed in neurons, astrocytes, and microglia, and its expression was increased under ischemic conditions. NOX4, may thus contribute to oxidative stress observed acutely after traumatic brain injury and future therapeutic approaches might include NOX4 inhibitors (Cooney, S. J. et al., Cellular and temporal expression of NADPH oxidase (NOX) isotypes after brain injury. J Neuroinflammation 10, 155 (2013); Vallet, P. et al., Neuronal expression of the NADPH oxidase NOX4, and its regulation in mouse experimental brain ischemia. Neuroscience 132, 233-238 (2005)).

In neuropathic pain after nerve injury NOX4-derived ROS essentially contribute to the processing of peripheral nerve dysmyelination and pain hypersensitivity (Im, Y. B. et al., Molecular targeting of NOX4 for neuropathic pain after traumatic injury of the spinal cord. Cell Death Dis 3:e426. (2012); Kallenborn-Gerhardt, W. et al., NADPH oxidase-4 maintains neuropathic pain after peripheral nerve injury. J Neurosci 32, 10136-10145 (2012); Kallenborn-Gerhardt, W. et al., NOXious signaling in pain processing. Pharmacol Ther 137, 309-317 (2013)). WO 2013/037499 A1 discloses the use of inhibitors of NOX4 in the prevention and/or treatment of nerve injury, in particular pain, more particularly neuropathic pain.

Ataxia telangiectasia is a rare, autosomal recessive disorder characterized by progressive cerebellar degeneration. Oxidative stress is one cause of the symptoms of the disease. Elevated levels of NOX4 were found in the cerebellum and in cells derived of Ataxia patients. Inhibition of NOX4 by using genetic and/or pharmacological compounds reduced some of the effects in cellular and in a mouse model for the disease, respectively (Weyemi, U. et al., NADPH oxidase 4 is a critical mediator in Ataxia telangiectasia disease. Proc Natl Acad Sci USA 112(7):2121-6 (2015)).

Bone formation is ongoing even in adulthood and is mediated by osteoblasts, while osteoclast cells absorb bone. NOX4 is upregulated during the differentiation and development of osteoclasts and NOX4-derived ROS can modulate signal transduction pathways necessary for osteoclast function (Yang, S. et al., Expression of NOX4 in osteoclasts. J Cell Biochem 92, 238-248 (2004)). WO 2013/068972 discloses that NOX4 controls bone mass by regulation of osteoclastogenesis. Furthermore, evidence is disclosed showing that NOX4 inhibition is beneficial in the treatment and prevention of osteoporosis and/or an osteoclastogenesis dysfunction.

Oxidative stress plays an important role in vascular endothelial dysfunction in diabetes and diabetic retinopathy is a common complication and one of the most frequent causes of blindness in the U.S. Hallmark sequential pathological changes in diabetic retinopathy include increased vascular permeability, pericyte and endothelial cell death, capillary occlusion and aberrant retinal new vessel growth, or neovascularization. In primary bovine retinal capillary endothelial cells (RCECs) Nox4 expression is significantly higher than Nox2 and Nox1. Exposure of RCECs to hypoxia upregulates Nox4 mRNA and protein expression. In human retinal microvascular endothelial cells (HRECs), overexpression of Nox4 by adenovirus significantly increased extracellular $H_2O_2$ generation, resulting in intensified VEGFR2 activation and exacerbated angiogenesis upon VEGF stimulation (Li, J. et al., Inhibition of reactive oxygen species by Lovastatin downregulates vascular endothelial growth factor expression and ameliorates blood-retinal barrier breakdown in db/db mice: role of NADPH oxidase 4. Diabetes. June; 59(6):1528-38 (2010); Li, J. et al., NADPH oxidase 4-derived $H_2O_2$ promotes aberrante retinal neovascularization via activation of VEGF receptor 2 pathway in oxygen-induced retinopathy. J Diabetes Res. 2015: 963289 (2015))

NOX4 has been identified as a potential target for cancer. Studies have postulated a role for NOX4 in ischemia/hypoxia-induced angiogenesis (Craige, S. M. et al., NADPH Oxidase 4 Promotes Endothelial Angiogenesis Through Endothelial Nitric Oxide Synthase Activation. Circulation 124(6):731-40 (2011)). Angiogenesis is important for tumor development and growth. The hypoxic tissue responds with HIF-1α activation and vascular endothelial growth factor (VEGF) production, which leads to VEGF-induced neovascularization response of the endothelial cells. Ovarian cancer cells showed elevated ROS production and NOX4 knockdown in ovarian cancer cells decreased the levels of VEGF and HIF-1α and tumor angiogenesis (Xia, C. et al., Reactive oxygen species regulate angiogenesis and tumor growth through vascular endothelial growth factor. Cancer Res 67, 10823-10830 (2007)).

Inactivation of the von Hippel-Lindau tumor suppressor (VHL) occurs early in the disease progression of renal cell carcinoma (RCC). Loss of VHL function results in accumulation of the alpha-subunit of the hypoxia-inducible transcription factor (HIF-α). Increased HIF-1α and HIF-2α contribute to the pathogenesis of RCC. Renal NOX4 expression is essential for full HIF-2α expression and activity in renal tumor cells, even in the absence of functional VHL (Maranchie, J. K., Zhan, Y. NOX4 is critical for hypoxia-inducible factor 2-alpha transcriptional activity in von Hippel-Lindau-deficient renal cell carcinoma. Cancer Res 65, 9190-9193 (2005)). NOX4 has been shown to mediate RCC cell invasion though a hypoxia-mediated pathway (Fitzgerald, J. P. et al., NOX4 mediates renal cell carcinoma cell invasion through hypoxia-induced interleukin 6- and 8-production. PLoS One 7(1):e30712 (2012)) and to contribute to RCC chemo-resistance through modulation of pro-apoptotic signaling. This suggests that NOX4 inhibition might be a target in the treatment of RCC and enhance the efficacy of cytotoxic drugs against RCC (Chang, G. et al., NOX4 inhibition enhances the cytotoxicity of cisplatin in human renal cancer cells. J Exp Ther Oncol 10, 9-18 (2012)).

NOX4-generated ROS were required for hypoxia-induced tumor cell invasion and infiltration in glioblastoma (Hsieh, C. H. et al., NADPH oxidase subunit 4-mediated reactive oxygen species contribute to cycling hypoxia-promoted tumor progression in glioblastoma multiforme. PLoS One 6(9):e23945 (2011); Hsieh, C. H. et al., Imaging the Impact of NOX4 in Cycling Hypoxia-mediated U87 Glioblastoma Invasion and Infiltration. Mol Imaging Biol 14, 489-499 (2012); Shono, T. et al., Enhanced expression of NADPH oxidase NOX4 in human gliomas and its roles in cell proliferation and survival. Int J Cancer 123, 787-792 (2008)).

EGFR inhibitors are routinely used in the treatment of head and neck squamous cell carcinoma (HNSCC). However, many HNSCC tumors become refractory to EGFR inhibitors. Activation of autophagy via NOX4-mediated oxidative stress has been identified to reduce the efficacy of chemotherapy in HNSCC cells (Sobhakumari, A. et al., NOX4 mediates cytoprotective autophagy induced by the EGFR inhibitor erlotinib in head and neck cancer cells. Toxicol Appl Pharmacol 272, 736-745 (2013)). Therapies targeted to NOX4 may provide a strategy for the treatment of HNSCC either alone or in combination with EGFR inhibitors.

In pancreatic adenocarcinoma epithelial-mesenchymal transition (EMT) is a prerequisite for tumor invasiveness and metastasis and overexpression of TGF-β is associated with poor prognosis. NOX4 and TGF-β are up-regulated in tumors from pancreatic cancer patients and NOX4-derived ROS have been identified to transmit TGF-β-triggered EMT signals in pancreatic cancer (Hiraga, R. et al., NOX4-derived ROS signaling contributes to TGF-β-induced epithelial-mesenchymal transition in pancreatic cancer cells. Anticancer Res 33, 4431-4438 (2013)).

Furthermore, NOX4 is deregulated in various cancers and involved in cancer proliferation and metastasis and NOX4 has been identified to be highly predictive of relapse in colon cancer (Bauer, K. M. et al., Proteomic and functional investigation of the colon cancer relapse-associated genes NOX4 and ITGA3. J Proteome Res 13, 4910-4918 (2014)).

NOX4 was overexpressed in several urothelial carcinoma cell lines and silencing of NOX4 by siRNA significantly reduced cancer cell growth in an orthotopic mouse model. The data indicate that ROS generation through NOX4 contributes to an early step of urothelial carcinogenesis and cancer cell survival (Shimada, K. et al., ROS generation via NOX4 and its utility in the cytological diagnosis of urothelial carcinoma of the urinary bladder. BMC Urol 11, 22 (2011)). NOX4 may also play a role in stromal remodeling of prostate carcinomas (Sampson, N. et al., ROS signaling by NOX4 drives fibroblast-to-myofibroblast differentiation in the diseased prostate stroma. Mol Endocrinol 25, 503-515 (2011)).

Increased NOX4 was found in breast cancer cell lines as well as in patient tumor samples and NOX4-dependent ROS may be critical for progression of the EMT in breast epithelial cells (Boudreau, H. E. et al., NOX4 involvement in TGF-β and SMAD3-driven induction of the epithelial-to-mesenchymal transition and migration of breast epithelial cells. Free Radic Biol Med 53(7):1489-99 (2012)). NOX4 has been shown to promote malignant progression of non-small cell lung cancer (Li, J. et al., Reciprocal activation between IL-6/STAT3 and NOX4/Akt signalings promotes proliferation and survival of non-small cell lung cancer cells. Oncotarget 6, 1031-1048 (2015); Zhang, C. et al., NOX4 promotes non-small cell lung cancer cell proliferation and metastasis through positive feedback regulation of PI3K/Akt signaling. Oncotarget 5, 4392-4405 (2014)) and inhibitors of NOX4 and NOX2 blocked hemangioma growth in an experimental model of human endothelial cell-derived neoplasms (Bhandarkar, S. S. et al., Fulvene-5 potently inhibits NADPH oxidase 4 and blocks the growth of endothelial tumors in mice. J Clin Invest 119, 2359-2365 (2009)).

Thus, NOX4-derived ROS contribute to various types of cancer and compounds of the present intervention have the potential, either alone or in combination with existing therapy, to show a benefit in the treatment of cancer associated with impaired ROS formation.

More general, ROS originating from NOX4 contribute to the pathogenesis of numerous diseases and/or disorders such as, but not limited to, fibrotic diseases, cardiovascular diseases or disorders, respiratory diseases, pain, bone disorders and cancer. One approach to the treatment of those diseases associated with ROS overproduction by NOX4 is to search for compounds that inhibit NOX4.

Benzoxazole compounds which are inhibitors of Interleukin-6 are known from WO2011/159124. Benzazole compounds as Aurora kinase inhibitors are known from WO2007/095124. Benzoxazole compounds which are MCH receptor antagonists are known from WO2006/066173. Benzoxazole and benzothiazole compounds which are H3 receptor ligands are known from WO2009/085945 and WO2007/110364. Certain 2-aminobenzoxazoles are claimed as combinatorial library compounds in WO2002/079753. Certain benzothiazolecarboxamides are described as tyrosine kinase inhibitors in WO1999/024035. Heterocyclic sulfonamide derivatives which are platelet ADP receptor inhibitors are disclosed in WO2001/085722. Some benzothiazol-6-yl carboxamide compounds are know as commercial library compounds: CAS 930729-55-8, CAS 878583-27-8, CAS 1031064-59-1, CAS 1105223-22-0, CAS 1105223-42-4, CAS 1119368-60-3.

The present invention provides novel 2,5-disubstituted benzoxazole and benzothiazole compounds of Formula (I) that are inhibitors of NADPH oxidase 4 (NOX4). The compounds of the present invention may be useful, alone or in combination with existing drugs, for the prevention or treatment of diseases or disorders associated with impaired ROS production, and/or for the prevention or treatment of various fibrotic diseases.

1) A first embodiment of the invention relates to compounds of the Formula (I):

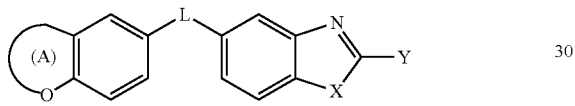

Formula (I)

wherein ring (A) represents a non-aromatic 5- to 7-membered heterocyclic ring which is fused to the phenyl group; wherein said 5- to 7-membered heterocyclic ring contains one oxygen ring atom (at the indicated position, i.e. in para position to the point of attachment of L) and optionally one further ring heteroatom independently selected from oxygen or nitrogen; wherein said 5- to 7-membered heterocyclic ring independently is unsubstituted, or mono-, or di-substituted, wherein the substituents are independently selected from:
  one oxo substituent attached to a ring carbon atom in alpha position to a ring oxygen and/or a ring nitrogen atom (thus forming together with a ring nitrogen an amide group; or, together with a ring oxygen an ester group; or, in case both a ring oxygen and a ring nitrogen atom are adjacent, a carbamate group); and/or
  one $C_{1-3}$-alkyl (especially methyl) attached to a ring nitrogen atom having a free valency; or
  two fluoro substituents attached to the same ring carbon atom;
L represents —NH—CO—* or —CO—NH—*, wherein the asterisks (*) indicate the bond that is linked to the benzoxazole/the benzothiazole moiety;
X represents O or S; and
Y represents
  —$NR^1R^2$ wherein
    $R^1$ represents
      $C_{1-4}$-alkyl (especially methyl, ethyl);
      $C_{2-4}$-alkyl which is mono-substituted with di-($C_{1-3}$-alkyl)amino, hydroxy or $C_{1-3}$-alkoxy;
      $C_{3-5}$-cycloalkyl-$L^1$-, wherein $L^1$ represents a direct bond or $C_{1-3}$-alkylene (especially methylene); and wherein the $C_{3-5}$-cycloalkyl optionally contains one oxygen ring atom, and wherein said $C_{3-5}$-cycloalkyl is unsubstituted, or mono-substituted with methyl or fluoro (especially such group $C_{3-5}$-cycloalkyl-$L^1$-is oxetan-3-yl, oxetan-3-yl-methyl, 3-methyl-oxetan-3-yl, (3-fluoro-oxetan-3-yl)-methyl); or
    a piperidin-3-yl, piperidin-4-yl or pyrrolidin-3-yl group, which groups are substituted on the ring nitrogen atom with $C_{3-5}$-cycloalkyl, wherein said $C_{3-5}$-cycloalkyl optionally contains one oxygen ring atom (especially such group is 1-(oxetan-3-yl)-piperidin-4-yl); and
    $R^2$ represents hydrogen, $C_{1-3}$-alkyl (especially methyl, ethyl), or $C_{3-5}$-cycloalkyl (especially cyclopropyl);
  or Y represents a saturated 4- to 7-membered monocyclic heterocyclyl selected from:
    morpholin-4-yl; 2-oxo-pyrrolidin-1-yl; 1,1-dioxidothiomorpholin-4-yl; or piperazin-1-yl optionally mono-substituted in position 4 with oxetan-3-yl or $C_{1-3}$-alkyl (especially methyl);
    or azetidin-1-yl, pyrrolidin-1-yl, or piperidin-1-yl; wherein said azetidin-1-yl, pyrrolidin-1-yl, or piperidin-1-yl independently is unsubstituted, or substituted with:
      two fluoro substituents attached to the same ring carbon atom; or
      one substituent selected from unsubstituted phenyl, or unsubstituted 5- or 6-membered heteroaryl (especially pyridinyl); or
      one substituent selected from hydroxy; $C_{1-3}$-alkoxy (especially methoxy, isopropoxy); —CO—$C_{1-4}$-alkoxy (especially tert.-butyl-oxy-carbonyl); di-($C_{1-3}$-alkyl)amino (especially dimethylamino); and $C_{1-3}$-alkyl which is mono-substituted with di-($C_{1-3}$-alkyl)amino, hydroxy, or $C_{1-3}$-alkoxy (especially dimethylamino-methyl, 1-hydroxy-1-methyl-ethyl, ethoxy-methyl); or
      two substituents, wherein one of said substituents is $C_{1-4}$-alkyl (especially methyl), and the other is independently selected from hydroxy, or di-($C_{1-3}$-alkyl)amino (especially dimethylamino) (wherein especially said two substituents are attached to the same ring carbon atom of said heterocyclic group); or
      one substituent selected from morpholin-4-yl; 1,1-dioxidothiomorpholin-4-yl; or piperazin-1-yl which is optionally mono-substituted in position 4 with $C_{1-3}$-alkyl (especially methyl);
      one substituent selected from azetidin-1-yl, pyrrolidin-1-yl, or piperidin-1-yl; wherein said groups independently are unsubstituted, or mono-substituted with hydroxy, or di-substituted with methyl and hydroxy (wherein especially both substituents are attached to the same ring carbon atom of said group);
  or Y represents saturated 7- to 11-membered fused, bridged, or spiro-bicyclic heterocyclyl (especially a 7- to 10-membered spiro-bicyclic heterocyclyl) containing at least one nitrogen atom, wherein said nitrogen atom is bound to the benzoxazole/the benzothiazole moiety, and wherein said heterocyclyl optionally contains (especially, in the case that such heterocyclyl is a spiro-bicyclic heterocyclyl, in the distant ring of said spiro-bicyclic heterocyclyl) one further ring heteroatom independently selected from oxygen, nitrogen and sulfur; wherein said heterocyclyl is unsubstituted, or substituted with:

two oxo substituents at a ring sulfur ring atom (thus forming a —SO$_2$— group); or one C$_{1-3}$-alkyl substituent (especially methyl) attached to a ring nitrogen atom having a free valency.

The compounds of formula (I) may contain one or more stereogenic or asymmetric centers, such as one or more asymmetric carbon atoms. The compounds of formula (I) may thus be present as mixtures of stereoisomers or preferably as pure stereoisomers. Mixtures of stereoisomers may be separated in a manner known to a person skilled in the art.

The term "enriched", for example when used in the context of enantiomers is understood in the context of the present invention to mean especially that the respective enantiomer is present in a ratio (mutatis mutandis: purity) of at least 70:30, and notably of at least 90:10 (mutatis mutandis: purity of 70%/90%) with respect to the respective other enantiomer. Preferably the term refers to the respective essentially pure enantiomer. The term "essentially", for example when used in a term such as "essentially pure" is understood in the context of the present invention to mean especially that the respective stereoisomer/composition/compound etc. consists in an amount of at least 90, especially of at least 95, and notably of at least 99 percent by weight of the respective pure stereoisomer/composition/compound etc.

Any reference to a compound of Formula (I) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quéré (Eds.), RSC Publishing, 2012.

In some instances, the compounds of formula (I) may contain tautomeric forms. Such tautomeric forms are encompassed in the scope of the present invention.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

In case one or more substituent(s) are referred to as being optional, such substituent(s) may be absent (i.e. the parent group is unsubstituted and all positions of the parent group having a free valency are substituted with hydrogen), or the parent group is substituted with one or more of such substituent(s), wherein said substituent(s) is/are as explicitly defined.

Where the plural form is used for compounds, salts, pharmaceutical compositions, diseases or the like, this is intended to mean also a single compound, salt, disease or the like.

In this patent application, a bond drawn as a dotted line shows the point of attachment of the radical drawn. For example, the radical drawn below

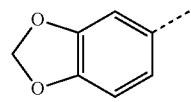

is the benzo[d][1,3]dioxol-5-yl group.

Definitions provided herein are intended to apply uniformly to the compounds of formula (I), as defined in any one of embodiments 1) to 16), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The term "halogen" means fluorine, chlorine, bromine, or iodine; preferably fluorine or chlorine.

The term "alkyl", used alone or in combination, refers to a saturated straight or branched chain hydrocarbon group containing one to six carbon atoms. The term "C$_{x-y}$-alkyl" (x and y each being an integer), refers to an alkyl group as defined before, containing x to y carbon atoms. For example a C$_{1-4}$-alkyl group contains from one to four carbon atoms. Examples of alkyl groups are methyl, ethyl, propyl, isopropyl, butyl, isobutyl, and tert.-butyl. For avoidance of any doubt, in case a group is referred to as e.g. propyl or butyl, it is meant to be n-propyl, respectively n-butyl. Preferred are methyl and ethyl. Most preferred is methyl.

Examples of "C$_{1-3}$-alkyl groups which are mono-substituted with di-(C$_{1-3}$-alkyl)amino, hydroxy, or C$_{1-3}$-alkoxy" are dimethylamino-methyl, 1-hydroxy-1-methyl-ethyl, and ethoxy-methyl.

The term "—C$_{x-y}$-alkylene-", used alone or in combination, refers to bivalently bound alkyl group as defined before containing x to y carbon atoms. Preferably, the points of attachment of a —C$_{1-y}$-alkylene group are in 1,1-diyl, in 1,2-diyl, or in 1,3-diyl arrangement. Preferably, the points of attachment of a —C$_{2-y}$-alkylene group are in 1,2-diyl or in 1,3-diyl arrangement. For the linker L$^1$, an example of a —C$_{1-3}$-alkylene- group is methylene.

The term "alkoxy", used alone or in combination, refers to an alkyl-O— group wherein the alkyl group is as defined before. The term "C$_{x-y}$-alkoxy" (x and y each being an integer) refers to an alkoxy group as defined before containing x to y carbon atoms. For example a C$_{1-4}$-alkoxy group means a group of the formula C$_{1-4}$-alkyl-O— in which the term "C$_{1-4}$-alkyl" has the previously given significance. Examples of alkoxy groups are methoxy, ethoxy, n-propoxy, isopropoxy, n-butoxy, isobutoxy, sec.-butoxy and tert.-butoxy. Preferred are ethoxy and especially methoxy.

The term "fluoroalkyl", used alone or in combination, refers to an alkyl group as defined before containing one to three carbon atoms in which one or more (and possibly all) hydrogen atoms have been replaced with fluorine. The term "$C_{x-y}$-fluoroalkyl" (x and y each being an integer) refers to a fluoroalkyl group as defined before containing x to y carbon atoms. For example a $C_{1-3}$-fluoroalkyl group contains from one to three carbon atoms in which one to seven hydrogen atoms have been replaced with fluorine. Representative examples of fluoroalkyl groups include trifluoromethyl, 2-fluoroethyl, 2,2-difluoroethyl and 2,2,2-trifluoroethyl. Preferred are $C_1$-fluoroalkyl groups such as trifluoromethyl.

The term "fluoroalkoxy", used alone or in combination, refers to an alkoxy group as defined before containing one to three carbon atoms in which one or more (and possibly all) hydrogen atoms have been replaced with fluorine. The term "$C_{x-y}$-fluoroalkoxy" (x and y each being an integer) refers to a fluoroalkoxy group as defined before containing x to y carbon atoms. For example a $C_{1-3}$-fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy. Preferred are $C_1$-fluoroalkoxy groups such as trifluoromethoxy and difluoromethoxy.

The term "cyano" refers to a group —CN.

The term "cycloalkyl", used alone or in combination, refers to a saturated monocyclic hydrocarbon ring containing three to six carbon atoms. The term "$C_{x-y}$-cycloalkyl" (x and y each being an integer), refers to a cycloalkyl group as defined before containing x to y carbon atoms. For example a $C_{3-6}$-cycloalkyl group contains from three to six carbon atoms. Examples of cycloalkyl groups are cyclopropyl, cyclobutyl, cyclopentyl, cyclohexyl, and cycloheptyl. Preferred are cyclopropyl, cyclopentyl and cyclohexyl; especially cyclopropyl.

The term "cycloalkyl optionally containing one ring oxygen atom", used alone or in combination, refers to a cycloalkyl group as defined before. In addition, one ring carbon atom of said cycloalkyl may be replaced by an oxygen atom. Examples of such groups are cycloalkyl groups such as cyclopropyl, cyclobutyl, cyclopentyl, cyclohexyl, and cycloheptyl; as well as oxygen containing groups such as oxetanyl, tetrahydrofuranyl, and tetrahydro-2H-pyranyl. When used for example for the substituent $R^1$ (i.e. said cycloalkyl optionally containing one ring oxygen atom is attached to a nitrogen atom) a ring oxygen atom, if present, is preferably separated from said nitrogen atom by at least two ring carbon atoms. Particular examples of such groups are especially cycloalkyl groups such as cyclopropyl, and cyclobutyl; as well as oxetan-3-yl, and tetrahydrofuran-3-yl. Preferred is oxetan-3-yl. Examples of mono-substituted cycloalkyl optionally containing one ring oxygen atom as used for the group $R^1$ are 3-methyl-oxetan-3-yl, 3-fluoro-oxetan-3-yl.

The term "saturated 4- to 7-membered monocyclic heterocyclyl", used alone or in combination, and if not explicitly defined in a more narrow way, refers to a saturated hydrocarbon ring containing at least one nitrogen atom, wherein said nitrogen atom is bound to the benzoxazole/the benzothiazole moiety, and optionally one further ring heteroatom independently selected from oxygen, nitrogen and sulfur. Such "saturated 4- to 7-membered monocyclic heterocyclyl" is unsubstituted, or substituted as explicitly defined.

Examples of "saturated 4- to 7-membered monocyclic heterocyclyl" groups as used for the substituent Y are:

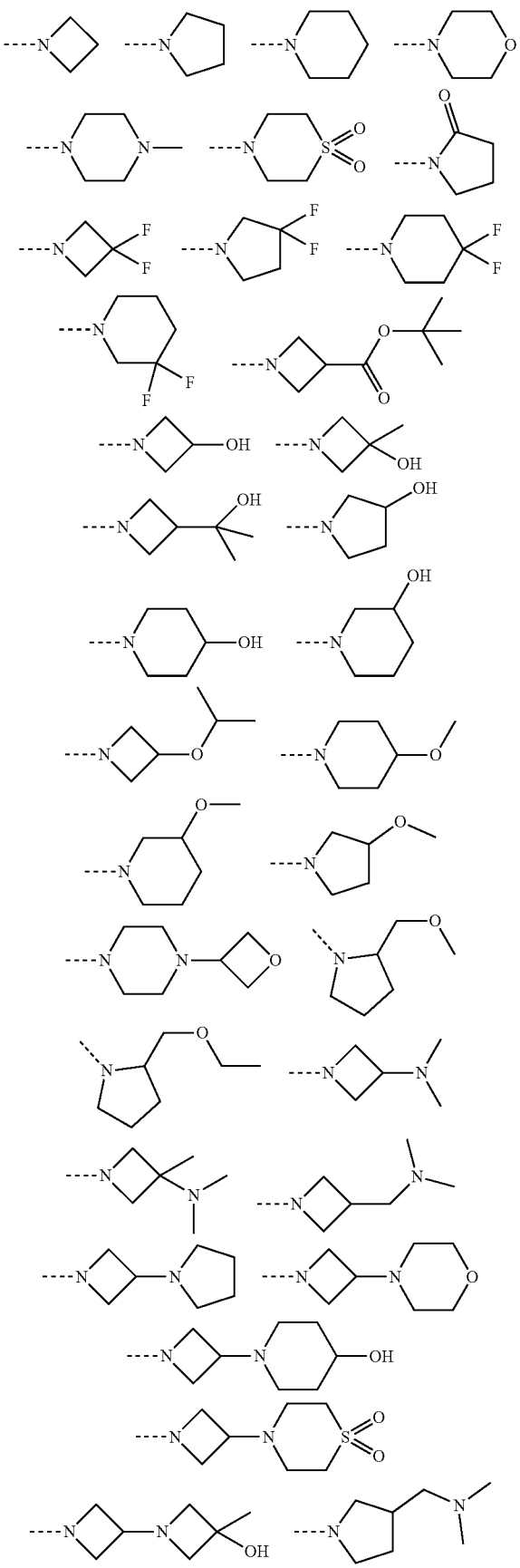

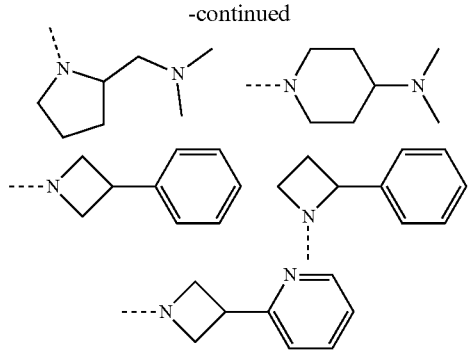
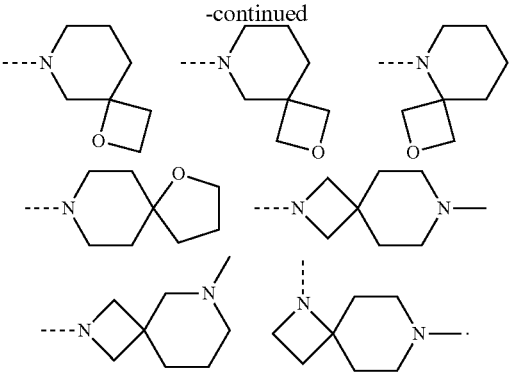

The term "saturated 7- to 11-membered fused, bridged, or spiro-bicyclic heterocyclyl", used alone or in combination, and if not explicitly defined in a more narrow way, refers to a saturated hydrocarbon ring containing at least one nitrogen atom, wherein said nitrogen atom is bound to the benzoxazole/the benzothiazole moiety, and optionally one further ring heteroatom independently selected from oxygen, nitrogen and sulfur. In the case that such "saturated 7- to 11-membered fused, bridged, or spiro-bicyclic heterocyclyl" is a spiro-bicyclic heterocyclyl, optional further ring heteroatom is preferably a ring atom of the distant ring of said spiro-bicyclic heterocyclyl (i.e. the ring which is not bound to the benzoxazole/the benzothiazole moiety). Such "saturated 7- to 11-membered fused, bridged, or spiro-bicyclic heterocyclyl" is unsubstituted, or substituted as explicitly defined.

Examples of "saturated 7- to 11-membered fused, bridged, or spiro-bicyclic heterocyclyl" groups as used for the substituent Y are:

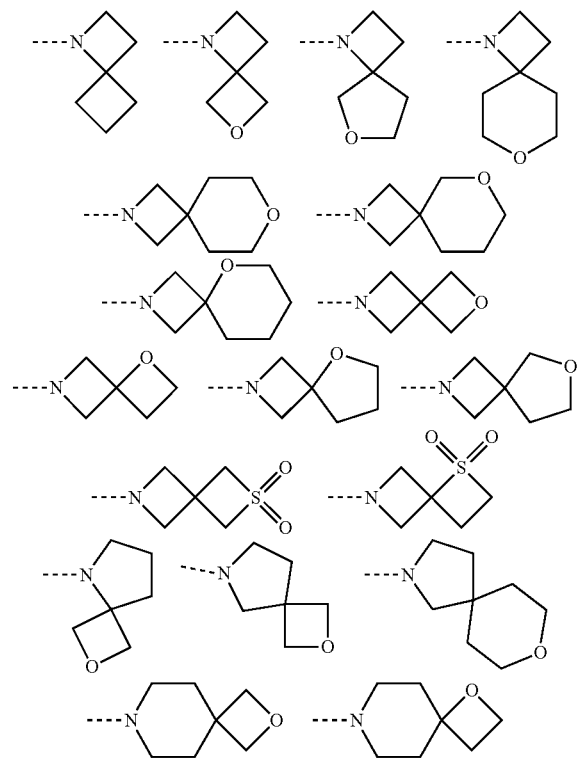

The term "non-aromatic 5- to 7-membered heterocyclic ring which is fused to the phenyl group" as used for ring (A) refers to a saturated 5- to 7-membered heterocyclic ring containing the —C=C— fragment of the phenyl ring to which it is fused, containing one oxygen ring atom at the indicated position, i.e. in para position to the point of attachment of L, and optionally containing one further ring heteroatom independently selected from oxygen or nitrogen. Such 5- to 7-membered ring is unsubstituted or substituted as explicitly defined. In particular, the term refers to a bivalent fragment selected from *—O—CH$_2$—O—, *—O—CH$_2$—CH$_2$—O—, *—O—CH$_2$—CH$_2$—,*—O—CH$_2$—CH$_2$—CH$_2$—, *—O—CH$_2$—NH—, or *—O—CH$_2$—CH$_2$—NH— which fragment is bound to the —C=C— fragment of the phenyl ring to which it is fused, wherein the asterisks indicate the bond which is attached to the carbon atom of the phenyl ring in para position to the group L. Such fragments may be substituted with

- one oxo substituent attached to a carbon atom in alpha position to an oxygen and/or a nitrogen atom (thus forming together with a nitrogen an amide group; or, together with an oxygen an ester group; or, in case both an oxygen and a nitrogen atom are adjacent, a carbamate group); and/or
- one C$_{1-3}$-alkyl (especially methyl) attached to a nitrogen atom having a free valency; or
- two fluoro substituents attached to the same carbon atom.

Particular examples of the fragment

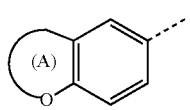

are especially fragments:

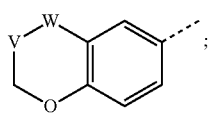

wherein V represents a direct bond or —CH$_2$—; and W represents —CH$_2$—, —O—, or —(NR$^a$)— wherein R$^a$ represents hydrogen or C$_{1-3}$-alkyl (especially R$^a$ represents methyl).

Preferred examples of fragments

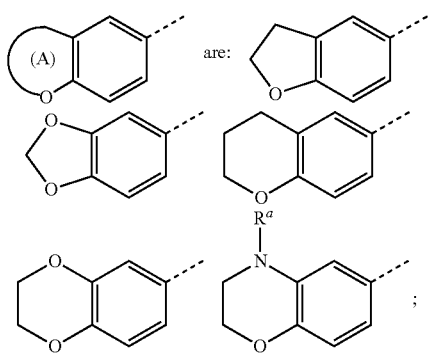

and further examples are:

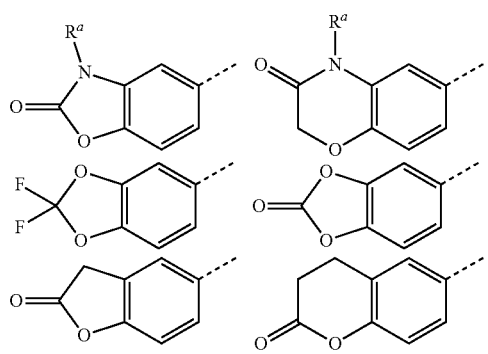

wherein in the groups above $R^a$ independently represents hydrogen or $C_{1-3}$-alkyl (especially $R^a$ represents methyl).

The term "aryl", used alone or in combination, means phenyl or naphthyl, especially phenyl. The above-mentioned aryl groups are unsubstituted or substituted as explicitly defined.

The term "heteroaryl", used alone or in combination, means a 5- to 10-membered monocyclic or bicyclic aromatic ring containing one to a maximum of four heteroatoms, each independently selected from oxygen, nitrogen and sulfur. Examples of such heteroaryl groups are the 5-membered heteroaryl groups furanyl, oxazolyl, isoxazolyl, oxadiazolyl, thiophenyl, thiazolyl, isothiazolyl, thiadiazolyl, pyrrolyl, imidazolyl, pyrazolyl, triazolyl; the 6-membered heteroaryl groups pyridinyl, pyrimidinyl, pyridazinyl, pyrazinyl; and the 8- to 10-membered bicyclic heteroaryl groups indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrrolopyridinyl, pyrazolopyridinyl, pyrazolopyrimidinyl, pyrrolopyrazinyl, imidazopyridinyl, imidazopyridazinyl, and imidazothiazolyl. The above-mentioned heteroaryl groups are unsubstituted or substituted as explicitly defined.

The term "di-($C_{1-3}$-alkyl)amino" refers to a group —N($C_{1-3}$-alkyl)$_2$ wherein the two $C_{1-3}$-alkyl groups are independently selected. An example is dimethylamino.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C. Besides, the term "room temperature" as used herein refers to a temperature of about 25° C.

Further embodiments of the invention are presented hereinafter:

2) A second embodiment of the invention relates to the compounds of formula (I) according to embodiment 1), wherein the fragment

represents a fragment:

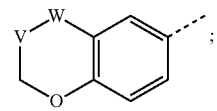

wherein V represents a direct bond or —CH$_2$—; and W represents —CH$_2$—, —O—, or —(NR$^a$)— wherein R$^a$ represents hydrogen or $C_{1-3}$-alkyl (especially R$^a$ represents methyl);

wherein in a preferred sub-embodiment, said fragment is a group selected from:

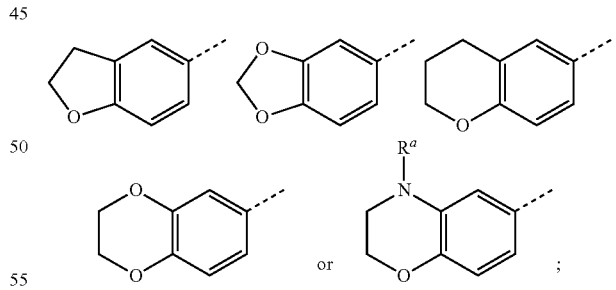

wherein $R^a$ represents hydrogen, or $C_{1-3}$-alkyl (especially $R^a$ represents methyl).

3) A further embodiment relates to compounds according to embodiment 1), wherein the fragment

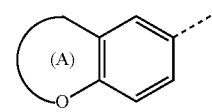

represents

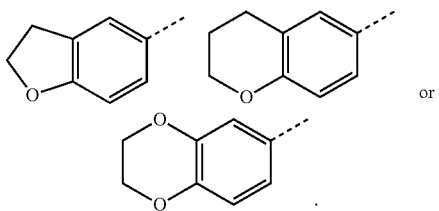

4) A further embodiment relates to compounds according to embodiment 1), wherein the fragment

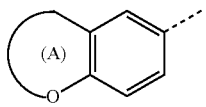

represents

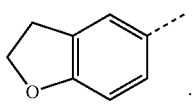

5) A further embodiment relates to compounds according to any one of embodiments 1) to 4), wherein L represents —NH—CO—* wherein the asterisk (*) indicates the bond that is linked to the benzoxazole/the benzothiazole moiety.

6) A further embodiment relates to compounds according to any one of embodiments 1) to 4), wherein L represents —CO—NH—*, wherein the asterisk (*) indicates the bond that is linked to the benzoxazole/the benzothiazole moiety.

7) A further embodiment relates to compounds according to any one of embodiments 1) to 6), wherein X represents O.

8) A further embodiment relates to compounds according to any one of embodiments 1) to 6), wherein X represents S.

9) A further embodiment relates to compounds according to any one of embodiments 1) to 8), wherein Y represents —NR$^1$R$^2$ wherein
R$^1$ represents
  $C_{1-4}$-alkyl (especially methyl, ethyl);
  $C_{2-4}$-alkyl which is mono-substituted with di-($C_{1-3}$-alkyl)amino;
  $C_{3-5}$-cycloalkyl-L$^1$-, wherein L$^1$ represents a direct bond or $C_{1-3}$-alkylene (especially methylene); and wherein the $C_{3-5}$-cycloalkyl optionally contains one oxygen ring atom, and wherein said $C_{3-5}$-cycloalkyl is unsubstituted, or mono-substituted with methyl or fluoro (especially such group $C_{3-5}$-cycloalkyl-L$^1$-is oxetan-3-yl, oxetan-3-yl-methyl, 3-methyl-oxetan-3-yl, (3-fluoro-oxetan-3-yl)-methyl); or
  1-(oxetan-3-yl)-piperidin-4-yl; and
R$^2$ represents hydrogen, $C_{1-3}$-alkyl (especially methyl, ethyl), or $C_{3-5}$-cycloalkyl (especially cyclopropyl);
or Y represents a saturated 4- to 7-membered monocyclic heterocyclyl selected from:
  morpholin-4-yl; 2-oxo-pyrrolidin-1-yl; 1,1-dioxidothiomorpholin-4-yl; or piperazin-1-yl optionally mono-substituted in position 4 with oxetan-3-yl or $C_{1-3}$-alkyl (especially methyl);
or azetidin-1-yl, pyrrolidin-1-yl, or piperidin-1-yl; wherein said azetidin-1-yl, pyrrolidin-1-yl, or piperidin-1-yl independently is unsubstituted, or substituted with:
  two fluoro substituents attached to the same ring carbon atom; or
  one phenyl or pyridinyl substituent, wherein said phenyl or pyridinyl is unsubstituted; or
  one substituent selected from hydroxy; $C_{1-3}$-alkoxy (especially methoxy, isopropoxy); —CO—$C_{1-4}$-alkoxy (especially (tert.-butyl-oxy)-carbonyl); di-($C_{1-3}$-alkyl)amino (especially dimethylamino); and $C_{1-3}$-alkyl which is mono-substituted with di-($C_{1-3}$-alkyl)amino, hydroxy, or $C_{1-3}$-alkoxy (especially dimethylamino-methyl, 1-hydroxy-1-methyl-ethyl, ethoxy-methyl); or
  two substituents, wherein one of said substituents is $C_{1-4}$-alkyl (especially methyl), and the other is independently selected from hydroxy, or di-($C_{1-3}$-alkyl)amino (especially dimethylamino) (wherein especially said two substituents are attached to the same ring carbon atom of said heterocyclic group); or
  one substituent selected from morpholin-4-yl; 1,1-dioxidothiomorpholin-4-yl;
  one substituent selected from azetidin-1-yl, pyrrolidin-1-yl, or piperidin-1-yl; wherein said groups independently are unsubstituted, or mono-substituted with hydroxy, or di-substituted with methyl and hydroxy (wherein especially both substituents are attached to the same ring carbon atom of said group);
or Y represents saturated 7- to 11-membered spiro-bicyclic heterocyclyl (especially a 7- to 10-membered spiro-bicyclic heterocyclyl) containing at least one nitrogen atom, wherein said nitrogen atom is bound to the benzoxazole/the benzothiazole moiety, and wherein said heterocyclyl optionally contains (especially in the distant ring of said spiro-bicyclic heterocyclyl) one further ring heteroatom independently selected from oxygen, nitrogen and sulfur; wherein said heterocyclyl is unsubstituted, or substituted with:
  two oxo substituents at a ring sulfur ring atom (thus forming a —SO$_2$— group); or
  one $C_{1-3}$-alkyl substituent (especially methyl) attached to a ring nitrogen atom having a free valency.

10) A further embodiment relates to compounds according to any one of embodiments 1) to 8), wherein
Y represents a group —NR$^1$R$^2$, wherein
R$^1$ represents
  $C_{1-4}$-alkyl (especially methyl, ethyl);
  $C_{2-4}$-alkyl which is mono-substituted with di-($C_{1-3}$-alkyl)amino;
  $C_{3-5}$-cycloalkyl-L$^1$-, wherein L$^1$ represents a direct bond or $C_{1-3}$-alkylene (especially methylene); and wherein the $C_{3-5}$-cycloalkyl optionally contains one oxygen ring atom, and wherein said $C_{3-5}$-cycloalkyl is unsubstituted, or mono-substituted with methyl or fluoro (especially such group $C_{3-5}$-cycloalkyl-L$^1$-is oxetan-3-yl, oxetan-3-yl-methyl, 3-methyl-oxetan-3-yl, (3-fluoro-oxetan-3-yl)-methyl); or
  1-(oxetan-3-yl)-piperidin-4-yl; and
R$^2$ represents hydrogen, $C_{1-3}$-alkyl (especially methyl, ethyl), or $C_{3-5}$-cycloalkyl (especially cyclopropyl);

or Y represents a group

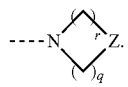

wherein
r and q both represent the integer 2; and
Z represents O, SO$_2$, or NR$^Y$, wherein R$^{Y1}$ represents oxetan-3-yl or C$_{1-3}$-alkyl (especially methyl);
or
r represents the integer 0, 1, 2, or 3; q represents the integer 1, 2, 3, or 4; and the sum of r and q is 2, 3, or 4;
Z represents CH$_2$, CHR$^{Y2}$, or CR$^{Y3}$R$^{Y4}$;
wherein
R$^{Y2}$ represents
unsubstituted phenyl, or unsubstituted 5- or 6-membered heteroaryl (especially unsubstituted phenyl);
hydroxy; C$_{1-3}$-alkoxy (especially methoxy, isopropoxy); —CO—C$_{1-4}$-alkoxy (especially tert.-butyl-oxy-carbonyl); di-(C$_{1-3}$-alkyl)amino (especially dimethylamino); or C$_{1-3}$-alkyl which is mono-substituted with di-(C$_{1-3}$-alkyl)amino, hydroxy, or C$_{1-3}$-alkoxy (especially dimethylamino-methyl, 1-hydroxy-1-methyl-ethyl, ethoxy-methyl);
morpholin-4-yl; 1,1-dioxidothiomorpholin-4-yl; or piperazin-1-yl which is optionally mono-substituted in position 4 with C$_{1-3}$-alkyl (especially methyl); or
azetidin-1-yl, pyrrolidin-1-yl, or piperidin-1-yl; wherein said groups independently are unsubstituted, or mono-substituted with hydroxy, or di-substituted with methyl and hydroxy (wherein especially both substituents are attached to the same ring carbon atom of said group);
and
R$^{Y3}$ represents C$_{1-4}$-alkyl (especially methyl); and R$^{Y4}$ independently represents hydroxy, or di-(C$_{1-3}$-alkyl) amino (especially dimethylamino);
or R$^{Y3}$ and R$^{Y4}$ both represent fluoro;
or R$^{Y3}$ and R$^{Y4}$ together with the carbon atom to which they are attached to form
a 4- to 6-membered saturated carbocyclic ring; or
a 4- to 6-membered saturated heterocyclic ring, wherein said heterocyclic ring contains one ring heteroatom independently selected from oxygen, nitrogen and sulfur; and wherein said heterocyclic ring is unsubstituted, or substituted with:
two oxo substituents at a ring sulfur ring atom (thus forming a —SO$_2$— group); or
one C$_{1-3}$-alkyl substituent (especially methyl) attached to a ring nitrogen atom having a free valency.

11) A further embodiment relates to compounds according to any one of embodiments 1) to 8), wherein Y represents N—(C$_{1-3}$-alkyl)amino, N,N-di-(C$_{1-3}$-alkyl)-amino, N-[2-(di-C$_{1-3}$-alkyl)amino)-ethyl]-N—(C$_{1-3}$-alkyl)-amino, N—(C$_{1-4}$-alkyl)-N-(oxetan-3-yl)-amino, N—(C$_{3-5}$-cycloalkyl)-N-(oxetan-3-yl)-amino, N—(C$_{1-4}$-alkyl)-N-(oxetan-3-yl-methyl)-amino, N-(3-methyl-oxetan-3-yl)-N-methylamino, N-(3-fluoro-oxetan-3-yl-methyl)-N-methylamino, or N-methyl-((N-(oxetan-3-yl)-piperidin)-4-yl)-amino;
or Y represents a saturated 4- to 7-membered monocyclic heterocyclyl selected from:
morpholin-4-yl; 2-oxo-pyrrolidin-1-yl; 1,1-dioxidothiomorpholin-4-yl; or piperazin-1-yl optionally mono-substituted in position 4 with oxetan-3-yl or C$_{1-3}$-alkyl (especially methyl);
or azetidin-1-yl which is unsubstituted, or substituted with:
two fluoro substituents attached to the same ring carbon atom; or
one phenyl or pyridinyl substituent, wherein said phenyl or pyridinyl is unsubstituted; or
one substituent selected from hydroxy; C$_{1-3}$-alkoxy (especially isopropoxy); —CO—C$_{1-4}$-alkoxy (especially (tert.-butyl-oxy)-carbonyl); di-(C$_{1-3}$-alkyl)amino (especially dimethylamino); and C$_{1-3}$-alkyl which is mono-substituted with di-(C$_{1-3}$-alkyl)amino, hydroxy, or C$_{1-3}$-alkoxy (especially dimethylamino-methyl, 1-hydroxy-1-methyl-ethyl, ethoxy-methyl); or
two substituents, wherein one of said substituents is C$_{1-4}$-alkyl (especially methyl), and the other is independently selected from hydroxy, or di-(C$_{1-3}$-alkyl)amino (especially dimethylamino) (wherein especially said two substituents are attached to the same ring carbon atom of said heterocyclic group); or
one substituent selected from morpholin-4-yl; 1,1-dioxidothiomorpholin-4-yl;
one substituent selected from azetidin-1-yl, pyrrolidin-1-yl, or piperidin-1-yl; wherein said groups independently are unsubstituted, or mono-substituted with hydroxy, or di-substituted with methyl and hydroxy (wherein especially both substituents are attached to the same ring carbon atom of said group);
or pyrrolidin-1-yl, or piperidin-1-yl; wherein said pyrrolidin-1-yl, or piperidin-1-yl independently is unsubstituted, or substituted with:
two fluoro substituents attached to the same ring carbon atom; or
one substituent selected from hydroxy; C$_{1-3}$-alkoxy (especially methoxy); di-(C$_{1-3}$-alkyl)amino (especially dimethylamino); and C$_{1-3}$-alkyl which is mono-substituted with di-(C$_{1-3}$-alkyl)amino, or C$_{1-3}$-alkoxy (especially dimethylamino-methyl, ethoxy-methyl);
or Y represents saturated 7- to 11-membered spiro-bicyclic heterocyclyl (especially a 7- to 10-membered spiro-bicyclic heterocyclyl) containing at least one nitrogen atom, wherein said nitrogen atom is bound to the benzoxazole/the benzothiazole moiety, and wherein said heterocyclyl optionally contains (especially in the distant ring of said spiro-bicyclic heterocyclyl) one further ring heteroatom independently selected from oxygen, nitrogen and sulfur; wherein said heterocyclyl is unsubstituted, or substituted with:
two oxo substituents at a ring sulfur ring atom (thus forming a —SO$_2$— group); or
one C$_{1-3}$-alkyl substituent (especially methyl) attached to a ring nitrogen atom having a free valency.

12) A further embodiment relates to compounds according to any one of embodiments 1) to 8), wherein Y represents saturated 4- to 7-membered monocyclic heterocyclyl selected from:
morpholin-4-yl; 2-oxo-pyrrolidin-1-yl; 1,1-dioxodothiomorpholin-4-yl; or piperazin-1-yl optionally mono-substituted in position 4 with oxetan-3-yl or $C_{1-3}$-alkyl (especially methyl);
or azetidin-1-yl which is unsubstituted, or substituted with:
two fluoro substituents attached to the same ring carbon atom; or
one phenyl substituent, wherein said phenyl is unsubstituted; or
one substituent selected from hydroxy; $C_{1-3}$-alkoxy (especially isopropoxy); —CO—$C_{1-4}$-alkoxy (especially (tert.-butyl-oxy)-carbonyl); di-($C_{1-3}$-alkyl)amino (especially dimethylamino); and $C_{1-3}$-alkyl which is mono-substituted with di-($C_{1-3}$-alkyl)amino, hydroxy, or $C_{1-3}$-alkoxy (especially dimethylamino-methyl, 1-hydroxy-1-methyl-ethyl, ethoxy-methyl); or
two substituents, wherein one of said substituents is $C_{1-4}$-alkyl (especially methyl), and the other is independently selected from hydroxy, or di-($C_{1-3}$-alkyl)amino (especially dimethylamino) (wherein especially said two substituents are attached to the same ring carbon atom of said heterocyclic group); or
one substituent selected from morpholin-4-yl; 1,1-dioxidothiomorpholin-4-yl;
one substituent selected from azetidin-1-yl, pyrrolidin-1-yl, or piperidin-1-yl; wherein said groups independently are unsubstituted, or mono-substituted with hydroxy, or di-substituted with methyl and hydroxy (wherein especially both substituents are attached to the same ring carbon atom of said group);
or pyrrolidin-1-yl, or piperidin-1-yl; wherein said pyrrolidin-1-yl, or piperidin-1-yl independently is unsubstituted, or substituted with:
two fluoro substituents attached to the same ring carbon atom; or
one substituent selected from hydroxy; $C_{1-3}$-alkoxy (especially methoxy); di-($C_{1-3}$-alkyl)amino (especially dimethylamino); and $C_{1-3}$-alkyl which is mono-substituted with di-($C_{1-3}$-alkyl)amino, or $C_{1-3}$-alkoxy (especially dimethylamino-methyl, ethoxy-methyl);
or Y represents saturated 7- to 11-membered spiro-bicyclic heterocyclyl (especially a 7- to 10-membered spiro-bicyclic heterocyclyl) containing at least one nitrogen atom, wherein said nitrogen atom is bound to the benzoxazole/the benzothiazole moiety, and wherein said heterocyclyl optionally contains (especially in the distant ring of said spiro-bicyclic heterocyclyl) one further ring heteroatom independently selected from oxygen, nitrogen and sulfur; wherein said heterocyclyl is unsubstituted, or substituted with:
two oxo substituents at a ring sulfur ring atom (thus forming a —SO$_2$— group); or
one $C_{1-3}$-alkyl substituent (especially methyl) attached to a ring nitrogen atom having a free valency.

13) A further embodiment relates to compounds according to any one of embodiments 1) to 8), wherein Y represents a group independently selected from the following groups A), B), C), D), or E):

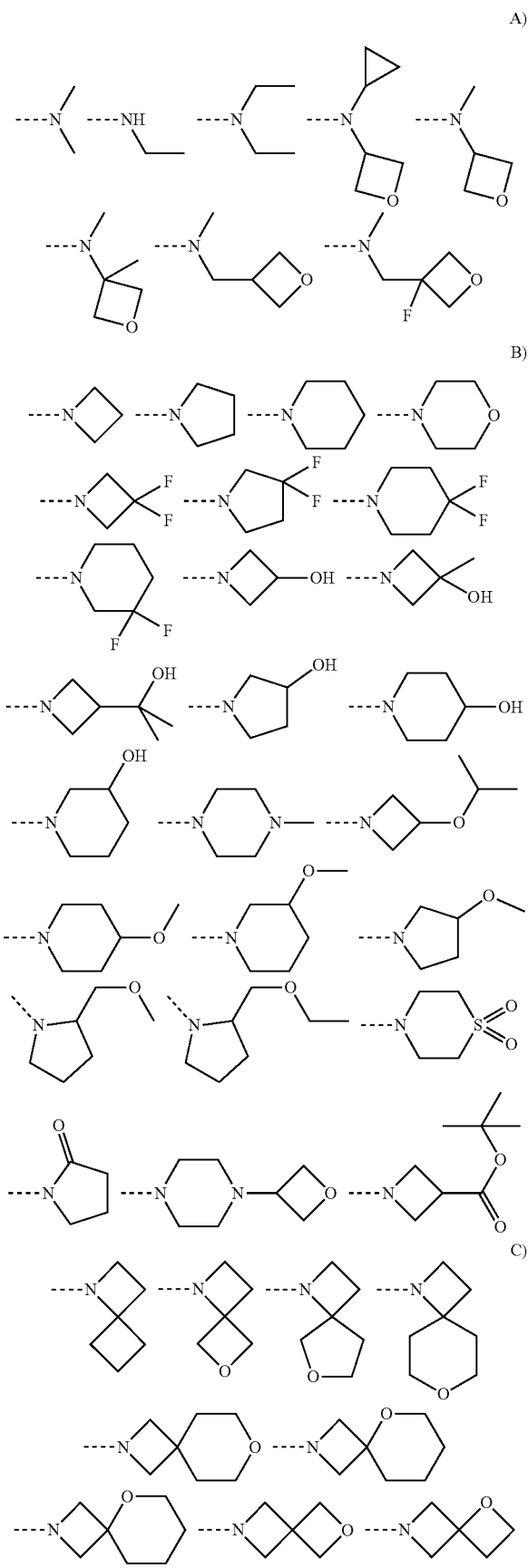

-continued
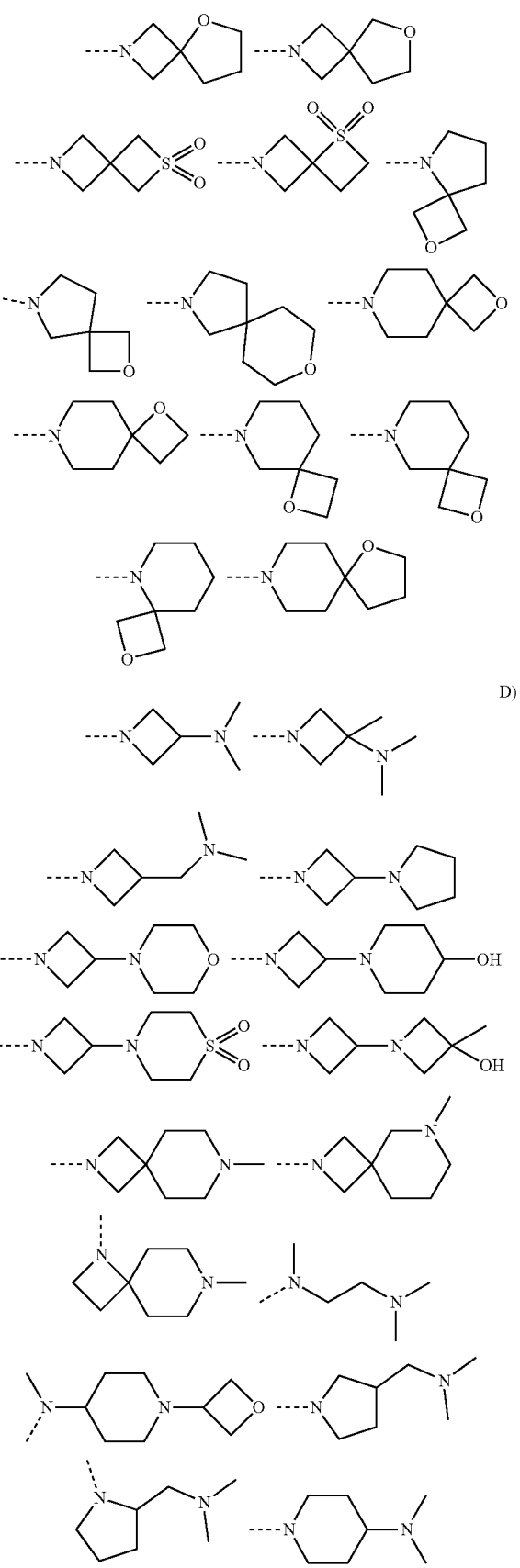
-continued
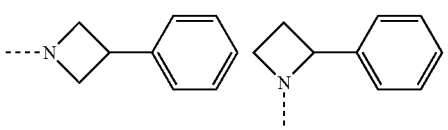
E)
14) A further embodiment relates to compounds according to any one of embodiments 1) to 8), wherein Y represents a group independently selected from the following groups A), B), C), or D):
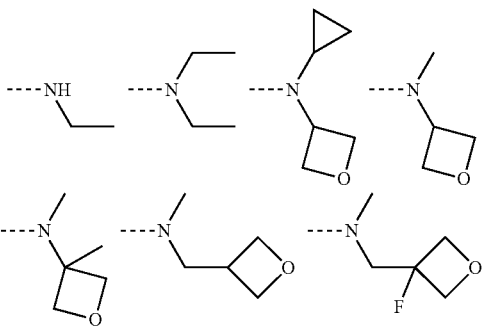
A)
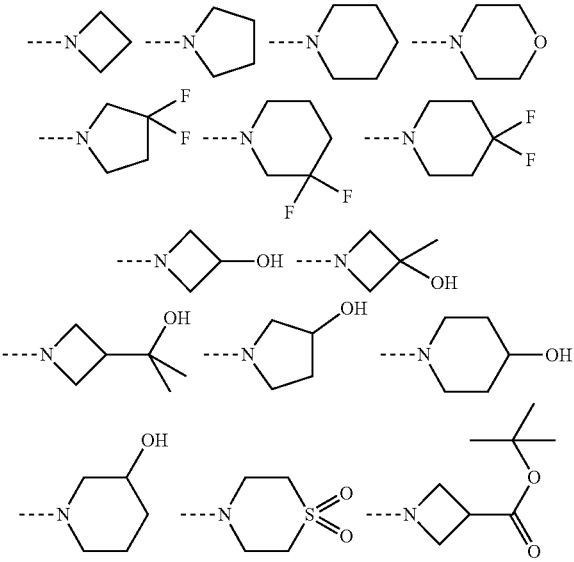
B)
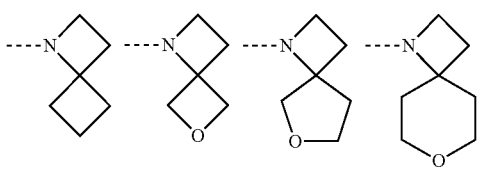
C)

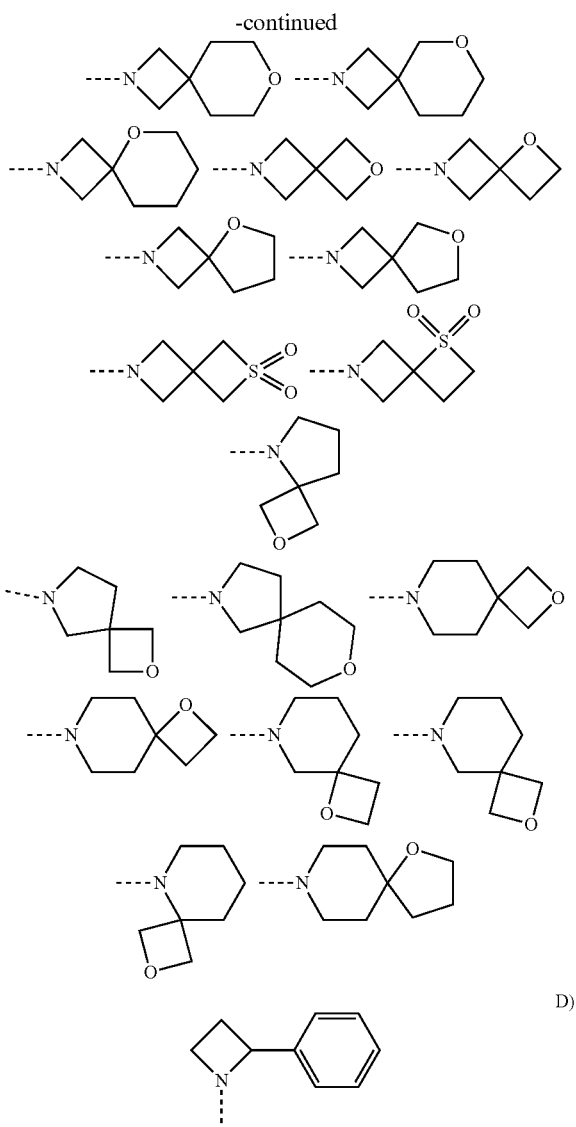

15) A further embodiment relates to compounds according to any one of embodiments 1) to 8), wherein Y represents a group independently selected from the following groups A) or B):

A)

B)

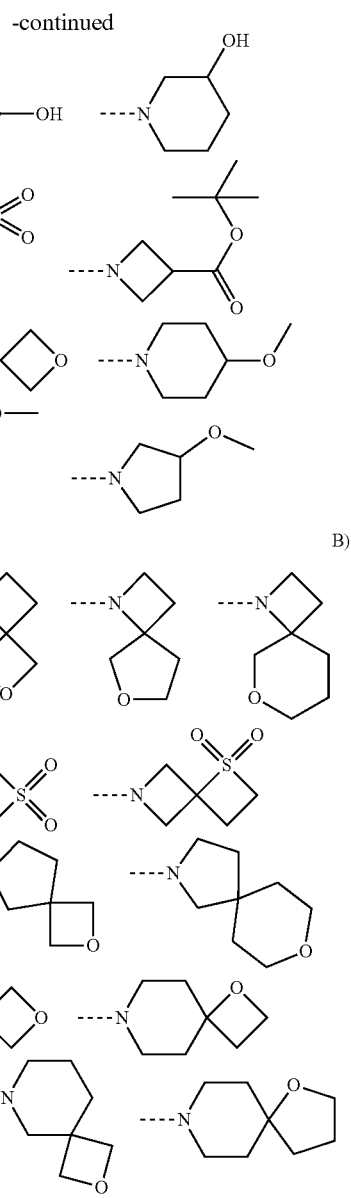

D)

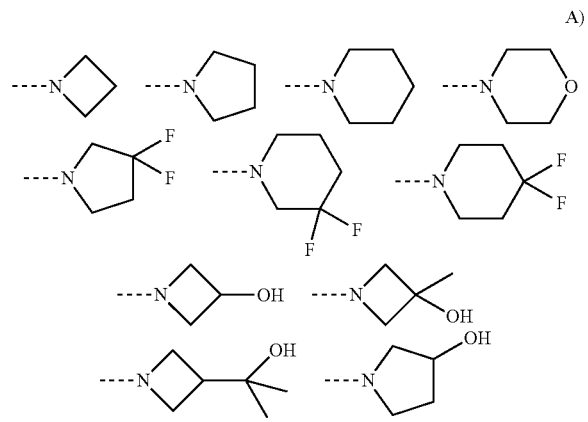

16) The invention, thus, relates to compounds of the formula (I) as defined in embodiment 1), or to such compounds further limited by the characteristics of any one of embodiments 2) to 14), under consideration of their respective dependencies; to pharmaceutically acceptable salts thereof; and to the use of such compounds as medicaments, especially for the prevention or treatment of diseases or disorders associated with impaired ROS production, and/or for the prevention or treatment of various fibrotic diseases. Especially the following embodiments relating to the compounds of formula (I) are thus possible and intended and herewith specifically disclosed in individualized form:

1, 2+1, 3+1, 4+1, 5+1, 5+2+1, 5+3+1, 5+4+1, 6+1, 6+2+1, 6+3+1, 6+4+1, 7+1, 7+2+1, 7+3+1, 7+4+1, 7+5+1, 7+5+2+1, 7+5+3+1, 7+5+4+1, 7+6+1, 7+6+2+1, 7+6+3+1, 7+6+4+1, 8+1, 8+2+1, 8+3+1, 8+4+1, 8+5+1, 8+5+2+1, 8+5+3+1, 8+5+4+1, 8+6+1, 8+6+2+1, 8+6+3+1, 8+6+4+1, 9+1, 9+2+1, 9+3+1, 9+4+1, 9+5+1, 9+5+2+1, 9+5+3+1, 9+5+4+1, 9+6+1, 9+6+2+1, 9+6+3+1, 9+6+4+1, 9+7+1, 9+7+2+1, 9+7+3+1, 9+7+4+1, 9+7+5+1, 9+7+5+2+1, 9+7+5+3+1,

9+7+5+4+1, 9+7+6+1, 9+7+6+2+1, 9+7+6+3+1, 9+7+6+4+1, 9+8+1, 9+8+2+1, 9+8+3+1, 9+8+4+1, 9+8+5+1, 9+8+5+2+1, 9+8+5+3+1, 9+8+5+4+1, 9+8+6+1, 9+8+6+2+1, 9+8+6+3+1, 9+8+6+4+1, 10+1, 10+2+1, 10+3+1, 10+4+1, 10+5+1, 10+5+2+1, 10+5+3+1, 10+5+4+1, 10+6+1, 10+6+2+1, 10+6+3+1, 10+6+4+1, 10+7+1, 10+7+2+1, 10+7+3+1, 10+7+4+1, 10+7+5+1, 10+7+5+2+1, 10+7+5+3+1, 10+7+5+4+1, 10+7+6+1, 10+7+6+2+1, 10+7+6+3+1, 10+7+6+4+1, 10+8+1, 10+8+2+1, 10+8+3+1, 10+8+4+1, 10+8+5+1, 10+8+5+2+1, 10+8+5+3+1, 10+8+5+4+1, 10+8+6+1, 10+8+6+2+1, 10+8+6+3+1, 10+8+6+4+1, 11+1, 11+2+1, 11+3+1, 11+4+1, 11+5+1, 11+5+2+1, 11+5+3+1, 11+5+4+1, 11+6+1, 11+6+2+1, 11+6+3+1, 11+6+4+1, 11+7+1, 11+7+2+1, 11+7+3+1, 11+7+4+1, 11+7+5+1, 11+7+5+2+1, 11+7+5+3+1, 11+7+5+4+1, 11+7+6+1, 11+7+6+2+1, 11+7+6+3+1, 11+7+6+4+1, 11+8+1, 11+8+2+1, 11+8+3+1, 11+8+4+1, 11+8+5+1, 11+8+5+2+1, 11+8+5+3+1, 11+8+5+4+1, 11+8+6+1, 11+8+6+2+1, 11+8+6+3+1, 11+8+6+4+1, 12+1, 12+2+1, 12+3+1, 12+4+1, 12+5+1, 12+5+2+1, 12+5+3+1, 12+5+4+1, 12+6+1, 12+6+2+1, 12+6+3+1, 12+6+4+1, 12+7+1, 12+7+2+1, 12+7+3+1, 12+7+4+1, 12+7+5+1, 12+7+5+2+1, 12+7+5+3+1, 12+7+5+4+1, 12+7+6+1, 12+7+6+2+1, 12+7+6+3+1, 12+7+6+4+1, 12+8+1, 12+8+2+1, 12+8+3+1, 12+8+4+1, 12+8+5+1, 12+8+5+2+1, 12+8+5+3+1, 12+8+5+4+1, 12+8+6+1, 12+8+6+2+1, 12+8+6+3+1, 12+8+6+4+1, 13+1, 13+2+1, 13+3+1, 13+4+1, 13+5+1, 13+5+2+1, 13+5+3+1, 13+5+4+1, 13+6+1, 13+6+2+1, 13+6+3+1, 13+6+4+1, 13+7+1, 13+7+2+1, 13+7+3+1, 13+7+4+1, 13+7+5+1, 13+7+5+2+1, 13+7+5+3+1, 13+7+5+4+1, 13+7+6+1, 13+7+6+2+1, 13+7+6+3+1, 13+7+6+4+1, 13+8+1, 13+8+2+1, 13+8+3+1, 13+8+4+1, 13+8+5+1, 13+8+5+2+1, 13+8+5+3+1, 13+8+5+4+1, 13+8+6+1, 13+8+6+2+1, 13+8+6+3+1, 13+8+6+4+1, 14+1, 14+2+1, 14+3+1, 14+4+1, 14+5+1, 14+5+2+1, 14+5+3+1, 14+5+4+1, 14+6+1, 14+6+2+1, 14+6+3+1, 14+6+4+1, 14+7+1, 14+7+2+1, 14+7+3+1, 14+7+4+1, 14+7+5+1, 14+7+5+2+1, 14+7+5+3+1, 14+7+5+4+1, 14+7+6+1, 14+7+6+2+1, 14+7+6+3+1, 14+7+6+4+1, 14+8+1, 14+8+2+1, 14+8+3+1, 14+8+4+1, 14+8+5+1, 14+8+5+2+1, 14+8+5+3+1, 14+8+5+4+1, 14+8+6+1, 14+8+6+2+1, 14+8+6+3+1, 14+8+6+4+1, 15+1, 15+2+1, 15+3+1, 15+4+1, 15+5+1, 15+5+2+1, 15+5+3+1, 15+5+4+1, 15+6+1, 15+6+2+1, 15+6+3+1, 15+6+4+1, 15+7+1, 15+7+2+1, 15+7+3+1, 15+7+4+1, 15+7+5+1, 15+7+5+2+1, 15+7+5+3+1, 15+7+5+4+1, 15+7+6+1, 15+7+6+2+1, 15+7+6+3+1, 15+7+6+4+1, 15+8+1, 15+8+2+1, 15+8+3+1, 15+8+4+1, 15+8+5+1, 15+8+5+2+1, 15+8+5+3+1, 15+8+5+4+1, 15+8+6+1, 15+8+6+2+1, 15+8+6+3+1, 15+8+6+4+1.

In the list above, the numbers refer to the embodiments according to their numbering provided hereinabove whereas "+" indicates the dependency from another embodiment. The different individualized embodiments are separated by commas. In other words, "14+8+1" for example refers to embodiment 14) depending on embodiment 8), depending on embodiment 1), i.e. embodiment "14+8+1" corresponds to the compounds of embodiment 1) further limited by the features of the embodiments 8) and 14).

17) A further embodiment relates to compounds of Formula (I) according to embodiment 1) which are selected from the following compounds:

2,3-Dihydro-benzofuran-5-carboxylic acid [2-(1,1-dioxo-1l6-thiomorpholin-4-yl)-benzooxazol-5-yl]-amide;
2,3-Dihydro-benzofuran-5-carboxylic acid (2-piperidin-1-yl-benzooxazol-5-yl)-amide;
2,3-Dihydro-benzofuran-5-carboxylic acid (2-pyrrolidin-1-yl-benzooxazol-5-yl)-amide;
2,3-Dihydro-benzofuran-5-carboxylic acid [2-(4-methyl-piperazin-1-yl)-benzooxazol-5-yl]-amide;
2,3-Dihydro-benzofuran-5-carboxylic acid (2-morpholin-4-yl-benzooxazol-5-yl)-amide;
2,3-Dihydro-benzofuran-5-carboxylic acid (2-diethylamino-benzooxazol-5-yl)-amide;
2,3-Dihydro-benzofuran-5-carboxylic acid [2-(4,4-difluoro-piperidin-1-yl)-benzooxazol-5-yl]-amide;
2,3-Dihydro-benzofuran-5-carboxylic acid [2-(3,3-difluoro-azetidin-1-yl)-benzooxazol-5-yl]-amide;
2,3-Dihydro-benzofuran-5-carboxylic acid [2-(3,3-difluoro-pyrrolidin-1-yl)-benzooxazol-5-yl]-amide;
2,3-Dihydro-benzofuran-5-carboxylic acid [2-(3-methoxy-pyrrolidin-1-yl)-benzooxazol-5-yl]-amide;
2,3-Dihydro-benzofuran-5-carboxylic acid [2-(4-methoxy-piperidin-1-yl)-benzooxazol-5-yl]-amide;
2,3-Dihydro-benzofuran-5-carboxylic acid [2-(3-hydroxy-3-methyl-azetidin-1-yl)-benzooxazol-5-yl]-amide;
2,3-Dihydro-benzofuran-5-carboxylic acid [2-(4-dimethyl-amino-piperidin-1-yl)-benzooxazol-5-yl]-amide;
2,3-Dihydro-benzofuran-5-carboxylic acid [2-(6-oxa-1-aza-spiro[3.3]hept-1-yl)-benzooxazol-5-yl]-amide;
2,3-Dihydro-benzofuran-5-carboxylic acid [2-(3,3-difluoro-piperidin-1-yl)-benzooxazol-5-yl]-amide;
2,3-Dihydro-benzofuran-5-carboxylic acid [2-(3-morpholin-4-yl-azetidin-1-yl)-benzooxazol-5-yl]-amide;
2,3-Dihydro-benzofuran-5-carboxylic acid {2-[methyl-(3-methyl-oxetan-3-yl)-amino]-benzooxazol-5-yl}-amide;
2,3-Dihydro-benzofuran-5-carboxylic acid {2-[3-(1,1-di-oxo-1l6-thiomorpholin-4-yl)-azetidin-1-yl]-benzooxazol-5-yl}-amide;
2,3-Dihydro-benzofuran-5-carboxylic acid [2-(3-hydroxy-3-methyl-[1,3']biazetidinyl-1'-yl)-benzooxazol-5-yl]-amide;
2,3-Dihydro-benzofuran-5-carboxylic acid [2-(1-oxa-6-aza-spiro[3.3]hept-6-yl)-benzooxazol-5-yl]-amide;
2,3-Dihydro-benzofuran-5-carboxylic acid [2-(2-oxa-6-aza-spiro[3.4]oct-6-yl)-benzooxazol-5-yl]-amide;
2,3-Dihydro-benzofuran-5-carboxylic acid [2-(6-oxa-2-aza-spiro[3.5]non-2-yl)-benzooxazol-5-yl]-amide;
2,3-Dihydro-benzofuran-5-carboxylic acid [2-(2-oxa-5-aza-spiro[3.4]oct-5-yl)-benzooxazol-5-yl]-amide;
2,3-Dihydro-benzofuran-5-carboxylic acid [2-(1-oxa-6-aza-spiro[3.5]non-6-yl)-benzooxazol-5-yl]-amide;
2,3-Dihydro-benzofuran-5-carboxylic acid [2-(2-oxa-5-aza-spiro[3.5]non-5-yl)-benzooxazol-5-yl]-amide;
2,3-Dihydro-benzofuran-5-carboxylic acid [2-(1-oxa-7-aza-spiro[3.5]non-7-yl)-benzooxazol-5-yl]-amide;
2,3-Dihydro-benzofuran-5-carboxylic acid [2-(1-oxa-7-aza-spiro[3.5]non-7-yl)-benzooxazol-5-yl]-amide;
2,3-Dihydro-benzofuran-5-carboxylic acid [2-(1-oxa-8-aza-spiro[4.5]dec-8-yl)-benzooxazol-5-yl]-amide;
2,3-Dihydro-benzofuran-5-carboxylic acid [2-(7-oxa-2-aza-spiro[3.5]non-2-yl)-benzooxazol-5-yl]-amide;
2,3-Dihydro-benzofuran-5-carboxylic acid [2-(5-oxa-2-aza-spiro[3.4]oct-2-yl)-benzooxazol-5-yl]-amide;
2,3-Dihydro-benzofuran-5-carboxylic acid {2-[3-(4-hydroxy-piperidin-1-yl)-azetidin-1-yl]-benzooxazol-5-yl}-amide;
2,3-Dihydro-benzofuran-5-carboxylic acid [2-(6-methyl-2,6-diaza-spiro[3.5]non-2-yl)-benzooxazol-5-yl]-amide;
2,3-Dihydro-benzofuran-5-carboxylic acid [2-(5-oxa-2-aza-spiro[3.5]non-2-yl)-benzooxazol-5-yl]-amide;
2,3-Dihydro-benzofuran-5-carboxylic acid [2-(1-aza-spiro[3.3]hept-1-yl)-benzooxazol-5-yl]-amide;
2,3-Dihydro-benzofuran-5-carboxylic acid [2-(7-oxa-1-aza-spiro[3.5]non-1-yl)-benzooxazol-5-yl]-amide;

1-{5-[(2,3-Dihydro-benzofuran-5-carbonyl)-amino]-benzooxazol-2-yl}-azetidine-3-carboxylic acid tert-butyl ester;
2,3-Dihydro-benzofuran-5-carboxylic acid [2-(2-oxo-pyrrolidin-1-yl)-benzooxazol-5-yl]-amide;
2,3-Dihydro-benzo[1,4]dioxine-6-carboxylic acid [2-(1,1-dioxo-thiomorpholin-4-yl)-benzooxazol-5-yl]-amide;
Chroman-6-carboxylic acid [2-(1,1-dioxo-thiomorpholin-4-yl)-benzooxazol-5-yl]-amide;
4-Methyl-3,4-dihydro-2H-benzo[1,4]oxazine-6-carboxylic acid [2-(1,1-dioxo-thiomorpholin-4-yl)-benzooxazol-5-yl]-amide;
(R)—N-(2-(3-hydroxypiperidin-1-yl)benzo[d]oxazol-5-yl)-2,3-dihydrobenzofuran-5-carboxamide;
2,3-Dihydro-benzofuran-5-carboxylic acid [2-((S)-3-hydroxy-piperidin-1-yl)-benzooxazol-5-yl]-amide;
2,3-Dihydro-benzofuran-5-carboxylic acid [2-(3-isopropoxy-azetidin-1-yl)-benzooxazol-5-yl]-amide;
2,3-Dihydro-benzofuran-5-carboxylic acid [2-((R)-3-hydroxy-pyrrolidin-1-yl)-benzooxazol-5-yl]-amide;
2,3-Dihydro-benzofuran-5-carboxylic acid [2-((S)-3-hydroxy-pyrrolidin-1-yl)-benzooxazol-5-yl]-amide;
2,3-Dihydro-benzofuran-5-carboxylic acid [2-(3-hydroxy-azetidin-1-yl)-benzooxazol-5-yl]-amide;
2,3-Dihydro-benzofuran-5-carboxylic acid [2-(4-hydroxy-piperidin-1-yl)-benzooxazol-5-yl]-amide;
2,3-Dihydro-benzofuran-5-carboxylic acid [2-(3-phenyl-azetidin-1-yl)-benzooxazol-5-yl]-amide;
2,3-Dihydro-benzofuran-5-carboxylic acid [2-(2-oxa-7-aza-spiro[3.5]non-7-yl)-benzooxazol-5-yl]-amide;
2,3-Dihydro-benzofuran-5-carboxylic acid [2-(2-ethoxymethyl-pyrrolidin-1-yl)-benzooxazol-5-yl]-amide;
2,3-Dihydro-benzofuran-5-carboxylic acid {2-[(3-fluoro-oxetan-3-ylmethyl)-methyl-amino]-benzooxazol-5-yl}-amide;
2,3-Dihydro-benzofuran-5-carboxylic acid [2-(4-oxetan-3-yl-piperazin-1-yl)-benzooxazol-5-yl]-amide
2,3-Dihydro-benzofuran-5-carboxylic acid {2-[methyl-(1-oxetan-3-yl-piperidin-4-yl)-amino]-benzooxazol-5-yl}-amide;
2,3-Dihydro-benzofuran-5-carboxylic acid [2-(2-oxa-6-aza-spiro[3.5]non-6-yl)-benzooxazol-5-yl]-amide;
2,3-Dihydro-benzofuran-5-carboxylic acid [2-(methyl-oxetan-3-ylmethyl-amino)-benzooxazol-5-yl]-amide;
2,3-Dihydro-benzofuran-5-carboxylic acid [2-(methyl-oxetan-3-yl-amino)-benzooxazol-5-yl]-amide;
2,3-Dihydro-benzofuran-5-carboxylic acid [2-(2-methoxymethyl-pyrrolidin-1-yl)-benzooxazol-5-yl]-amide;
2,3-Dihydro-benzofuran-5-carboxylic acid [2-(3-methoxy-piperidin-1-yl)-benzooxazol-5-yl]-amide;
2,3-Dihydro-benzofuran-5-carboxylic acid [2-(3-dimethyl-aminomethyl-pyrrolidin-1-yl)-benzooxazol-5-yl]-amide;
2,3-Dihydro-benzofuran-5-carboxylic acid [2-(2-phenyl-azetidin-1-yl)-benzooxazol-5-yl]-amide;
2,3-Dihydro-benzofuran-5-carboxylic acid [2-(cyclopropyl-oxetan-3-yl-amino)-benzooxazol-5-yl]-amide;
2,3-Dihydro-benzofuran-5-carboxylic acid [2-(3-pyrrolidin-1-yl-azetidin-1-yl)-benzooxazol-5-yl]-amide;
2,3-Dihydro-benzofuran-5-carboxylic acid {2-[3-(1-hydroxy-1-methyl-ethyl)-azetidin-1-yl]-benzooxazol-5-yl}-amide;
2,3-Dihydro-benzofuran-5-carboxylic acid [2-(3-dimethyl-aminomethyl-azetidin-1-yl)-benzooxazol-5-yl]-amide;
2,3-Dihydro-benzofuran-5-carboxylic acid [2-(7-methyl-1,7-diaza-spiro[3.5]non-1-yl)-benzooxazol-5-yl]-amide;
2,3-Dihydro-benzofuran-5-carboxylic acid [2-(7-methyl-2,7-diaza-spiro[3.5]non-2-yl)-benzooxazol-5-yl]-amide;
2,3-Dihydro-benzofuran-5-carboxylic acid [2-(3-dimethyl-amino-azetidin-1-yl)-benzooxazol-5-yl]-amide;
2,3-Dihydro-benzofuran-5-carboxylic acid [2-(2,2-dioxo-2l6-thia-6-aza-spiro[3.3]hept-6-yl)-benzooxazol-5-yl]-amide;
2,3-Dihydro-benzofuran-5-carboxylic acid [2-(6-oxa-1-aza-spiro[3.4]oct-1-yl)-benzooxazol-5-yl]-amide;
2,3-Dihydro-benzofuran-5-carboxylic acid [2-(1,1-dioxo-1l6-thia-6-aza-spiro[3.3]hept-6-yl)-benzooxazol-5-yl]-amide;
2,3-Dihydro-benzofuran-5-carboxylic acid [2-(3-dimethyl-amino-3-methyl-azetidin-1-yl)-benzooxazol-5-yl]-amide;
2,3-Dihydro-benzofuran-5-carboxylic acid [2-(6-oxa-2-aza-spiro[3.4]oct-2-yl)-benzooxazol-5-yl]-amide;
2-(4-Methyl-piperazin-1-yl)-benzooxazole-5-carboxylic acid (2,3-dihydro-benzofuran-5-yl)-amide;
2-Piperidin-1-yl-benzooxazole-5-carboxylic acid (2,3-dihydro-benzofuran-5-yl)-amide;
2-Morpholin-4-yl-benzooxazole-5-carboxylic acid (2,3-dihydro-benzofuran-5-yl)-amide;
2-Diethylamino-benzooxazole-5-carboxylic acid (2,3-dihydro-benzofuran-5-yl)-amide;
2-Pyrrolidin-1-yl-benzooxazole-5-carboxylic acid (2,3-dihydro-benzofuran-5-yl)-amide;
2-(6-Oxa-1-aza-spiro[3.3]hept-1-yl)-benzooxazole-5-carboxylic acid (2,3-dihydro-benzofuran-5-yl)-amide;
2,3-Dihydro-benzofuran-5-carboxylic acid (2-piperidin-1-yl-benzothiazol-5-yl)-amide;
2,3-Dihydro-benzofuran-5-carboxylic acid (2-morpholin-4-yl-benzothiazol-5-yl)-amide;
2,3-Dihydro-benzofuran-5-carboxylic acid [2-(4-methyl-piperazin-1-yl)-benzothiazol-5-yl]-amide;
2,3-Dihydro-benzofuran-5-carboxylic acid (2-pyrrolidin-1-yl-benzothiazol-5-yl)-amide;
2,3-Dihydro-benzofuran-5-carboxylic acid (2-diethylamino-benzothiazol-5-yl)-amide;
2,3-Dihydro-benzofuran-5-carboxylic acid (2-dimethylamino-benzothiazol-5-yl)-amide;
2,3-Dihydro-benzofuran-5-carboxylic acid [2-(3,3-difluoro-azetidin-1-yl)-benzothiazol-5-yl]-amide;
2,3-Dihydro-benzofuran-5-carboxylic acid [2-(3,3-difluoro-pyrrolidin-1-yl)-benzothiazol-5-yl]-amide;
2,3-Dihydro-benzofuran-5-carboxylic acid [2-(3,3-difluoro-piperidin-1-yl)-benzothiazol-5-yl]-amide;
2,3-Dihydro-benzofuran-5-carboxylic acid [2-(6-oxa-1-aza-spiro[3.3]hept-1-yl)-benzothiazol-5-yl]-amide;
2,3-Dihydro-benzofuran-5-carboxylic acid [2-(2-oxa-6-aza-spiro[3.3]hept-6-yl)-benzothiazol-5-yl]-amide
2,3-Dihydro-benzofuran-5-carboxylic acid [2-(1,1-dioxo-1l6-thiomorpholin-4-yl)-benzothiazol-5-yl]-amide;
2,3-Dihydro-benzofuran-5-carboxylic acid [2-(3-methoxy-pyrrolidin-1-yl)-benzothiazol-5-yl]-amide;
2,3-Dihydro-benzofuran-5-carboxylic acid [2-(4-methoxy-piperidin-1-yl)-benzothiazol-5-yl]-amide;
2,3-Dihydro-benzofuran-5-carboxylic acid [2-(3-hydroxy-3-methyl-azetidin-1-yl)-benzothiazol-5-yl]-amide;
(S)—N-(2-(3-hydroxypyrrolidin-1-yl)benzo[d]thiazol-5-yl)-2,3-dihydrobenzofuran-5-carboxamide;
2,3-Dihydro-benzofuran-5-carboxylic acid [2-(2-oxa-7-aza-spiro[3.5]non-7-yl)-benzothiazol-5-yl]-amide;
2,3-Dihydro-benzofuran-5-carboxylic acid {2-[methyl-(1-oxetan-3-yl-piperidin-4-yl)-amino]-benzothiazol-5-yl}-amide;
2,3-Dihydro-benzofuran-5-carboxylic acid [2-(2-oxa-6-aza-spiro[3.5]non-6-yl)-benzothiazol-5-yl]-amide;
2,3-Dihydro-benzofuran-5-carboxylic acid [2-(methyl-oxetan-3-yl-amino)-benzothiazol-5-yl]-amide;

2,3-Dihydro-benzofuran-5-carboxylic acid [2-(3-methoxy-piperidin-1-yl)-benzothiazol-5-yl]-amide;
2,3-Dihydro-benzofuran-5-carboxylic acid [2-(3-hydroxy-azetidin-1-yl)-benzothiazol-5-yl]-amide;
2,3-Dihydro-benzofuran-5-carboxylic acid [2-(4-hydroxy-piperidin-1-yl)-benzothiazol-5-yl]-amide;
2,3-Dihydro-benzofuran-5-carboxylic acid [2-(2-phenyl-azetidin-1-yl)-benzothiazol-5-yl]-amide;
2,3-Dihydro-benzofuran-5-carboxylic acid [2-((R)-3-hydroxy-pyrrolidin-1-yl)-benzothiazol-5-yl]-amide;
2,3-Dihydro-benzofuran-5-carboxylic acid [2-(2-methoxymethyl-pyrrolidin-1-yl)-benzothiazol-5-yl]-amide;
2,3-Dihydro-benzofuran-5-carboxylic acid [2-((S)-3-hydroxy-piperidin-1-yl)-benzothiazol-5-yl]-amide;
2,3-Dihydro-benzofuran-5-carboxylic acid [2-(2-oxa-6-aza-spiro[3.4]oct-6-yl)-benzothiazol-5-yl]-amide;
2,3-Dihydro-benzofuran-5-carboxylic acid [2-((R)-3-hydroxy-piperidin-1-yl)-benzothiazol-5-yl]-amide;
2,3-Dihydro-benzofuran-5-carboxylic acid [2-(2-dimethylaminomethyl-pyrrolidin-1-yl)-benzothiazol-5-yl]-amide;
2,3-Dihydro-benzofuran-5-carboxylic acid (2-azetidin-1-yl-benzooxazol-5-yl)-amide;
2,3-Dihydro-benzofuran-5-carboxylic acid (2-ethylamino-benzooxazol-5-yl)-amide;
2,3-Dihydro-benzofuran-5-carboxylic acid [2-(3-pyridin-2-yl-azetidin-1-yl)-benzooxazol-5-yl]-amide;
Benzo[1,3]dioxole-5-carboxylic acid [2-(3-hydroxy-azetidin-1-yl)-benzooxazol-5-yl]-amide;
Benzo[1,3]dioxole-5-carboxylic acid [2-(1-aza-spiro[3.3]hept-1-yl)-benzooxazol-5-yl]-amide;
Benzo[1,3]dioxole-5-carboxylic acid [2-(6-oxa-1-aza-spiro[3.3]hept-1-yl)-benzooxazol-5-yl]-amide;
Benzo[1,3]dioxole-5-carboxylic acid [2-(6-oxa-1-aza-spiro[3.4]oct-1-yl)-benzooxazol-5-yl]-amide;
Benzo[1,3]dioxole-5-carboxylic acid [2-(7-oxa-1-aza-spiro[3.5]non-1-yl)-benzooxazol-5-yl]-amide;
Benzo[1,3]dioxole-5-carboxylic acid (2-pyrrolidin-1-yl-benzooxazol-5-yl)-amide;
Benzo[1,3]dioxole-5-carboxylic acid [2-(2-oxa-5-aza-spiro[3.4]oct-5-yl)-benzooxazol-5-yl]-amide;
Benzo[1,3]dioxole-5-carboxylic acid (2-piperidin-1-yl-benzooxazol-5-yl)-amide;
Benzo[1,3]dioxole-5-carboxylic acid [2-(3,3-difluoro-piperidin-1-yl)-benzooxazol-5-yl]-amide;
Benzo[1,3]dioxole-5-carboxylic acid [2-(4-methoxy-piperidin-1-yl)-benzooxazol-5-yl]-amide;
Benzo[1,3]dioxole-5-carboxylic acid [2-(2-oxa-7-aza-spiro[3.5]non-7-yl)-benzooxazol-5-yl]-amide;
Benzo[1,3]dioxole-5-carboxylic acid [2-(2-oxa-6-aza-spiro[3.5]non-6-yl)-benzooxazol-5-yl]-amide;
Benzo[1,3]dioxole-5-carboxylic acid [2-(4,4-difluoro-piperidin-1-yl)-benzooxazol-5-yl]-amide;
Benzo[1,3]dioxole-5-carboxylic acid [2-(4-hydroxy-piperidin-1-yl)-benzooxazol-5-yl]-amide;
Benzo[1,3]dioxole-5-carboxylic acid (2-morpholin-4-yl-benzooxazol-5-yl)-amide;
Benzo[1,3]dioxole-5-carboxylic acid [2-(4-methyl-piperazin-1-yl)-benzooxazol-5-yl]-amide;
Benzo[1,3]dioxole-5-carboxylic acid [2-(cyclopropyl-oxetan-3-yl-amino)-benzooxazol-5-yl]-amide;
Benzo[1,3]dioxole-5-carboxylic acid (2-diethylamino-benzooxazol-5-yl)-amide;
Chroman-6-carboxylic acid [2-(3-hydroxy-azetidin-1-yl)-benzooxazol-5-yl]-amide;
Chroman-6-carboxylic acid [2-(1-aza-spiro[3.3]hept-1-yl)-benzooxazol-5-yl]-amide;
Chroman-6-carboxylic acid [2-(6-oxa-1-aza-spiro[3.3]hept-1-yl)-benzooxazol-5-yl]-amide;
Chroman-6-carboxylic acid [2-(6-oxa-1-aza-spiro[3.4]oct-1-yl)-benzooxazol-5-yl]-amide;
Chroman-6-carboxylic acid [2-(7-oxa-1-aza-spiro[3.5]non-1-yl)-benzooxazol-5-yl]-amide;
Chroman-6-carboxylic acid (2-pyrrolidin-1-yl-benzooxazol-5-yl)-amide;
Chroman-6-carboxylic acid [2-(2-oxa-5-aza-spiro[3.4]oct-5-yl)-benzooxazol-5-yl]-amide;
Chroman-6-carboxylic acid (2-piperidin-1-yl-benzooxazol-5-yl)-amide;
Chroman-6-carboxylic acid [2-(4,4-difluoro-piperidin-1-yl)-benzooxazol-5-yl]-amide;
Chroman-6-carboxylic acid [2-(3,3-difluoro-piperidin-1-yl)-benzooxazol-5-yl]-amide;
Chroman-6-carboxylic acid [2-(4-hydroxy-piperidin-1-yl)-benzooxazol-5-yl]-amide;
Chroman-6-carboxylic acid [2-(4-methoxy-piperidin-1-yl)-benzooxazol-5-yl]-amide;
Chroman-6-carboxylic acid [2-(2-oxa-7-aza-spiro[3.5]non-7-yl)-benzooxazol-5-yl]-amide;
Chroman-6-carboxylic acid [2-(2-oxa-6-aza-spiro[3.5]non-6-yl)-benzooxazol-5-yl]-amide;
Chroman-6-carboxylic acid (2-morpholin-4-yl-benzooxazol-5-yl)-amide;
Chroman-6-carboxylic acid [2-(4-methyl-piperazin-1-yl)-benzooxazol-5-yl]-amide;
Chroman-6-carboxylic acid (2-diethylamino-benzooxazol-5-yl)-amide;
Chroman-6-carboxylic acid [2-(cyclopropyl-oxetan-3-yl-amino)-benzooxazol-5-yl]-amide;
2,3-Dihydro-benzo[1,4]dioxine-6-carboxylic acid [2-(3-hydroxy-azetidin-1-yl)-benzooxazol-5-yl]-amide;
2,3-Dihydro-benzo[1,4]dioxine-6-carboxylic acid [2-(6-oxa-1-aza-spiro[3.3]hept-1-yl)-benzooxazol-5-yl]-amide;
2,3-Dihydro-benzo[1,4]dioxine-6-carboxylic acid [2-(1-aza-spiro[3.3]hept-1-yl)-benzooxazol-5-yl]-amide;
2,3-Dihydro-benzo[1,4]dioxine-6-carboxylic acid [2-(6-oxa-1-aza-spiro[3.4]oct-1-yl)-benzooxazol-5-yl]-amide;
2,3-Dihydro-benzo[1,4]dioxine-6-carboxylic acid [2-(7-oxa-1-aza-spiro[3.5]non-1-yl)-benzooxazol-5-yl]-amide;
2,3-Dihydro-benzo[1,4]dioxine-6-carboxylic acid (2-pyrrolidin-1-yl-benzooxazol-5-yl)-amide;
2,3-Dihydro-benzo[1,4]dioxine-6-carboxylic acid [2-(2-oxa-5-aza-spiro[3.4]oct-5-yl)-benzooxazol-5-yl]-amide;
2,3-Dihydro-benzo[1,4]dioxine-6-carboxylic acid (2-piperidin-1-yl-benzooxazol-5-yl)-amide;
2,3-Dihydro-benzo[1,4]dioxine-6-carboxylic acid [2-(4-hydroxy-piperidin-1-yl)-benzooxazol-5-yl]-amide;
2,3-Dihydro-benzo[1,4]dioxine-6-carboxylic acid [2-(3,3-difluoro-piperidin-1-yl)-benzooxazol-5-yl]-amide;
2,3-Dihydro-benzo[1,4]dioxine-6-carboxylic acid [2-(4-methoxy-piperidin-1-yl)-benzooxazol-5-yl]-amide;
2,3-Dihydro-benzo[1,4]dioxine-6-carboxylic acid [2-(4,4-difluoro-piperidin-1-yl)-benzooxazol-5-yl]-amide;
2,3-Dihydro-benzo[1,4]dioxine-6-carboxylic acid [2-(2-oxa-6-aza-spiro[3.5]non-6-yl)-benzooxazol-5-yl]-amide;
2,3-Dihydro-benzo[1,4]dioxine-6-carboxylic acid (2-morpholin-4-yl-benzooxazol-5-yl)-amide;
2,3-Dihydro-benzo[1,4]dioxine-6-carboxylic acid [2-(4-methyl-piperazin-1-yl)-benzooxazol-5-yl]-amide;
2,3-Dihydro-benzo[1,4]dioxine-6-carboxylic acid (2-diethyl amino-benzooxazol-5-yl)-amide;
2,3-Dihydro-benzo[1,4]dioxine-6-carboxylic acid [2-(cyclopropyl-oxetan-3-yl-amino)-benzooxazol-5-yl]-amide;

4-Methyl-3,4-dihydro-2H-benzo[1,4]oxazine-6-carboxylic acid [2-(1-aza-spiro[3.3]hept-1-yl)-benzooxazol-5-yl]-amide;
4-Methyl-3,4-dihydro-2H-benzo[1,4]oxazine-6-carboxylic acid [2-(6-oxa-1-aza-spiro[3.3]hept-1-yl)-benzooxazol-5-yl]-amide;
4-Methyl-3,4-dihydro-2H-benzo[1,4]oxazine-6-carboxylic acid [2-(6-oxa-1-aza-spiro[3.4]oct-1-yl)-benzooxazol-5-yl]-amide;
4-Methyl-3,4-dihydro-2H-benzo[1,4]oxazine-6-carboxylic acid [2-(7-oxa-1-aza-spiro[3.5]non-1-yl)-benzooxazol-5-yl]-amide;
4-Methyl-3,4-dihydro-2H-benzo[1,4]oxazine-6-carboxylic acid [2-(2-oxa-5-aza-spiro[3.4]oct-5-yl)-benzooxazol-5-yl]-amide;
4-Methyl-3,4-dihydro-2H-benzo[1,4]oxazine-6-carboxylic acid (2-piperidin-1-yl-benzooxazol-5-yl)-amide;
4-Methyl-3,4-dihydro-2H-benzo[1,4]oxazine-6-carboxylic acid [2-(4-hydroxy-piperidin-1-yl)-benzooxazol-5-yl]-amide;
4-Methyl-3,4-dihydro-2H-benzo[1,4]oxazine-6-carboxylic acid [2-(4,4-difluoro-piperidin-1-yl)-benzooxazol-5-yl]-amide;
4-Methyl-3,4-dihydro-2H-benzo[1,4]oxazine-6-carboxylic acid [2-(3,3-difluoro-piperidin-1-yl)-benzooxazol-5-yl]-amide;
4-Methyl-3,4-dihydro-2H-benzo[1,4]oxazine-6-carboxylic acid [2-(2-oxa-6-aza-spiro[3.5]non-6-yl)-benzooxazol-5-yl]-amide;
4-Methyl-3,4-dihydro-2H-benzo[1,4]oxazine-6-carboxylic acid [2-(2-oxa-7-aza-spiro[3.5]non-7-yl)-benzooxazol-5-yl]-amide;
4-Methyl-3,4-dihydro-2H-benzo[1,4]oxazine-6-carboxylic acid [2-(4-methoxy-piperidin-1-yl)-benzooxazol-5-yl]-amide;
4-Methyl-3,4-dihydro-2H-benzo[1,4]oxazine-6-carboxylic acid (2-morpholin-4-yl-benzooxazol-5-yl)-amide;
4-Methyl-3,4-dihydro-2H-benzo[1,4]oxazine-6-carboxylic acid [2-(4-methyl-piperazin-1-yl)-benzooxazol-5-yl]-amide;
4-Methyl-3,4-dihydro-2H-benzo[1,4]oxazine-6-carboxylic acid (2-diethylamino-benzooxazol-5-yl)-amide;
4-Methyl-3,4-dihydro-2H-benzo[1,4]oxazine-6-carboxylic acid [2-(cyclopropyl-oxetan-3-yl-amino)-benzooxazol-5-yl]-amide;
2-Piperidin-1-yl-benzothiazole-5-carboxylic acid (2,3-dihydro-benzofuran-5-yl)-amide;
2-(6-Oxa-1-aza-spiro[3.3]hept-1-yl)-benzothiazole-5-carboxylic acid (2,3-dihydro-benzofuran-5-yl)-amide;
2-(4-Methoxy-piperidin-1-yl)-benzothiazole-5-carboxylic acid (2,3-dihydro-benzofuran-5-yl)-amide;
2-(4-Methyl-piperazin-1-yl)-benzothiazole-5-carboxylic acid (2,3-dihydro-benzofuran-5-yl)-amide;
2-(6-Oxa-1-aza-spiro[3.4]oct-1-yl)-benzothiazole-5-carboxylic acid (2,3-dihydro-benzofuran-5-yl)-amide;
2-(6-Oxa-1-aza-spiro[3.3]hept-1-yl)-benzothiazole-5-carboxylic acid (2,3-dihydro-benzo[1,4]dioxin-6-yl)-amide;
2-(6-Oxa-1-aza-spiro[3.4]oct-1-yl)-benzothiazole-5-carboxylic acid (2,3-dihydro-benzo[1,4]dioxin-6-yl)-amide; and
2-(6-Oxa-1-aza-spiro[3.3]hept-1-yl)-benzothiazole-5-carboxylic acid benzo[1,3]dioxol-5-ylamide.

The compounds of compounds of formula (I) as defined in any one of embodiments 1) to 17) and their pharmaceutically acceptable salts can be used as medicaments, e.g. in the form of pharmaceutical compositions for enteral (such especially oral, e.g. in form of a tablet or capsule) or parenteral administration (including intravenous, intraperitoneal, subcutaneous, or topical application, or inhalation).

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, pharmaceutically acceptable solid or liquid carrier materials and, if desired, usual pharmaceutical adjuvants.

The compounds of compounds of formula (I) as defined in any one of embodiments 1) to 17) and their pharmaceutically acceptable salts are useful for modulating NOX4, especially for the prevention or treatment of fibrotic diseases; and/or diseases or disorders associated with an impaired reactive oxygen species (ROS) production.

Fibrotic diseases may defined as comprising pulmonary fibrosis, especially idiopathic pulmonary fibrosis (IPF); scleroderma, especially systemic sclerosis; pancreatic fibrosis; liver fibrosis; chronic kidney disease, especially diabetic nephropathy; and cardiomyopathy (associated with fibrosis) including heart failure resulting from chronic cardiomyopathy, diabetic cardiomyopathy, and hypertrophic cardiomyopathy.

Diseases or disorders associated with impaired reactive oxygen species (ROS) production may defined as comprising pulmonary hypertension; hypertension; asthma; acute respiratory distress syndrome (ARDS); myocardial infarction; acute heart failure; cardiac and skeletal myopathy including Barth syndrome; stroke; traumatic brain injury; neuropathic pain; ataxia telangiectasia (Louis-Bar syndrome); ocular diseases, such as diabetic renopathy; and cancer (especially ovarian cancer, renal cell carcinoma, glioblastoma multiforme, head and neck squamous cell carcinoma (HNSCC), pancreatic adenocarcinoma, colon cancer, urothelial cancer, prostate cancer, breast cancer, non-small cell lung cancer, and metastasis).

In particular, diseases or disorders associated with impaired reactive oxygen species (ROS) production may defined as comprising heart and vascular remodeling in response to pulmonary hypertension; hypertension; asthma; acute respiratory distress syndrome (ARDS); acute myocardial infarction; acute heart failure; heart failure associated with uncontrolled neurohormonal excitation; cardiac and skeletal myopathy including Barth syndrome; acute stroke; and acute traumatic brain injury.

For avoidance of any doubt, if compounds are described as being useful for the prevention or treatment of certain diseases, such compounds are likewise suitable for use in the preparation of a medicament for the prevention or treatment of said diseases.

The present invention also relates to a method for the prevention or treatment of a disease or disorder mentioned herein comprising administering to a subject in need thereof a pharmaceutically active amount of a compound of formula (I) as defined in any one of embodiments 1) to 17).

In a preferred embodiment of the invention, the administered amount of such a compound of formula (I) as defined in any one of embodiments 1) to 17) is comprised between 1 mg and 1000 mg per day, particularly between 5 mg and 500 mg per day, more particularly between 10 mg and 400 mg per day.

The present invention also relates to a method of inhibition of myofibroblast differentiation in a subject (by modulating NOX4), comprising administering to said subject an effective amount of a compound of formula (I) as defined in any one of embodiments 1) to 17); wherein especially said subject has been diagnosed to have a fibrotic disease, and/or a disease or disorder associated with impaired reactive oxygen species (ROS) production.

Said inhibition of myofibroblast differentiation may especially be monitored by
  reduced levels of ROS in organ biopsies (Gorin, Y., et al. Targeting NADPH oxidase with a novel dual NOX1/NOX4 inhibitor attenuates renal pathology in type 1 diabetes. Am J Physiol Renal Physiol, ajprenal 00396 02014 (2015)); and/or
  reduced levels of ROS in exhaled breath condensate (Psathakis, K., et al. Exhaled markers of oxidative stress in idiopathic pulmonary fibrosis. Eur J Clin Invest 36, 362-367 (2006)); and/or
  reduced levels of alpha smooth muscle actin; and/or
  reduced levels of deposited extracellular matrix protein in tissue biopsies (Hecker, L., et al. NADPH oxidase-4 mediates myofibroblast activation and fibrogenic responses to lung injury. Nat Med 15, 1077-1081 (2009));
of said subject (e.g. when compared to the respective levels before said subject has been administered the compound of formula (I)).

The present invention also relates to the use of a compound of Formula (I) for the preparation of a pharmaceutical composition, optionally for use in combination with one or several anti-fibrotic agents [such as, but not limited to kinase inhibitors (more specifically: receptor tyrosine kinase antagonists and/or p38 kinase inhibitors), and/or antagonists of the renin-angiotensin system (RAS), and/or endothelin receptor antagonists, and or stimulators of guanylate cyclase, and/or ligands of peroxisome proliferator activated nuclear receptor gamma (PPARc), and/or antagonists of serotonin signalling, and/or antagonists of integrin-mediated signalling, and/or antagonists of cytokine signalling, and/or antagonists of lysophosphatidic acid (LPA) receptors, and/or therapies targeting M2 type macrophage biology—for the prevention or treatment of the diseases and disorders mentioned herein.

Preparation of the Compounds of Formula (I)

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

Compounds of the Formula (I) of the present invention can be prepared according to the general sequence of reactions outlined below, by known literature methods, by the methods given in the experimental part or by analogous methods. Only a few of the synthetic possibilities leading to compounds of Formula (I) are described. Optimum reaction conditions may vary with the particular reactants or solvents used, but such conditions can be determined by a person skilled in the art by routine optimisation procedures. In some instances the generic groups L, Y, and ring (A) may be incompatible with the assembly illustrated in the schemes below and will require the use of protecting groups. The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. The compounds obtained may also be converted into pharmaceutically acceptable salts thereof in a manner known per se. In the general sequence of reactions outlined below, the generic groups L, X, Y, and ring (A) are as defined for formula (I).

Compounds of Formula (I) wherein L represents —CO—NH— are prepared by reacting a compound of Structure 1 with a compound of Structure 2 by using a coupling reagent such as HATU, TBTU, EDC, etc. in the presence or absence of HOBt, in the presence of a base such Et$_3$N, DIPEA, etc. and in a solvent such as DMF, DCM, THF, etc. Alternatively, coupling of a compound of Structure 1 to a compound of Structure 2 may also be affected by reacting the corresponding acid chloride of a compound of Structure 1.

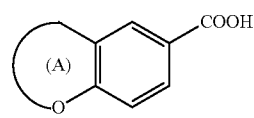

Structure 1

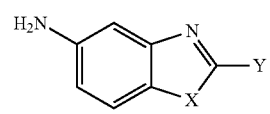

Structure 2

Compounds of Structure 1 are either commercially available or are prepared according to procedures know to the person skilled in the art.

Compounds of Structure 2 are prepared by reducing a compound of Structure 3 e.g. with a hydrogen gas in the presence of a catalyst such as Pd/C, Pt/C, PtO$_2$ in a solvent such as MeOH, EtOH, EA, THF, etc. or mixtures thereof, or with Fe in a solvent such as acetic acid.

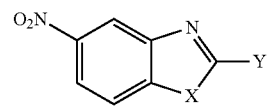

Structure 3

Compounds of Structure 3 are prepared by reacting a compound of Structure 4 with a compound of Structure 5 in the presence or absence of a base such as Et$_3$N, DIPEA, NaHCO$_3$, K$_2$CO$_3$, KOtBu, etc. in a solvent such as THF, DMF, DMSO, etc. or in analogy to literature procedures (e.g. R. E. Martin et al. Bioorg. Med. Chem. Lett. 19 (2009) 6106-6113; F. Hayat et al. Bull. Korean Chem. Soc. 34 (2013) 495-499).

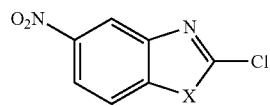

Structure 4

HY

Structure 5

Compounds of Structure 4 are either commercially available or are prepared by reacting a compound of Structure 6 with a chlorinating agent such as SOCl$_2$, SO$_2$Cl$_2$, POCl$_3$, or PCl$_5$ in the presence or absence of a solvent such as DCM, CHCl$_3$, DMF, etc. preferably at temperatures between 20 and 80° C.

Compounds of Structure 5 are either commercially available or are prepared according to procedures known to a person skilled in the art.

Structure 6

Compounds of structure 6 are either commercially available or are prepared according to known literature procedures e.g. L. Zhu et al. J. Heterocycl. Chem. 42 (2005) 727-730, J. C. Mannion et al. WO2011/112602; G. M. Wynne et al. WO2007/091106.

Alternatively, compounds of Formula (I) wherein L represents —CO—NH—* may also be prepared by reacting a compound of structure 7 wherein L represents —CO—NH—* with a compound of structure 5 in the presence or absence of a base such as Et$_3$N, DIPEA, NaHCO$_3$, K$_2$CO$_3$, KOtBu, etc. in a solvent such as THF, DMF, DMSO, etc.

Structure 7

Compounds of structure 7 are prepared by treating a compound of structure 8 wherein L represents —CO—NH—* with a chlorinating reagent such as SOCl$_2$, in presence or absence of a solvent such as DCM, DMF, or DMA.

Structure 8

Compounds of structure 8 can be prepared by reacting a compound of structure 10 with a compound of structure 9 with a base such as Et$_3$N, DIPEA, etc., in a solvent such as DCM, or by reacting a compound of structure 10 with a compound of structure 1 in the presence of a base and in the presence of a coupling reagent such as TBTU, HATU, EDC, etc. in a solvent such as DMF. A compound of structure 10 can also be reacted with a compound of structure 1 by chlorinating a compound structure 1 in situ in the presence of a chlorinating agent such as SOCl$_2$ in the presence or absence of a catalytic amount of DMF in a solvent such as DCM.

Structure 9

Structure 10

Compounds of structure 9 are either commercially available or may be prepared from a compound of structure 1 following known procedures.

Compounds of structure 10 are either commercially available or are prepared according to known procedures, e.g. L. Katz et al. J. Org. Chem. 19 (1954) 758-766, K. D. Rynearson, Bioorg. Med. Chem. Lett. 24 (2014) 3521-3525, D. S. B. Ongarora et al. Bioorg. Med. Chem. Lett. 22 (2012) 5046-5050, L. Zhu et al. J. Heterocycl. Chem. 42 (2005) 727-730, Y. Murti et al. J. Pharm. Res. 7 (2008) 153-155.

Compounds of Formula (I) wherein L represents —NH—CO—* are prepared by reacting a compound of Structure 11 with a compound of Structure 12 by using a coupling reagent such as 1-chloro-N,N-2-trimethylpropenylamine (Ghosez' reagent), HATU, TBTU, EDC, or POCl$_3$ etc. in the presence or absence of HOBt, in the presence of a base such Et$_3$N, DIPEA, etc. and in a solvent such as DCM, DMF, THF, pyridine, or mixtures thereof. Alternatively, coupling of a compound of Structure 11 to a compound of Structure 12 may also be achieved by reacting the corresponding acid chloride of a compound of Structure 12 with a compound of Structure 11.

Structure 11

Structure 12

Compounds of Structure 11 are commercially available or well known in the art.

Compounds of Structure 12 are prepared by saponification of Structure 13, wherein R represents C$_{1-4}$-alkyl, under conditions know to a person skilled in the art, e.g. by exposing a compound of structure 13 to a mixture of aq. NaOH, methanol and THF or to aq. HCl.

Structure 13

Compounds of Structure 13 are prepared by reacting a compound of Structure 14 with a compound of Structure 5 in the presence or absence of a base such as Et$_3$N, DIPEA, NaHCO$_3$, K$_2$CO$_3$, KOtBu, etc. in a solvent such as THF, DMF, DMSO, etc., preferably at temperatures between 20 and 80° C.

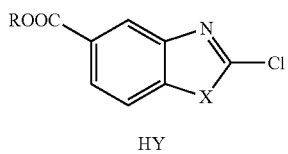

Structure 14

Structure 5

HY

Compounds of Structure 14 are either commercially available or are prepared following literature procedures (e.g. A. Binggeli, WO2007025897), or by chlorinating a compound of Structure 15 with a chlorinating agent such as $POCl_3$, $PCl_5$, $SOCl_2$, $SO_2Cl_2$ in a solvent such as DCM, $CHCl_3$, DMF, etc.

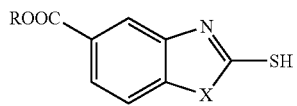

Structure 15

Compounds of Structure 15 are either commercially available or are obtained following literature procedures (e.g. S. Hachiya, WO2008059854, J.-L. Chen WO2005086904).

EXPERIMENTAL PART

The following examples illustrate the invention but do not at all limit the scope thereof.

All temperatures are stated in ° C. Compounds are characterized by $^1$H-NMR (Bruker Avance II, 400 MHz Ultra-Shield™, 400 MHz ($^1$H), 100 MHz ($^{13}$C); or Bruker Avance III HD, Ascend 500 MHz ($^1$H), 125 MHz ($^{13}$C) magnet equipped with DCH cryoprobe); chemical shifts are given in ppm relative to the solvent used; multiplicities: s=singlet, d=doublet, t=triplet, p=pentuplet, hex=hexet, hept=heptet, m=multiplet, br=broad, coupling constants are given in Hz), in case non-deuterated DMSO was used as a solvent, the resonance of the solvent at 2.5 ppm was suppressed; by LC-MS: Finnigan MSQ™ plus or MSQ™ surveyor (Dionex, Switzerland), with HP 1100 Binary Pump and DAD (Agilent, Switzerland), column: Zorbax SB-AQ, 5 μm, 120 Å, 4.6×50 mm (Agilent), gradient: 5-95% acetonitrile in water containing 0.04% of trifluoroacetic acid, within 1 min, flow: 4.5 mL/min; $t_R$ is given in min, or by TLC (TLC-plates from Merck, Silica gel 60 $F_{254}$); or by melting point. Compounds are purified by preparative HPLC (column: X-terra RP18, 50×19 mm, 5 μm, gradient: 10-95% MeCN in water containing 0.5% of formic acid).

Abbreviations (as Used Herein)

abs absolute
aq. aqueous
BSA bovine serum albumin
CC column chromatography on silica gel
DCM dichloromethane
DIPEA Hüning's base, diethylisopropylamine
DMA N,N-dimethylacetamide
DMF dimethylformamide
DMSO dimethylsulfoxide
EA ethyl acetate
EDC N-(3-dimethylaminopropyl)-N'-ethyl-carbodiimide
Et ethyl
EtOH ethanol
h hour(s)
HATU 1-[Bis(dimethylamino)methylene]-1H-1,2,3-triazolo[4,5-b]pyridinium 3-oxide hexafluorophosphate
HBTU O-(benzotriazol-1-yl)-N,N,N',N'-tetramethyluronium hexafluorophosphate
HOBt 1-hydroxy-benzotriazole
HPLC high performance liquid chromatography
HV high vacuum conditions
LC-MS liquid chromatography-mass spectrometry
KOtBu potassium tert.-butylate
Lit. literature
Me methyl
MeCN acetonitrile
MeOH methanol
min minute(s)
$NEt_3$ triethylamine
org. organic
$PPh_3$ triphenylphosphine
PyBOP benzotriazol-1-yl-oxy-tris-pyrrolidino-phosphonium-hexafluoro-phosphate
prep. preparative
rt room temperature
sat. saturated
TBTU 2-(1H-benzotriazole-1-yl)-1,2,3,3-tetramethyluronium tetrafluoroborate
tert. tertiary
TFA trifluoroacetic acid
THF tetrahydrofuran
TLC thin layer chromatography
$t_R$ retention time Preparation of Building Blocks 5-Nitrobenzo[d]oxazole-2-thiol To a solution of 2-amino-4-nitrophenol (10 g, 64.2 mmol) in abs. EtOH (150 mL) potassium ethyl xanthogenate (12.6 g, 77.1 mmol) was added. The mixture was stirred under reflux for 5 h before it was cooled to rt and concentrated. The residue was dissolved in water (300 mL) and treated with 1 M aq. HCl (75 mL) with vigorous stirring. The precipitate that formed was collected, washed with water (50 mL) and dried under HV for 2 days to give the title compound (or tautomer) (11.9 g) as a grey-beige solid; LC-MS: $t_R$=0.71 min; [M+H]$^+$=not detectable; $^1$H NMR (400 MHz, $D_6$-DMSO) δ: 14.33 (s br, 1H), 8.21 (dd, $J_1$=2.3 Hz, $J_2$=8.9 Hz, 1H), 7.96 (d, J=2.3 Hz, 1H), 7.75 (d, J=8.9 Hz, 1H).

2-Chloro-5-nitrobenzo[d]oxazole

To a suspension of 5-nitrobenzo[d]oxazole-2-thiol (5.9 g, 30 mmol) in thionyl chloride (54.7 mL, 751 mmol) DMF (0.04 mL, 0.456 mmol) was added. The mixture was heated to 65° C. and stirred for 1 h. The mixture was cooled to rt and concentrated. The residue was suspended in toluene (30 mL) and the solvent was again evaporated. The residue was then taken up in DCM (25 mL) and purified by CC eluting with heptane:EA 4:1 to give the title compound (4.4 g) as a beige solid; LC-MS: $t_R$=0.78 min; [M+H]+=not detectable; $^1$H NMR (400 MHz, $CDCl_3$) δ: 8.61 (d, J=2.3 Hz, 1H), 8.38 (dd, $J_1$=2.3 Hz, $J_2$=9.0 Hz, 1H), 7.68 (d, J=9.0 Hz, 1H).

5-Nitrobenzo[d]oxazole-2-thiol

A mixture of 2-amino-4-nitrophenol (4.0 g, 26 mmol) and potassium xanthogenate (5.0 g, 31.2 mmol) in EtOH (100 mL) was refluxed for 24 h before it was stirred at rt for two additional days. The precipitate that formed was collected, washed with EtOH and dried to give the title compound (or tautomer) (5.3 g) as an orange solid; LC-MS: $t_R$=0.71 min; [M+H]$^+$=not detectable; $^1$H NMR (400 MHz, D$_6$-DMSO) δ: 7.85 (dd, J$_1$=2.4 Hz, J$_2$=8.6 Hz, 1H), 7.82 (d, J=2.3 Hz, 1H), 7.28 (d, J=8.6 Hz, 1H).

5-Aminobenzo[d]oxazole-2-thiol

To a suspension of 5-nitrobenzo[d]oxazole-2-thiol (1.0 g, 5.1 mmol) in EtOH (38 mL,) and H$_2$O (38 mL) at 80° C. was added NH$_4$Cl (545 mg, 10.2 mmol), followed by Fe (1.40 g, 25 mmol). The resulting mixture was stirred at 80° C. for 1.5 h. The mixture was cooled to rt, filtered and the filtrate was concentrated. The precipitate that formed was collected, washed with water and dried to give the title compound (or tautomer) (640 mg) as a beige powder; LC-MS: $t_R$=0.37 min; [M+H]$^+$=208.06; $^1$H NMR (400 MHz, D$_6$-DMSO) δ: 13.39 (s br, 1H), 7.13 (d, J=8.6 Hz, 1H), 6.36-6.51 (m, 2H), 5.26 (s br, 2H).

Methyl 2-mercaptobenzo[d]oxazole-5-carboxylate

To a solution of methyl 3-amino-5-hydroxybenzoate (1.0 g, 5.98 mmol) in MeOH (13.5 mL) KOH (468 mg, 7.18 mmol) was added. The mixture was stirred at rt until all KOH had dissolved. Then CS$_2$ (9.02 mL, 150 mmol) was added and the mixture was stirred at 60° C. for 16 h before it was cooled to 0° C. and diluted with EA (50 mL). 1M aq. HCl (8.6 mL) was added to acidify the mixture to pH 1. The organic layer was separated, washed with water (25 mL), dried over MgSO$_4$, filtered and concentrated to give the title compound (or tautomer) (1.18 g) as a solid; LC-MS: $t_R$=0.72 min; [M+H]$^+$=209.96; $^1$H NMR (400 MHz, D$_6$-DMSO) δ: 14.14 (s, 1H), 7.89 (dd, J$_1$=1.7 Hz, J$_2$=8.5 Hz, 1H), 7.69 (d, J=1.5 Hz, 1H), 7.63 (d, J=8.5 Hz, 1H), 3.88 (s, 3H).

Methyl 2-chlorobenzo[d]oxazole-5-carboxylate

To a solution of methyl 2-mercaptobenzo[d]oxazole-5-carboxylate 1.08 g, 5.16 mmol) in DCM (5.5 mL) POCl$_3$ (4.25 mL, 46.5 mmol) followed by PCl$_5$ (1.29 g, 6.19 mmol) was added. The mixture was stirred at rt for 8 h before it was concentrated. The remaining oil was cooled with an ice bath before sat. aq. NaHCO$_3$ solution (50 mL) was added. When the evolution of gas had ceased the mixture was transferred to a separating funnel and extracted twice with DCM (2×50 mL). The combined organic extracts were dried over MgSO$_4$, filtered and concentrated. The crude product was suspended in diethyl ether (10 mL). The suspension was stirred for 10 min before it was filtered. The filtrate was concentrated and dried to give the title compound (0.62 g) as a solid; LC-MS: $t_R$=0.80 min; [M+H+CH$_3$CN]$^+$=253.04; $^1$H NMR (400 MHz, CDCl$_3$) δ: 8.40 (d, J=1.2 Hz, 1H), 8.15 (dd, J$_1$=1.6 Hz, J$_2$=8.7 Hz, 1H), 7.58 (d, J=8.6 Hz, 1H), 3.99 (s, 3H).

5-Nitrobenzo[d]thiazole-2-thiol

To a solution of 2-fluoro-5-nitroaniline (3.12 g, 20 mmol) in DMF (15 mL) potassium ethyl xanthogenate (3.93 g, 24 mmol) was added. The mixture was stirred at 100° C. for 5 h before it was cooled to rt, diluted with water (25 mL) and 1 M aq. HCl (35 mL). The precipitate that formed was collected, washed with water (15 mL) and dried to give the title compound (or tautomer) (3.99 g) as a beige solid; LC-MS: $t_R$=0.76 min; [M+H]$^+$=not detectable; $^1$H NMR (400 MHz, D$_6$-DMSO) δ: 14.17 (s, 1H), 8.15 (dd, J$_1$=2.2 Hz, J$_2$=8.8 Hz, 1H), 7.99 (d, J=9.0 Hz), 7.97 (d, J=2.3 Hz).

2-Chloro-5-nitrobenzo[d]thiazole

Solid 5-nitrobenzo[d]thiazole-2-thiol (4.0 g, 18.8 mmol) was placed in a round bottom flask and cooled to 0° C. while SO$_2$Cl$_2$ (9.1 mL, 113 mmol) was slowly added at 0° C. Upon complete additions, the yellow suspension was stirred at 0° C. for 5 min, then at rt for 2 h. The mixture was poured onto ice/water (200 mL) and stirred for 1 h. The precipitate that formed was collected, washed with water and dried under high vacuum. The material was slurried in EA (25 mL), vigorously stirred for 15 min and filtered. The filtrate was concentrated and dried. The obtained solid absorbed to silica gel and purified by CC eluting with heptane:EA 4:1 to give the title compound (2.02 g) as a solid; LC-MS: $t_R$=0.84 min; [M+H]$^+$=214.51; $^1$H NMR (400 MHz, CDCl$_3$) δ: 8.84 (d, J=2.2 Hz, 1H), 8.35 (dd, J$_1$=2.2 Hz, J$_2$=8.9 Hz, 1H), 7.98 (d, J=8.9 Hz, 1H).

2-Chlorobenzo[d]thiazol-5-amine

To a solution of 2-chloro-5-nitrobenzo[d]thiazole (2.18 g, 10.2 mmol) in EtOH:acetic acid 91:9 (102 mL) iron powder (5.70 g, 102 mmol) was carefully added. The mixture was refluxed for 1.5 h before it was filtered. The filtrate was concentrated to about one third of the volume and the pH of the solution was adjusted to pH 8 by adding 10% aq. NaOH solution. The mixture was extracted with EA (150 mL). The organic extract was washed with brine, dried over Na$_2$SO$_4$, filtered and concentrated. The crude product was suspended in EtOH (4 mL), filtered, washed with additional EtOH (0.5 mL) and dried to give the title compound (1.55 g) as a solid; LC-MS: $t_R$=0.78 min; [M+H]$^+$=185.03; $^1$H NMR (400 MHz, D$_6$-DMSO) δ: 7.65 (d, J=8.7 Hz, 1H), 7.06 (d, J=1.9 Hz, 1H), 6.79 (dd, J$_1$=2.0 Hz, J$_2$=8.7 Hz, 1H), 5.43 (s, 2H).

2-Chloro-benzothiazole-5-carbonyl chloride

To a mixture of 2-sulfanyl-1,3-benzothiazole-5-carboxylic acid (50.1 mg, 0.237 mmol), PCl$_5$ (158 mg, 0.745 mmol) and POCl$_3$ (0.446 mL, 4.74 mmol), DMF (0.042 mL, 0.524 mmol) was carefully added. The mixture became warm and the thick suspension was stirred at rt for 3 h to become a clear solution. The mixture was concentrated and diluted with DCM, solid material was filtered off and the filtrate was concentrated and dried to give the crude title compound (92 mg) as a pale yellow resin which was used without further purification; LC-MS: $t_R$=0.91 min; [M+H]$^+$=not detectable.

Preparation of Intermediates

Intermediate A1

4-(5-Aminobenzo[d]oxazol-2-yl)thiomorpholine 1,1-dioxide a) To a solution of 2-chloro-5-nitrobenzo[d]oxazole (1.0 g, 5.0 mmol) and Et$_3$N (2.1 mL, 15.1 mmol) in THF (25 mL) thiomorpholine 1,1-dioxide (715 mg, 5.29 mmol) was added. The mixture was stirred at 70° C. for 3 h before it was diluted with water (100 mL) and extracted with EA (200 mL) followed by DCM (100 mL). The combined org. extracts were dried over MgSO$_4$, filtered and concentrated. The remaining solid was suspended in DCM (10 mL), filtered off, washed with additional DCM (5 mL) and dried to give a first batch of the title compound (698 mg). The filtrate was concentrated and once more suspended in DCM (2 mL). Solid material was collected, washed with a small amount of DCM and dried to give a second batch of the title compound (460 mg). The obtained solid materials were combined; LC-MS: $t_R$=0.69 min; [M+H]$^+$=297.98; $^1$H NMR (400 MHz, $D_6$-DMSO) δ: 8.15 (d, J=2.3 Hz, 1H), 8.04 (dd, $J_1$=2.3 Hz, $J_2$=8.8 Hz, 1H), 7.71 (d, J=8.8 Hz, 1H), 4.08-4.16 (m, 4H), 3.35-3.42 (m, 4H).

b) To a solution of 4-(5-nitrobenzo[d]oxazol-2-yl)thiomorpholine 1,1-dioxide (1.10 g, 3.7 mmol) in acetic acid (25 mL) iron powder (2.07 g, 37 mmol) was added carefully. The mixture was stirred at 40° C. for 2 h before it was filtered. The filtrate is diluted with water (50 mL) and the pH was adjusted to 13-14 by adding 5 M aq. NaOH solution. The mixture was extracted twice with DCM (2×100 mL), the combined org. extracts were dried over $MgSO_4$, filtered and dried to give the title compound (908 mg) as a grey solid; LC-MS: $t_R$=0.38 min; [M+H]$^+$=268.07; $^1$H NMR (400 MHz, $D_6$-DMSO) δ: 7.07 (d, J=8.5 Hz, 1H), 6.53 (d, J=2.1 Hz, 1H), 6.28 (dd, $J_1$=2.2 Hz, $J_2$=8.5 Hz, 1H), 4.84 (s, 2H), 3.98-4.05 (m, 4H), 3.26-3.32 (m, 4H).

or alternatively:

b) To a mixture of 4-(5-nitrobenzo[d]oxazol-2-yl)thiomorpholine 1,1-dioxide (10 mg, 0.05 mmol) in degassed EA (0.5 mL) wet Pd/C (10 mg) was added before it was stirred under 4 bar of $H_2$ at rt for 16 h. The catalyst was removed by filtration and the filtrate was concentrated and dried to give the title compound (5 mg).

Intermediates A2 to A38

The following 5-amino-benzo[d]oxazol derivatives were obtained in analogy to Intermediate A1:

Intermediate A5: $^1$H NMR (500 MHz, $D_6$-DMSO) δ: 7.04 (d, J=8.4 Hz, 1H), 6.50 (d, J=2.1 Hz, 1H), 6.25 (dd, $J_1$=2.2 Hz, $J_2$=8.4 Hz, 1H), 4.81 (s, 2H), 3.67-3.73 (m, 4H), 3.48-3.55 (m, 4H).

Intermediate A39

1-(5-Aminobenzo[d]oxazol-2-yl)pyrrolidin-2-one a) To a solution of 2-chloro-5-nitrobenzo[d]oxazole (800 mg, 4.03 mmol) in DCM (25 mL) were added ethyl 4-aminobutyrate hydrochloride (810 mg, 4.83 mmol) followed by DIPEA (1.59 mL, 9.27 mmol) at 0° C. The mixture was stirred at rt overnight before it was concentrated in vacuo, diluted with EA, washed with brine, dried over $MgSO_4$, filtered and concentrated. The crude product was purified by CC eluting with heptane:EA 1:1 to give ethyl 4-((5-nitrobenzo[d]oxazol-2-yl)amino)butanoate (1.01 g) as a yellow powder, LC-MS: $t_R$=0.77 min; [M+H]$^+$=294.1.

b) A suspension of ethyl 4-((5-nitrobenzo[d]oxazol-2-yl)amino)butanoate (1.01 g, 3.44 mmol) in EtOH (20 mL) and 1M aq. NaOH (5.2 mL) was stirred at rt overnight before it was cooled with an ice bath. 1 M aq. HCl was added (5.2 mL) and the mixture was concentrated and dried to give crude 4-((5-nitrobenzo[d]oxazol-2-yl)amino)butanoic acid (1.22 g) as a yellow powder, LC-MS: $t_R$=0.60 min; [M+H]$^+$=266.14. This material was dissolved in DCM (25 mL) and $SOCl_2$ (0.89 mL, 12.1 mmol) was added. The mixture was stirred at rt for 2 h before it was concentrated in vacuo,

| Intermediate | Name | LC-MS | |
|---|---|---|---|
| | | $t_R$ [min] | [M + H]$^+$ |
| A2 | 2-(piperidin-1-yl)benzo[d]oxazol-5-amine | 0.52 | 218.31 |
| A3 | 2-(pyrrolidin-1-yl)benzo[d]oxazol-5-amine | 0.46 | 204.29 |
| A4 | 2-(4-methylpiperazin-1-yl)benzo[d]oxazol-5-amine | 0.17 | 233.29 |
| A5 | 2-morpholinobenzo[d]oxazol-5-amine | 0.42 | 220.30 |
| A6 | $N^2,N^2$-diethylbenzo[d]oxazole-2,5-diamine | 0.50 | 206.27 |
| A7 | 2-(2-oxa-6-azaspiro[3.3]heptan-6-yl)benzo[d]oxazol-5-amine | 0.42 | 232.24 |
| A8 | 2-(4,4-difluoropiperidin-1-yl)benzo[d]oxazol-5-amine | 0.54 | 254.24 |
| A9 | 2-(3,3-difluoroazetidin-1-yl)benzo[d]oxazol-5-amine | 0.46 | 267.26* |
| A10 | 2-(3,3-difluoropyrrolidin-1-yl)benzo[d]oxazol-5-amine | 0.50 | 240.24 |
| A11 | 2-(3-methoxypyrrolidin-1-yl)benzo[d]oxazol-5-amine | 0.45 | 234.12 |
| A12 | 2-(4-methoxypiperidin-1-yl)benzo[d]oxazol-5-amine | 0.49 | 248.29 |
| A13 | 1-(5-aminobenzo[d]oxazol-2-yl)-3-methylazetidin-3-ol | 0.40 | 220.24 |
| A14 | $N^2$-(2-(dimethylamino)ethyl)-$N^2$-methylbenzo[d]oxazole-2,5-diamine | 0.18 | 234.93 |
| A15 | 2-(4-(dimethylamino)piperidin-1-yl)benzo[d]oxazol-5-amine | 0.29 | 261.33 |
| A16 | 2-(6-oxa-1-azaspiro[3.3]heptan-1-yl)benzo[d]oxazol-5-amine | 0.42 | 232.24 |
| A17 | 2-(3,3-difluoropiperidin-1-yl)benzo[d]oxazol-5-amine | 0.53 | 254.26 |
| A18 | 2-(3-morpholinoazetidin-1-yl)benzo[d]oxazol-5-amine | 0.24 | 275.16 |
| A19 | $N^2$-methyl-$N^2$-(3-methyloxetan-3-yl)benzo[d]oxazole-2,5-diamine | 0.45 | 234.24 |
| A20 | 4-(1-(5-aminobenzo[d]oxazol-2-yl)azetidin-3-yl)thiomorpholine 1,1-dioxide | 0.43 | 323.00 |
| A21 | 1'-(5-aminobenzo[d]oxazol-2-yl)-3-methyl-[1,3'-biazetidin]-3-ol | 0.24 | 275.05 |
| A22 | 2-(1-oxa-6-azaspiro[3.3]heptan-6-yl)benzo[d]oxazol-5-amine | 0.44 | 232.11 |
| A23 | 2-(2-oxa-6-azaspiro[3.4]octan-6-yl)benzo[d]oxazol-5-amine | 0.44 | 246.15 |
| A24 | 2-(6-oxa-2-azaspiro[3.5]nonan-2-yl)benzo[d]oxazol-5-amine | 0.50 | 260.15 |
| A25 | 2-(2-oxa-5-azaspiro[3.4]octan-5-yl)benzo[d]oxazol-5-amine | 0.45 | 246.14 |
| A26 | 2-(1-oxa-6-azaspiro[3.5]nonan-6-yl)benzo[d]oxazol-5-amine | 0.46 | 260.15 |
| A27 | 2-(2-oxa-5-azaspiro[3.5]nonan-5-yl)benzo[d]oxazol-5-amine | 0.49 | 260.15 |
| A28 | 2-(1-oxa-7-azaspiro[3.5]nonan-7-yl)benzo[d]oxazol-5-amine | 0.47 | 260.16 |
| A29 | 2-(8-oxa-2-azaspiro[4.5]decan-2-yl)benzo[d]oxazol-5-amine | 0.49 | 274.16 |
| A30 | 2-(1-oxa-8-azaspiro[4.5]decan-8-yl)benzo[d]oxazol-5-amine | 0.53 | 274.16 |
| A31 | 2-(7-oxa-2-azaspiro[3.5]nonan-2-yl)benzo[d]oxazol-5-amine | 0.48 | 260.16 |
| A32 | 2-(5-oxa-2-azaspiro[3.4]octan-2-yl)benzo[d]oxazol-5-amine | 0.48 | 246.15 |
| A33 | 1-(1-(5-aminobenzo[d]oxazol-2-yl)azetidin-3-yl)piperidin-4-ol | 0.20 | 289.15 |
| A34 | 2-(6-methyl-2,6-diazaspiro[3.5]nonan-2-yl)benzo[d]oxazol-5-amine | 0.34 | 273.18 |
| A35 | 2-(5-oxa-2-azaspiro[3.5]nonan-2-yl)benzo[d]oxazol-5-amine | 0.52 | 260.15 |
| A36 | 2-(1-azaspiro[3.3]heptan-1-yl)benzo[d]oxazol-5-amine | 0.55 | 230.18 |
| A37 | 2-(7-oxa-1-azaspiro[3.5]nonan-1-yl)benzo[d]oxazol-5-amine | 0.48 | 260.16 |
| A38 | tert-butyl 1-(5-aminobenzo[d]oxazol-2-yl)azetidine-3-carboxylate | 0.60 | 290.15 |

*represents [M + H + $CH_3CN$]$^+$.

dissolved in pyridine (10 mL) and stirred at rt for 1 h. The mixture was again concentrated, diluted with DCM and washed with brine. The organic extract was separated and the precipitate that formed was removed by filtration (unreacted SM). The filtrate was dried over $MgSO_4$, filtered and concentrated. The crude product was first purified by CC eluting with DCM:MeOH 10:1, then by prep. HPLC to give 1-(5-nitrobenzo[d]oxazol-2-yl)pyrrolidin-2-one (133 mg) as a white solid, LC-MS: $t_R$=0.64 min; [M+H]$^+$=248.11; $^1$H NMR (400 MHz, CDCl$_3$) δ: 8.50 (d, J=2.3 Hz, 1H), 8.25 (dd, J$_1$=2.3 Hz, J$_2$=8.9 Hz, 1H), 7.65 (d, J=8.8 Hz, 1H), 4.17-4.23 (m, 2H), 2.76 (t, J=7.9 Hz, 2H), 2.30-2.39 (m, 2H).

c) To a solution of 1-(5-nitrobenzo[d]oxazol-2-yl)pyrrolidin-2-one (133 mg, 0.538 mmol) in EA (2 mL) Pd/C (7 mg, 10% Pd, 50% wet) was added. The mixture was stirred under 1 bar of H$_2$ at rt for 18 h before the catalyst was removed by filtration. The filtrate was concentrated and dried to give 1-(5-aminobenzo[d]oxazol-2-yl)pyrrolidin-2-one (105 mg) as a white solid, LC-MS: $t_R$=0.32 min; [M+H]$^+$=218.11.

1H), 7.55 (dd, J$_1$=1.8 Hz, J$_2$=8.8 Hz, 1H), 7.48 (d, J=8.8 Hz, 1H), 6.90 (d, J=8.4 Hz, 1H), 4.64 (t, J=8.8 Hz, 2H), 3.27 (t, J=8.8 Hz, 2H).

Intermediate C1

2-(4-methylpiperazin-1-yl)benzo[d]oxazole-5-carboxylic acid a) To a solution of methyl 2-chlorobenzo[d]oxazole-5-carboxylate (98.5 mg, 465 μmol) in THF (1.5 mL) Et$_3$N (195 μL, 1.4 mmol) followed by 1-methylpiperazine (63 μL, 559 μmol) was added. The mixture was stirred at 65° C. for 16 h before it was cooled to rt and concentrated. The residue was dissolved in CH$_3$CN (1 mL) and DMF (1 mL), filtered and the filtrate was separated by prep. HPLC to give methyl 2-(4-methylpiperazin-1-yl)benzo[d]oxazole-5-carboxylate (80 mg) as a solid; LC-MS: $t_R$=0.51 min; [M+H]$^+$=276.16; $^1$H NMR (400 MHz, CDCl$_3$) δ: 8.04 (d, J=1.5 Hz, 1H), 7.83 (dd, J$_1$=1.7 Hz, J$_2$=8.4 Hz, 1H), 7.29 (d, J=8.3 Hz, 1H), 3.94 (s, 3H), 3.77-3.82 (m, 4H), 2.57-2.62 (m, 4H), 2.41 (s, 3H).

| | | LC-MS | |
|---|---|---|---|
| Intermediate | Name | $t_R$ [min] | [M + H]$^+$ |
| A40 | 2-Azetidin-1-yl-benzooxazol-5-ylamine | 0.43 | 190.16 |
| A41 | 1-(5-Amino-benzooxazol-2-yl)-piperidin-4-ol | 0.54 | 234.15 |
| A42 | 2-(2-Oxa-7-aza-spiro[3.5]non-7-yl)-benzooxazol-5-ylamine | 0.64 | 260.15 |
| A43 | 1-(5-Amino-benzooxazol-2-yl)-azetidin-3-ol | 0.50 | 206.15 |
| A44 | N$^2$-Cyclopropyl-N$^2$-oxetan-3-yl-benzooxazole-2,5-diamine | 0.65 | 246.12 |
| A45 | 2-(6-Oxa-1-aza-spiro[3.4]oct-1-yl)-benzooxazol-5-ylamine | 0.62 | 246.14 |
| A46 | 2-(2-Oxa-6-aza-spiro[3.5]non-6-yl)-benzooxazol-5-ylamine | 0.66 | 260.14 |
| A47 | N$^2$-Ethyl-benzooxazole-2,5-diamine | 0.36 | 178.18 |
| A48 | 2-(3-Pyridin-2-yl-azetidin-1-yl)-benzooxazol-5-ylamine | 0.38 | 267.08 |

Intermediate B1

N-(2-Mercaptobenzo[d]oxazol-5-yl)-2,3-dihydrobenzofuran-5-carboxamide

To a mixture of 5-aminobenzo[d]oxazole-2-thiol (540 mg, 3.25 mmol) in pyridine (27 mL) was added 2,3-dihydrobenzofuran-5-carbonyl chloride (593 mg, 3.25 mmol) at rt. The reaction mixture was stirred at rt for 1.5 h before another portion of 2,3-dihydrobenzofuran-5-carbonyl chloride (30 mg, 0.16 mmol) was added. Stirring was continued at rt for 1 h before the mixture was concentrated. The residue was treated with water, the resulting suspension was sonicated before the solid material was collected by filtration, washed b) To a solution of methyl 2-(4-methylpiperazin-1-yl)benzo[d]oxazole-5-carboxylate (76 mg, 0.28 mmol) in THF (1 mL) and MeOH (1 mL) a 1 M aq. solution of NaOH (0.55 mL) was added. The mixture was stirred at rt for 18 h before it was neutralized by adding 1 M aq. HCl. The precipitate that formed was collected and dried to give the title compound (49 mg) as hydrochloride salt as a white solid; LC-MS: $t_R$=0.43 min; [M+H]$^+$=262.11; $^1$H NMR (400 MHz, DMSO) δ: 12.93 (s, 1H), 11.04 (s, 1H), 7.85 (d, J=1.5 Hz, 1H), 7.75 (dd, J$_1$=1.7 Hz, J$_2$=8.4 Hz, 1H), 7.56 (d, J=8.4 Hz, 1H), 4.21-4.37 (m, 2H), 3.43-3.71 (m, 4H), 3.08-3.27 (m, 2H), 2.80 (s, 3H).

Intermediates C2 to C6

The following 2-aminobenzo[d]oxazole-5-carboxylic acid derivatives were obtained in analogy to Intermediate C1:

| | | LC-MS | |
|---|---|---|---|
| Intermediate | Name | $t_R$ [min] | [M + H]$^+$ |
| C2 | 2-Piperidin-1-yl-benzooxazole-5-carboxylic acid | 0.70 | 247.13 |
| C3 | 2-Morpholin-4-yl-benzooxazole-5-carboxylic acid | 0.61 | 249.11 |
| C4 | 2-Diethylamino-benzooxazole-5-carboxylic acid | 0.68 | 235.11 |
| C5 | 2-Pyrrolidin-1-yl-benzooxazole-5-carboxylic acid | 0.61 | 233.16 |
| C6 | 2-(6-Oxa-1-aza-spiro[3.3]hept-1-yl)-benzooxazole-5-carboxylic acid | 0.60 | 261.04 | and dried to give the title compound (890 mg) as a pink solid; LC-MS: $t_R$=0.77 min; [M+H]$^+$=312.97; $^1$H NMR (400 MHz, D$_6$-DMSO) δ: 13.84 (s br, 1H), 10.21 (s, 1H), 7.93 (d, J=1.7 Hz, 1H), 7.88 (s, 1H), 7.80 (dd, J$_1$=1.3 Hz, J$_2$=8.3 Hz, Intermediate C2: $^1$H NMR (400 MHz, D$_6$-DMSO) δ: 12.82 (s, 1H), 7.76 (d, J=1.5 Hz, 1H), 7.66 (dd, J$_1$=1.7 Hz, J$_2$=8.3 Hz, 1H), 7.47 (d, J=8.3 Hz, 1H), 3.59-3.65 (m, 4H), 1.57-1.68 (m, 6H).

Intermediate C3: ¹H NMR (400 MHz, D₆-DMSO) δ: 12.86 (s, 1H), 7.81 (d, J=1.6 Hz, 1H), 7.70 (dd, J₁=1.6 Hz, J₂=8.3 Hz, 1H), 7.51 (d, J=8.3 Hz, 1H), 3.71-3.76 (m, 4H), 3.60-3.65 (m, 4H).

Intermediate C4: ¹H NMR (400 MHz, D₆-DMSO) δ: 12.80 (s, 1H), 7.76 (d, J=1.6 Hz, 1H), 7.65 (dd, J₁=1.7 Hz, J₂=8.3 Hz, 1H), 7.48 (d, J=8.3 Hz, 1H), 3.56 (q, J=7.1 Hz, 4H), 1.22 (t, J=7.1 Hz, 7H).

Intermediate C5: ¹H NMR (400 MHz, De-DMSO) δ: 12.80 (s, 1H), 7.77 (d, J=1.6 Hz, 1H), 7.65 (dd, J₁=1.7 Hz, J₂=8.3 Hz, 1H), 7.48 (d, J=8.3 Hz, 1H), 3.54-3.60 (m, 4H), 1.95-2.01 (m, 4H).

Intermediate C6: ¹H NMR (400 MHz, D₆-DMSO) δ: 12.88 (s, 1H), 7.87 (d, J=1.5 Hz, 1H), 7.72 (dd, J₁=1.7 Hz, J₂=8.3 Hz, 1H), 7.57 (d, J=8.4 Hz, 1H), 5.22 (d, J=7.7 Hz, 2H), 4.67 (d, J=7.7 Hz, 2H), 4.04 (t, J=7.2 Hz, 2H), 2.73 (t, J=7.3 Hz, 2H).

Intermediate D1

2-(Piperidin-1-yl)benzo[d]thiazol-5-amine a) To a solution of 2-chloro-5-nitrobenzo[d]thiazole (200 mg, 931 µmol) in THF (1.5 mL) Et₃N (0.195 mL, 1.4 mmol) followed by piperidine (0.138 mL, 1.4 mmol) was added. The mixture was stirred at 65° C. for 1 h before it was diluted with EA (50 mL) and washed with water (50 mL). The organic extract was dried over MgSO₄, filtered and concentrated to give 5-nitro-2-(piperidin-1-yl)benzo[d]thiazole (250 mg) as a solid; LC-MS: $t_R$=0.92 min; [M+H]⁺=264.18.

b) To a solution of 5-nitro-2-(piperidin-1-yl)benzo[d]thiazole (245 mg, 0.93 mmol) in EtOH (15 mL) Pd/C (125 mg, 10% Pd, 50% water wet) was added. The mixture was stirred under 1 atm of H₂ for 4 days before the catalyst was removed by filtration and the filtrate was evaporated. The crude product was purified by prep. HPLC to give the title compound (73 mg) as a solid; LC-MS: $t_R$=0.54 min; [M+H]⁺=234.17; ¹H NMR (400 MHz, CDCl₃) δ: 7.33 (d, J=8.3 Hz, 1H), 6.93 (d, J=2.2 Hz, 1H), 6.49 (dd, J₁=2.2 Hz, J₂=8.3 Hz, 1H), 3.77 (s br, 2H), 3.56-3.64 (m, 4H), 1.67-1.77 (m, 6H).

Intermediates D2 to D17

The following 5-amino-benzo[d]thiazol derivatives were obtained in analogy to Intermediate D1:

Intermediate D2: ¹H NMR (400 MHz, CDCl₃) δ: 7.37 (d, J=8.3 Hz, 1H), 6.96 (d, J=2.2 Hz, 1H), 6.54 (dd, J₁=2.2 Hz, J₂=8.3 Hz, 1H), 3.83-3.87 (m, 4H), 3.60-3.66 (m, 4H).

Intermediate D3: ¹H NMR (400 MHz, CDCl₃) δ: 7.36 (d, J=8.3 Hz, 1H), 6.93 (d, J=2.2 Hz, 1H), 6.52 (dd, J₁=2.2 Hz, J₂=8.3 Hz, 1H), 3.70 (s br, 2H), 3.63-3.68 (m, 4H), 2.51-2.61 (m, 4H), 2.39 (s, 3H).

Intermediated D9: ¹H NMR (400 MHz, CDCl₃) δ: 7.36 (d, J=8.3 Hz, 1H), 6.96 (d, J=2.2 Hz, 1H), 6.54 (dd, J₁=2.2 Hz, J₂=8.4 Hz, 1H), 3.88 (t, J=11.4 Hz, 2H), 3.62-3.68 (m, 2H), 2.07-2.19 (m, 2H), 1.92-2.00 (m, 2H).

Intermediate D10: ¹H NMR (400 MHz, CDCl₃) δ: 7.38 (d, J=8.4 Hz, 1H), 7.09 (s, 1H), 6.57 (dd, J₁=1.8 Hz, J₂=8.5 Hz, 1H), 5.48 (d, J=7.7 Hz, 2H), 4.75 (d, J=7.7 Hz, 2H), 4.15 (t, J=7.2 Hz, 2H), 2.74 (t, J=7.4 Hz, 2H).

Intermediate E1

N-(2-Chlorobenzo[d]thiazol-5-yl)-2,3-dihydrobenzofuran-5-carboxamide

To a solution of 2,3-dihydrobenzo[b]furan carboxylic acid (1.27 g, 7.5 mmol) in DMF (22.5 mL) TBTU (2.48 g, 7.5 mmol) followed by DIPEA (3.93 mL, 22.5 mmol) was added. The mixture was stirred at rt for 15 min before 2-chlorobenzo[d]thiazol-5-amine (1.52 g, 7.5 mmol) was added. Stirring is continued at 55° C. for 18 h. The mixture was concentrated, diluted with DCM (250 mL) and washed with sat. aq. NaHCO₃ solution (125 mL). The organic extract was separated and concentrated. The crude product was purified by CC eluting with a gradient of heptane:EE 1:2 to pure EA to give the title compound (980 mg) as a solid; LC-MS*: $t_R$=1.01 min; [M+H]⁺=330.95 (*=0.5% NH₄OH instead of TFA in eluting solvent.); ¹H NMR (400 MHz, DMSO) δ: 10.32 (s, 1H), 8.50 (d, J=1.9 Hz, 1H), 8.04 (d, J=8.8 Hz, 1H), 7.92 (s, 1H), 7.87 (dd, J₁=2.0 Hz, J₂=8.8 Hz, 1H), 7.83 (dd, J₁=1.9 Hz, J₂=8.4 Hz, 1H), 6.91 (d, J=8.4 Hz, 1H), 4.65 (t, J=8.8 Hz, 2H), 3.28 (t, J=8.7 Hz, 2H).

Intermediate E2

2-Chloro-N-(2,3-dihydrobenzofuran-5-yl)benzo[d]thiazole-5-carboxamide

A solution of 2,3-dihydro-1-benzofuran-5-amine (33.7 mg, 0.237 mmol) and DIPEA (0.21 mL, 1.18 mmol) in DCM (1 mL) was cooled to 0° C. before crude 2-chloro-benzo-

| | | LC-MS | |
|---|---|---|---|
| Intermediate | Name | $t_R$ [min] | [M + H]⁺ |
| D2 | 2-Morpholin-4-yl-benzothiazol-5-ylamine | 0.46 | 236.16 |
| D3 | 2-(4-Methyl-piperazin-1-yl)-benzothiazol-5-ylamine | 0.27 | 249.19 |
| D4 | 2-Pyrrolidin-1-yl-benzothiazol-5-ylamine | 0.48 | 220.11 |
| D5 | N2,N2-Diethyl-benzothiazole-2,5-diamine | 0.52 | 222.13 |
| D6 | N2,N2-Dimethyl-benzothiazole-2,5-diamine | 0.42 | 194.12 |
| D7 | 2-(3,3-Difluoro-azetidin-1-yl)-benzothiazol-5-ylamine | 0.52 | 241.95 |
| D8 | 2-(3,3-Difluoro-pyrrolidin-1-yl)-benzothiazol-5-ylamine | 0.54 | 256.10 |
| D9 | 2-(3,3-Difluoro-piperidin-1-yl)-benzothiazol-5-ylamine | 0.57 | 270.10 |
| D10 | 2-(6-Oxa-1-aza-spiro[3.3]hept-1-yl)-benzothiazol-5-ylamine | 0.47 | 248.12 |
| D11 | 2-(2-Oxa-6-aza-spiro[3.3]hept-6-yl)-benzothiazol-5-ylamine | 0.45 | 248.12 |
| D12 | 2-(1,1-Dioxo-1l6-thiomorpholin-4-yl)-benzothiazol-5-ylamine | 0.43 | 284.04 |
| D13 | N2-(2-Dimethylamino-ethyl)-N2-methyl-benzothiazole-2,5-diamine | 0.33 | 251.15 |
| D14 | 2-(3-Methoxy-pyrrolidin-1-yl)-benzothiazol-5-ylamine | 0.48 | 250.12 |
| D15 | 2-(4-Methoxy-piperidin-1-yl)-benzothiazol-5-ylamine | 0.52 | 264.15 |
| D16 | 1-(5-Amino-benzothiazol-2-yl)-3-methyl-azetidin-3-ol | 0.44 | 236.11 |
| D17 | 2-(4-Dimethylamino-piperidin-1-yl)-benzothiazol-5-ylamine | 0.35 | 277.14 | thiazole-5-carbonyl chloride (92 mg, 0.237 mmol) dissolved in DCM (1 mL) was added. The mixture was stirred at rt for 30 min. The mixture was diluted with DCM (5 mL) and washed with water (5 mL). the organic extract was dried over $Na_2SO_4$, filtered and concentrated to give the crude title compound (69 mg) as a pale yellow resin; LC-MS: $t_R$=0.86 min; $[M+H]^+$=330.97; $^1$H NMR (400 MHz, $D_6$-DMSO): δ 10.28 (s, 1H), 8.56 (d, J=1.1 Hz, 1H), 8.26 (d, J=8.5 Hz, 1H), 8.07 (dd, $J_1$=1.5 Hz, $J_2$=8.5 Hz, 1H), 7.70 (s, 1H), 7.45 (dd, $J_1$=1.7 Hz, $J_2$=8.5 Hz, 1H), 6.76 (d, J=8.5 Hz, 1H), 4.54 (t, J=8.7 Hz, 2H), 3.21 (t, J=8.7 Hz, 2H).

Intermediate E3

N-Benzo[d][1,3]dioxol-5-yl)-2-chlorobenzo[d]thiazole-5-carboxamide

The title compound was prepared in analogy to Intermediate E2; LC-MS: $t_R$=0.86 min; [M+H]=332.98; $^1$H NMR (400 MHz, $D_6$-DMSO): δ 10.34 (s, 1H), 8.56 (d, J=1.3 Hz, 1H), 8.27 (d, J=8.5 Hz, 1H), 8.06 (dd, $J_1$=1.6 Hz, $J_2$=8.5 Hz, 1H), 7.48 (d, J=1.9 Hz, 1H), 7.23 (dd, $J_1$=2.0 Hz, $J_2$=8.4 Hz, 1H), 6.93 (d, J=8.4 Hz, 1H), 6.03 (s, 2H).

Intermediate E4

2-Chloro-N-(2,3-dihydrobenzo[b][1,4]dioxin-6-yl) benzo[d]thiazole-5-carboxamide

The title compound was prepared in analogy to Intermediate E2; LC-MS: $t_R$=0.87 min; $[M+H]^+$=346.90; $^1$H NMR (400 MHz, $D_6$-DMSO): δ 10.28 (s, 1H), 8.56 (d, J=1.4 Hz, 1H), 8.26 (d, J=8.5 Hz, 1H), 8.06 (dd, $J_1$=1.6 Hz, $J_2$=8.5 Hz, 1H), 7.43 (d, J=2.4 Hz, 1H), 7.24 (dd, $J_1$=2.4 Hz, $J_2$=8.8 Hz, 1H), 6.85 (d, J=8.7 Hz, 1H), 4.19-4.32 (m, 4H).

Example 1

2,3-Dihydro-benzofuran-5-carboxylic acid [2-(1,1-dioxo-1l6-thiomorpholin-4-yl)-benzooxazol-5-yl]-amide To a solution of 2,3-dihydrobenzo[b]furan-5-carboxylic acid (18.5 mg, 113 μmol) in DCM (2 mL) 1-chloro-N,N-2-trimethylpropenylamine (17 μL, 124 μmol) was added. The mixture was stirred at rt for 15 min before DIPEA (96 μL, 563 μmol) and 4-(5-aminobenzo[d]oxazol-2-yl)thiomorpholine 1,1-dioxide (30.1 mg, 113 mmol) was added. Stirring was continued at rt for 30 min. The mixture was diluted with DMF (2 mL) and separated using prep. HPLC (column: XBridge Prep C18, 30×75 mm, 10 μm, gradient of MeCN in water containing 0.5% of 15 M aq. $NH_4OH$) to give the title compound (30 mg) as a white solid; LC-MS: $t_R$=0.73 min; $[M+H]^+$=414.05; $^1$H NMR (400 MHz, $D_6$-DMSO) δ: 10.03 (s, 1H), 7.88 (s, 1H), 7.77-7.82 (m, 2H), 7.38-7.46 (m, 2H), 6.88 (d, J=8.4 Hz, 1H), 4.64 (t, J=8.8 Hz, 2H), 4.04-4.11 (m, 4H), 3.32-3.39 (m, 4H), 3.26 (t, J=8.7 Hz, 2H).

Examples 2 to 41

The following Example compounds were prepared in analogy to Example 1 starting from the appropriate Intermediates A2 to A39 and 2,3-dihydrobenzo[b][1,4]dioxine-6-carboxylic acid, 2,3-dihydrobenzofuran-5-carboxylic acid, 4-methyl-3,4-dihydro-2H-benzo[b][1,4]oxazine-6-carboxylic acid, benzo[d][1,3]dioxole-5-carboxylic acid, or chromane-6-carboxylic acid.

| | | LC-MS | |
|---|---|---|---|
| Example | Name | $t_R$ [min] | $[M + H]^+$ |
| 2 | 2,3-Dihydro-benzofuran-5-carboxylic acid (2-piperidin-1-yl-benzooxazol-5-yl)-amide | 0.78 | 364.26 |
| 3 | 2,3-Dihydro-benzofuran-5-carboxylic acid (2-pyrrolidin-1-yl-benzooxazol-5-yl)-amide | 0.71 | 350.29 |
| 4 | 2,3-Dihydro-benzofuran-5-carboxylic acid [2-(4-methyl-piperazin-1-yl)-benzooxazol-5-yl]-amide | 0.59 | 379.23 |
| 5 | 2,3-Dihydro-benzofuran-5-carboxylic acid (2-morpholin-4-yl-benzooxazol-5-yl)-amide | 0.76 | 366.25 |
| 6 | 2,3-Dihydro-benzofuran-5-carboxylic acid (2-diethylamino-benzooxazol-5-yl)-amide | 0.75 | 352.29 |
| 7 | 2,3-Dihydro-benzofuran-5-carboxylic acid [2-(4,4-difluoro-piperidin-1-yl)-benzooxazol-5-yl]-amide | 0.86 | 400.20 |
| 8 | 2,3-Dihydro-benzofuran-5-carboxylic acid [2-(3,3-difluoro-azetidin-1-yl)-benzooxazol-5-yl]-amide | 0.82 | 372.10 |
| 9 | 2,3-Dihydro-benzofuran-5-carboxylic acid [2-(3,3-difluoro-pyrrolidin-1-yl)-benzooxazol-5-yl]-amide | 0.93 | 386.04 |
| 10 | 2,3-Dihydro-benzofuran-5-carboxylic acid [2-(3-methoxy-pyrrolidin-1-yl)-benzooxazol-5-yl]-amide | 0.84 | 380.04 |
| 11 | 2,3-Dihydro-benzofuran-5-carboxylic acid [2-(4-methoxy-piperidin-1-yl)-benzooxazol-5-yl]-amide | 0.89 | 394.09 |
| 12 | 2,3-Dihydro-benzofuran-5-carboxylic acid [2-(3-hydroxy-3-methyl-azetidin-1-yl)-benzooxazol-5-yl]-amide | 0.78 | 366.04 |
| 13 | 2,3-Dihydro-benzofuran-5-carboxylic acid {2-[(2-dimethylamino-ethyl)-methyl-amino]-benzooxazol-5-yl}-amide; compound with formic acid | 0.60 | 381.08 |
| 14 | 2,3-Dihydro-benzofuran-5-carboxylic acid [2-(4-dimethylamino-piperidin-1-yl)-benzooxazol-5-yl]-amide; compound with formic acid | 0.78 | 406.95 |
| 15 | 2,3-Dihydro-benzofuran-5-carboxylic acid [2-(6-oxa-1-aza-spiro[3.3]hept-1-yl)-benzooxazol-5-yl]-amide | 0.75 | 378.23 |
| 16 | 2,3-Dihydro-benzofuran-5-carboxylic acid [2-(3,3-difluoro-pipeiidin-1-yl)-benzooxazol-5-yl]-amide | 0.85 | 400.21 |
| 17 | 2,3-Dihydro-benzofuran-5-carboxylic acid [2-(3-morpholin-4-yl-azetidin-1-yl)-benzooxazol-5-yl]-amide | 0.59 | 421.02 |
| 18 | 2,3-Dihydro-benzofuran-5-carboxylic acid {2-[methyl-(3-methyl-oxetan-3-yl)-amino]-benzooxazol-5-yl}-amide | 0.78 | 380.20 |

| Example | Name | LC-MS $t_R$ [min] | $[M + H]^+$ |
|---|---|---|---|
| 19 | 2,3-Dihydro-benzofuran-5-carboxylic acid {2-[3-(1,1-dioxo-1l6-thiomoipholin-4-yl)-azetidin-1-yl]-benzooxazol-5-yl}-amide | 0.70 | 469.10 |
| 20 | 2,3-Dihydro-benzofuran-5-carboxylic acid [2-(3-hydroxy-3-methyl-[1,3']biazetidinyl-1'-yl)-benzooxazol-5-yl]-amide | 0.61 | 421.20 |
| 21 | 2,3-Dihydro-benzofuran-5-carboxylic acid [2-(1-oxa-6-aza-spiro[3.3]hept-6-yl)-benzooxazol-5-yl]-amide | 0.74 | 378.20 |
| 22 | 2,3-Dihydro-benzofuran-5-carboxylic acid [2-(2-oxa-6-aza-spiro[3.4]oct-6-yl)-benzooxazol-5-yl]-amide | 0.70 | 392.20 |
| 23 | 2,3-Dihydro-benzofuran-5-carboxylic acid [2-(6-oxa-2-aza-spiro[3.5]non-2-yl)-benzooxazol-5-yl]-amide | 0.77 | 406.11 |
| 24 | 2,3-Dihydro-benzofuran-5-carboxylic acid [2-(2-oxa-5-aza-spiro[3.4]oct-5-yl)-benzooxazol-5-yl]-amide | 0.76 | 392.11 |
| 25 | 2,3-Dihydro-benzofuran-5-carboxylic acid [2-(1-oxa-6-aza-spiro[3.5]non-6-yl)-benzooxazol-5-yl]-amide | 0.75 | 406.11 |
| 26 | 2,3-Dihydro-benzofuran-5-carboxylic acid [2-(2-oxa-5-aza-spiro[3.5]non-5-yl)-benzooxazol-5-yl]-amide | 0.84 | 406.12 |
| 27 | 2,3-Dihydro-benzofuran-5-carboxylic acid [2-(1-oxa-7-aza-spiro[3.5]non-7-yl)-benzooxazol-5-yl]-amide | 0.76 | 406.09 |
| 28 | 2,3-Dihydro-benzofuran-5-carboxylic acid [2-(1-oxa-7-aza-spiro[3.5]non-7-yl)-benzooxazol-5-yl]-amide | 0.73 | 420.13 |
| 29 | 2,3-Dihydro-benzofuran-5-carboxylic acid [2-(1-oxa-8-aza-spiro[4.5]dec-8-yl)-benzooxazol-5-yl]-amide | 0.80 | 420.12 |
| 30 | 2,3-Dihydro-benzofuran-5-carboxylic acid [2-(7-oxa-2-aza-spiro[3.5]non-2-yl)-benzooxazol-5-yl]-amide | 0.76 | 406.11 |
| 31 | 2,3-Dihydro-benzofuran-5-carboxylic acid [2-(5-oxa-2-aza-spiro[3.4]oct-2-yl)-benzooxazol-5-yl]-amide | 0.78 | 392.11 |
| 32 | 2,3-Dihydro-benzofuran-5-carboxylic acid {2-[3-(4-hydroxy-piperidin-1-yl)-azetidin-1-yl]-benzooxazol-5-yl}-amide | 0.58 | 435.15 |
| 33 | 2,3-Dihydro-benzofuran-5-carboxylic acid [2-(6-methyl-2,6-diaza-spiro[3.5]non-2-yl)-benzooxazol-5-yl]-amide | 0.61 | 419.14 |
| 34 | 2,3-Dihydro-benzofuran-5-carboxylic acid [2-(5-oxa-2-aza-spiro[3.5]non-2-yl)-benzooxazol-5-yl]-amide | 0.82 | 406.12 |
| 35 | 2,3-Dihydro-benzofuran-5-carboxylic acid [2-(1-aza-spiro[3.3]hept-1-yl)-benzooxazol-5-yl]-amide | 0.83 | 376.10 |
| 36 | 2,3-Dihydro-benzofuran-5-carboxylic acid [2-(7-oxa-1-aza-spiro[3.5]non-1-yl)-benzooxazol-5-yl]-amide | 0.75 | 406.11 |
| 37 | 1-{5-[(2,3-Dihydro-benzofuran-5-carbonyl)-amino]-benzooxazol-2-yl}-azetidine-3-carboxylic acid tert-butyl ester | 0.88 | 436.11 |
| 38 | 2,3-Dihydro-benzofuran-5-carboxylic acid [2-(2-oxo-pyrrolidin-1-yl)-benzooxazol-5-yl]-amide | 0.66 | 364.15 |
| 39 | 2,3-Dihydro-benzo[1,4]dioxine-6-carboxylic acid [2-(1,1-dioxo-thiomorpholin-4-yl)-benzooxazol-5-yl]-amide | 0.73 | 429.90 |
| 40 | Chroman-6-carboxylic acid [2-(1,1-dioxo-thiomorpholin-4-yl)-benzooxazol-5-yl]-amide | 0.77 | 427.97 |
| 41 | 4-Methyl-3,4-dihydro-2H-benzo[1,4]oxazine-6-carboxylic acid [2-(1,1-dioxo-thiomorpholin-4-yl)-benzooxazol-5-yl]-amide | 0.75 | 442.94 |

Example 3: $^1$H NMR (400 MHz, D$_6$-DMSO) δ: 10.01 (s, 1H), 7.83 (s, 1H), 7.74 (d, J=8.8 Hz, 1H), 7.64 (s, 1H), 7.27-7.33 (m, 2H), 6.85 (d, J=8.1 Hz, 1H), 4.60 (t, J=8.8 Hz, 2H), 3.50-3.55 (m, 4H), 3.23 (t, J=8.3 Hz, 2H), 1.91-1.99 (m, 4H).

Example 5: $^1$H NMR (400 MHz, D$_6$-DMSO) δ: 10.04 (s, 1H), 7.84 (s, 1H), 7.75 (d, J=8.2 Hz, 1H), 7.71 (s, 1H), 7.35 (s, 2H), 6.85 (dd, J$_1$=2.2 Hz, J$_2$=8.3 Hz, 1H), 4.56-4.65 (m, 2H), 3.51-3.69 (m, 8H), 3.19-3.27 (m, 2H).

Example 6: $^1$H NMR (400 MHz, D$_6$-DMSO) δ: 10.01 (s, 1H), 7.83 (s, 1H), 7.75 (d, J=8.6 Hz, 1H), 7.63 (s, 1H), 7.23-7.33 (m, 2H), 6.85 (d, J=8.3 Hz, 1H), 4.60 (t, J=8.7 Hz, 2H), 3.50 (q, J=6.7 Hz, 4H), 3.23 (t, J=8.6 Hz, 2H), 1.18 (t, J=6.9 Hz, 6H).

Example 15: $^1$H NMR (400 MHz, DMSO) δ: 10.04 (s, 1H), 7.89 (s, 1H), 7.78-7.83 (m, 2H), 7.43 (s, 2H), 6.89 (d, J=8.4 Hz, 1H), 5.22 (d, J=7.5 Hz, 2H), 4.61-4.69 (m, 4H), 4.02 (t, J=7.3 Hz, 2H), 3.27 (t, J=8.7 Hz, 2H), 2.73 (t, J=7.2 Hz, 2H).

Example 23: $^1$H NMR (400 MHz, DMSO) δ5:10.02 (s, 1H), 7.89 (s, 1H), 7.80 (d, J=8.3 Hz, 1H), 7.76 (d, J=1.2 Hz, 1H), 7.34-7.43 (m, 2H), 6.89 (d, J=8.4 Hz, 1H), 4.65 (t, J=8.7 Hz, 2H), 3.87-3.95 (m, 4H), 3.68 (s, 2H), 3.51-3.56 (m, 2H), 3.27 (t, J=8.6 Hz, 2H), 1.84-1.91 (m, 2H), 1.50-1.58 (m, 2H).

Example 26: $^1$H NMR (400 MHz, DMSO) δ: 10.05 (s, 1H), 7.88 (s, 1H), 7.76-7.81 (m, 2H), 7.40 (s, 2H), 6.89 (d, J=8.4 Hz, 1H), 4.79-4.84 (m, 2H), 4.64 (t, J=8.7 Hz, 2H), 4.43-4.48 (m, 2H), 3.27 (t, J=8.7 Hz, 2H), 2.02-2.09 (m, 2H), 1.69-1.77 (m, 2H), 1.39-1.47 (m, 2H).

Example 30: $^1$H NMR (400 MHz, DMSO) δ: 10.01 (s, 1H), 7.89 (s, 1H), 7.80 (d, J=8.4 Hz, 1H), 7.76 (d, J=1.2 Hz, 1H), 7.34-7.43 (m, 2H), 6.89 (d, J=8.4 Hz, 1H), 4.65 (t, J=8.7 Hz, 2H), 3.98 (s, 4H), 3.53-3.60 (m, 2H), 3.27 (t, J=8.7 Hz, 2H), 1.76-1.84 (m, 4H).

Example 34: $^1$H NMR (400 MHz, CDCl$_3$) δ: 7.82 (s, 1H), 7.80 (s, 1H), 7.68 (dd, J$_1$=1.4 Hz, J$_2$=8.3 Hz, 1H), 7.53 (d, J=1.9 Hz, 1H), 7.43 (dd, J$_1$=2.0 Hz, J$_2$=8.6 Hz, 1H), 7.25 (d, J=8.6 Hz, 1H), 6.85 (d, J=8.3 Hz, 1H), 4.68 (t, J=8.8 Hz, 2H), 4.21 (d, J=8.7 Hz, 2H), 4.11 (d, J=8.7 Hz, 2H), 3.69-3.73 (m, 2H), 3.29 (t, J=8.7 Hz, 2H), 1.86-1.92 (m, 2H), 1.68-1.75 (m, 2H), 1.57-1.64 (m, 2H).

Example 39: ¹H NMR (400 MHz, DMSO) δ: 10.06 (s, 1H), 7.77 (s, 1H), 7.47-7.53 (m, 2H), 7.40 (s, 2H), 6.98 (d, J=8.3 Hz, 1H), 4.26-4.35 (m, 4H), 4.03-4.11 (m, 4H), 3.30-3.37 (m, 4H).

Example 41: ¹H NMR (400 MHz, DMSO) δ: 9.99 (s, 1H), 7.77 (s, 1H), 7.39 (s, 2H), 7.23-7.29 (m, 2H), 6.77 (d, J=8.8 Hz, 1H), 4.26-4.33 (m, 2H), 4.03-4.11 (m, 4H), 3.30-3.37 (m, 4H), 3.24-3.30 (m, 4H), 2.90 (s, 3H).

Example 37

1-{5-[(2,3-Dihydro-benzofuran-5-carbonyl)-amino]-benzooxazol-2-yl}-azetidine-3-carboxylic acid tert-butyl ester To a solution of 2,3-dihydrobenzofuran-5-carboxylic acid (10 mg, 63 µmol) and HBTU (24 mg, 63 µmol) in DMF (1 mL) DIPEA (33 µL, 190 mol) was added. The mixtures were stirred at rt for 30 min before by tert-butyl 1-(5-aminobenzo[d]oxazol-2-yl)azetidine-3-carboxylate (18 mg, 63 µmol) was added. Stirring was continued at 55° C. for 16 h. The mixture was separated by prep. HPLC to give 1-{5-[(2,3-dihydro-benzofuran-5-carbonyl)-amino]-benzooxazol-2-yl}-azetidine-3-carboxylic acid tert-butyl ester (4 mg) as a colourless resin; LC-MS: $t_R$=0.88 min; [M+H]⁺=436.11.

Example 42

(R)—N-(2-(3-hydroxypiperidin-1-yl)benzo[d]oxazol-5-yl)-2,3-dihydrobenzofuran-5-carboxamide To a mixture of N-(2-mercaptobenzo[d]oxazol-5-yl)-2,3-dihydrobenzofuran-5-carboxamide (Intermediate B1) (20 mg, 64 µmol) in DCM (1 mL) and SOCl₂ (0.1 mL) DMF (20 µL) was added. The suspension was stirred at rt for 1 h before the solvent was removed in vacuo to give crude N-(2-chlorobenzo[d]oxazol-5-yl)-2,3-dihydrobenzofuran-5-carboxamid; LC-MS: $t_R$=0.85 min; [M+H]⁺=314.96. To this material a solution of (R)-piperidin-3-ol (7.8 mg, 77 µmol) in DMF (0.8 mL) and K₂CO₃ (27 mg, 192 µmol) was added. The mixture was stirred at 70° C. for 16 h before it was cooled to rt and separated by prep. HPLC to give the title compound (7 mg) as a colourless resin; LC-MS: $t_R$=0.68 min; [M+H]⁺=380.15; ¹H NMR (400 MHz, DMSO) δ: 9.99 (s, 1H), 7.86 (s, 1H), 7.77 (d, J=8.3 Hz, 1H), 7.69 (s, 1H), 7.30-7.36 (m, 2H), 6.87 (d, J=8.3 Hz, 1H), 5.06 (d, J=4.0 Hz, 1H), 4.63 (t, J=8.6 Hz, 2H), 3.88 (dd, $J_1$=3.4 Hz, $J_2$=13.0 Hz, 1H), 3.73-3.79 (m, 1H), 3.59-3.65 (m, 1H), 3.29-.3.36 (m, 1H), 3.25 (t, J=8.8 Hz, 2H), 3.14 (dd, $J_1$=8.1 Hz, $J_2$=12.5 Hz, 1H), 1.79-1.90 (m, 2H), 1.37-1.54 (m, 2H).

Examples 43 TO 74

The following Example compounds were prepared in analogy to Example 42 starting from Intermediate B1 and the appropriate amines.

| | | LC-MS | |
|---|---|---|---|
| Example | Name | $t_R$ [min] | [M + H]⁺ |
| 43 | 2,3-Dihydro-benzofuran-5-carboxylic acid [2-((S)-3-hydroxy-piperidin-1-yl)-benzooxazol-5-yl]-amide | 0.74 | 380.08 |
| 44 | 2,3-Dihydro-benzofuran-5-carboxylic acid [2-(3-isopropoxy-azetidin-1-yl)-benzooxazol-5-yl]-amide | 0.94 | 394.05 |
| 45 | 2,3-Dihydro-benzofuran-5-carboxylic acid [2-((R)-3-hydroxy-pyrrolidin-1-yl)-benzooxazol-5-yl]-amide | 0.63 | 366.20 |
| 46 | 2,3-Dihydro-benzofuran-5-carboxylic acid [2-((S)-3-hydroxy-pyirolidin-1-yl)-benzooxazol-5-yl]-amide | 0.71 | 365.76 |
| 47 | 2,3-Dihydro-benzofuran-5-carboxylic acid [2-(3-hydroxy-azetidin-1-yl)-benzooxazol-5-yl]-amide | 0.70 | 352.03 |
| 48 | 2,3-Dihydro-benzofuran-5-carboxylic acid [2-(4-hydroxy-piperidin-1-yl)-benzooxazol-5-yl]-amide | 0.73 | 380.02 |
| 49 | 2,3-Dihydro-benzofuran-5-carboxylic acid [2-(3-phenyl-azetidin-1-yl)-benzooxazol-5-yl]-amide | 1.02 | 411.94 |
| 50 | 2,3-Dihydro-benzofuran-5-carboxylic acid [2-(2-oxa-7-aza-spiro[3.5]non-7-yl)-benzooxazol-5-yl]-amide | 0.81 | 405.99 |
| 51 | 2,3-Dihydro-benzofuran-5-carboxylic acid [2-(2-ethoxymethyl-pyrrolidin-1-yl)-benzooxazol-5-yl]-amide | 1.02 | 408.02 |
| 52 | 2,3-Dihydro-benzofuran-5-carboxylic acid {2-[(3-fluoro-oxetan-3-ylmethyl)-methyl-amino]-benzooxazol-5-yl}-amide | 0.82 | 397.73 |
| 53 | 2,3-Dihydro-benzofuran-5-carboxylic acid [2-(4-oxetan-3-yl-piperazin-1-yl)-benzooxazol-5-yl]-amide | 0.59 | 421.18 |
| 54 | 2,3-Dihydro-benzofuran-5-carboxylic acid {2-[methyl-(1-oxetan-3-yl-piperidin-4-yl)-amino]-benzooxazol-5-yl}-amide | 0.74 | 448.93 |
| 55 | 2,3-Dihydro-benzofuran-5-carboxylic acid [2-(2-oxa-6-aza-spiro[3.5]non-6-yl)-benzooxazol-5-yl]-amide | 0.78 | 405.94 |
| 56 | 2,3-Dihydro-benzofuran-5-carboxylic acid [2-(methyl-oxetan-3-ylmethyl-amino)-benzooxazol-5-yl]-amide | 0.77 | 379.94 |
| 57 | 2,3-Dihydro-benzofuran-5-carboxylic acid [2-(methyl-oxetan-3-yl-amino)-benzooxazol-5-yl]-amide | 0.77 | 365.71 |
| 58 | 2,3-Dihydro-benzofuran-5-carboxylic acid [2-(2-methoxymethyl-pyirolidin-1-yl)-benzooxazol-5-yl]-amide | 0.95 | 393.95 |
| 59 | 2,3-Dihydro-benzofuran-5-carboxylic acid [2-(3-methoxy-piperidin-1-yl)-benzooxazol-5-yl]-amide | 0.87 | 393.98 |
| 60 | 2,3-Dihydro-benzofuran-5-carboxylic acid [2-(3-dimethylaminomethyl-pyrrolidin-1-yl)-benzooxazol-5-yl]-amide | 0.86 | 407.04 |
| 61 | 2,3-Dihydro-benzofuran-5-carboxylic acid [2-(2-dimethylaminomethyl-pyrrolidin-1-yl)-benzooxazol-5-yl]-amide | 0.66 | 407.24 |
| 62 | rac-2,3-Dihydro-benzofuran-5-carboxylic acid [2-(2-phenyl-azetidin-1-yl)-benzooxazol-5-yl]-amide | 0.96 | 412.01 |

| Example | Name | LC-MS | |
|---|---|---|---|
| | | $t_R$ [min] | [M + H]$^+$ |
| 63 | 2,3-Dihydro-benzofuran-5-carboxylic acid [2-(cyclopropyl-oxetan-3-yl-amino)-benzooxazol-5-yl]-amide | 0.82 | 391.99 |
| 64 | 2,3-Dihydro-benzofuran-5-carboxylic acid [2-(3-pyrrolidin-1-yl-azetidin-1-yl)-benzooxazol-5-yl]-amide | 0.78 | 405.02 |
| 65 | 2,3-Dihydro-benzofuran-5-carboxylic acid {2-[3-(1-hydroxy-1-methyl-ethyl)-azetidin-1-yl]-benzooxazol-5-yl}-amide | 0.76 | 393.80 |
| 66 | 2,3-Dihydro-benzofuran-5-carboxylic acid [2-(3-dimethylaminomethyl-azetidin-1-yl)-benzooxazol-5-yl]-amide | 0.76 | 392.93 |
| 67 | 2,3-Dihydro-benzofuran-5-carboxylic acid [2-(7-methyl-1,7-diaza-spiro[3.5]non-1-yl)-benzooxazol-5-yl]-amide | 0.62 | 419.15 |
| 68 | 2,3-Dihydro-benzofuran-5-carboxylic acid [2-(7-methyl-2,7-diaza-spiro[3.5]non-2-yl)-benzooxazol-5-yl]-amide | 0.77 | 419.03 |
| 69 | 2,3-Dihydro-benzofuran-5-carboxylic acid [2-(3-dimethylamino-azetidin-1-yl)-benzooxazol-5-yl]-amide | 0.78 | 379.01 |
| 70 | 2,3-Dihydro-benzofuran-5-carboxylic acid [2-(2,2-dioxo-2l6-thia-6-aza-spiro[3.3]hept-6-yl)-benzooxazol-5-yl]-amide | 0.76 | 425.87 |
| 71 | 2,3-Dihydro-benzofuran-5-carboxylic acid [2-(6-oxa-1-aza-spiro[3.4]oct-1-yl)-benzooxazol-5-yl]-amide | 0.80 | 391.99 |
| 72 | 2,3-Dihydro-benzofuran-5-carboxylic acid [2(1,1-dioxo-1l6-thia-6-aza-spiro[3.3]hept-6-yl)-benzooxazol-5-yl]-amide | 0.75 | 425.90 |
| 73 | 2,3-Dihydro-benzofuran-5-carboxylic acid [2-(3-dimethylamino-3-methyl-azetidin-1-yl)-benzooxazol-5-yl]-amide | 0.81 | 393.02 |
| 74 | 2,3-Dihydro-benzofuran-5-carboxylic acid [2-(6-oxa-2-aza-spiro[3.4]oct-2-yl)-benzooxazol-5-yl]-amide | 0.77 | 391.95 |

Example 44: $^1$H NMR (400 MHz, DMSO) δ: 10.02 (s, 1H), 7.86 (s, 1H), 7.77 (dd, $J_1$=1.2 Hz, $J_2$=8.3 Hz, 1H), 7.74 (d, J=1.2 Hz, 1H), 7.38 (dd, $J_1$=1.7 Hz, $J_2$=8.8 Hz, 1H), 7.35 (d, J=8.6 Hz, 1H), 6.87 (d, J=8.3 Hz, 1H), 4.63 (t, J=8.7 Hz, 2H), 4.52-4.58 (m, 1H), 4.38-4.44 (m, 2H), 3.99 (dd, $J_1$=4.6 Hz, $J_2$=9.0 Hz, 2H), 3.65 (hept, J=6.6 Hz, 1H), 3.25 (t, J=8.6 Hz, 2H), 1.11 (d, J=6.1 Hz, 6H).

Example 47: $^1$H NMR (400 MHz, DMSO) δ: 10.01 (s, 1H), 7.86 (s, 1H), 7.77 (d, J=8.3 Hz, 1H), 7.73 (d, J=0.7 Hz, 1H), 7.32-7.40 (m, 2H), 6.87 (d, J=8.3 Hz, 1H), 5.93 (d, J=6.8 Hz, 1H), 4.59-4.66 (m, 3H), 4.38 (t, J=7.8 Hz, 2H), 3.95 (dd, $J_1$=4.6 Hz, $J_2$=8.6 Hz, 2H), 3.25 (t, J=8.6 Hz, 2H).

Example 50: $^1$H NMR (400 MHz, DMSO) δ: 10.00 (s, 1H), 7.86 (s, 1H), 7.77 (dd, $J_1$=0.7 Hz, $J_2$=8.3 Hz, 1H), 7.70 (s, 1H), 7.30-7.37 (m, 2H), 6.87 (d, J=8.3 Hz, 1H), 4.62 (t, J=8.8 Hz, 2H), 4.36 (s, 4H), 3.52-3.57 (m, 2H), 3.25 (t, J=8.8 Hz, 2H), 1.85-1.91 (m, 4H).

Example 57: $^1$H NMR (400 MHz, DMSO) δ: 10.02 (s, 1H), 7.86 (s, 1H), 7.77 (d, J=8.6 Hz, 1H), 7.73 (s, 1H), 7.30-7.40 (m, 2H), 6.87 (d, J=8.3 Hz, 1H), 5.25 (quint, J=6.8 Hz, 1H), 4.76-4.83 (m, 4H), 4.62 (t, J=8.6 Hz, 2H), 3.25 (t, J=8.6 Hz, 2H), 3.23 (s, 3H).

Example 70: $^1$H NMR (400 MHz, DMSO) δ: 10.03 (s, 1H), 7.87 (s, 1H), 7.76-7.80 (m, 2H), 7.36-7.44 (m, 2H), 6.87 (d, J=8.3 Hz, 1H), 4.63 (t, J=8.6 Hz, 2H), 4.54 (s, 4H), 4.45 (s, 4H), 3.25 (t, J=8.8 Hz, 2H).

Example 71: $^1$H NMR (400 MHz, DMSO) δ: 10.01 (s, 1H), 7.87 (s, 1H), 7.78 (dd, $J_1$=1.0 Hz, $J_2$=8.3 Hz, 1H), 7.74 (s, 1H), 7.33-7.41 (m, 2H), 6.87 (d, J=8.4 Hz, 1H), 4.63 (t, J=8.7 Hz, 2H), 3.98-4.12 (m, 4H), 3.77-3.88 (m, 2H), 3.26 (t, J=9.0 Hz, 2H), 2.54-2.64 (m, 2H), 2.09-2.20 (m, 2H).

Example 72: $^1$H NMR (400 MHz, DMSO) δ5:10.06 (s, 1H), 7.87 (s, 1H), 7.85 (s, 1H), 7.78 (d, J=8.3 Hz), 7.38-7.46 (m, 2H), 6.88 (d, J=8.4 Hz, 1H), 5.03-5.11 (m, 2H), 4.63 (t, J=8.6 Hz, 2H), 4.44-4.52 (m, 2H), 4.13-4.19 (m, 2H), 3.26 (t, J=8.6 Hz, 2H), 2.89 (t, J=6.8 Hz, 2H).

Example 75

2-(4-Methyl-piperazin-1-yl)-benzooxazole-5-carboxylic acid (2,3-dihydro-benzofuran-5-yl)-amide To a solution of 2-(4-methylpiperazin-1-yl)benzo[d]oxazole-5-carboxylic acid (45 mg, 172 µmol) and 5-amino-2,3-dihydrobenzofuran (47 mg, 344 µmol) in DCM (2 mL) and pyridine (0.14 mL) POCl$_3$ (17 µL, 189 µmol) was added. The mixture was stirred at rt for 30 min before it was concentrated. The residue was dissolved in acetonitrile (1 mL) and separated by prep. HPLC to give the title compound (35 mg) as a beige solid; LC-MS: $t_R$=0.57 min; [M+H]$^+$=379.19; $^1$H NMR (400 MHz, CDCl$_3$) δ: 7.81 (s, 1H), 7.75 (s, 1H), 7.67 (s, 1H), 7.62 (d, J=8.3 Hz, 1H), 7.33 (d, J=8.3 Hz, 1H), 7.16 (dd, $J_1$=0.7 Hz, $J_2$=8.2 Hz, 1H), 6.78 (d, J=8.5 Hz, 1H), 4.61 (t, J=8.7 Hz, 2H), 3.76-3.85 (m, 4H), 3.25 (t, J=8.7 Hz, 2H), 2.56-2.66 (m, 4H), 2.41 (s, 3H).

Examples 76 TO 80

The following Example compounds were prepared in analogy to Example 75 starting from Intermediates C2 to C6 and 5-amino-2,3-dihydrobenzofuran.

| Example | Name | LC-MS | |
|---|---|---|---|
| | | $t_R$ [min] | [M + H]$^+$ |
| 76 | 2-Piperidin-1-yl-benzooxazole-5-carboxylic acid (2,3-dihydro-benzofuran-5-yl)-amide | 0.84 | 364.01 |
| 77 | 2-Morpholin-4-yl-benzooxazole-5-carboxylic acid (2,3-dihydro-benzofuran-5-yl)-amide | 0.76 | 366.14 |
| 78 | 2-Diethylamino-benzooxazole-5-carboxylic acid (2,3-dihydro-benzofuran-5-yl)-amide | 0.81 | 352.05 |

-continued

| Example | Name | LC-MS $t_R$ [min] | [M + H]⁺ |
|---|---|---|---|
| 79 | 2-Pyrrolidin-1-yl-benzooxazole-5-carboxylic acid (2,3-dihydro-benzofuran-5-yl)-amide | 0.76 | 350.02 |
| 80 | 2-(6-Oxa-1-aza-spiro[3.3]hept-1-yl)-benzooxazole-5-carboxylic acid (2,3-dihydro-benzofuran-5-yl)-amide | 0.75 | 377.98 |

Example 76: ¹H NMR (400 MHz, CDCl₃) δ: 7.81 (s, 2H), 7.67 (s, 1H), 7.63 (d, J=8.3 Hz, 1H), 7.32 (d, J=8.3 Hz, 1H), 7.17 (dd, J₁=1.5 Hz, J₂=8.3 Hz, 1H), 6.78 (d, J=8.5 Hz, 1H), 4.61 (t, J=8.7 Hz, 2H), 3.69-3.77 (m, 4H), 3.26 (t, J=8.7 Hz, 2H), 1.70-1.78 (m, 6H).

Example 77: ¹H NMR (400 MHz, CDCl₃) δ: 7.84 (s, 1H), 7.75 (s, 1H), 7.63-7.69 (m, 2H), 7.36 (d, J=8.3 Hz, 1H), 7.16 (dd, J₁=1.1 Hz, J₂=8.4 Hz, 1H), 6.79 (d, J=8.4 Hz, 1H), 4.61 (t, J=8.7 Hz, 2H), 3.84-3.89 (m, 4H), 3.73-3.79 (m, 4H), 3.26 (t, J=8.7 Hz, 2H).

Example 78: ¹H NMR (400 MHz, CDCl₃) δ: 7.80 (d, J=0.8 Hz, 1H), 7.75 (s, 1H), 7.68 (s, 1H), 7.60 (dd, J₁=1.2 Hz, J₂=8.3 Hz, 1H), 7.33 (d, J=8.3 Hz, 1H), 7.16 (dd, J₁=1.5 Hz, J₂=8.3 Hz), 6.78 (d, J=8.5 Hz, 1H), 4.61 (t, J=8.7 Hz, 2H), 3.64 (q, J=7.1 Hz, 4H), 3.26 (t, J=8.6 Hz, 2H), 1.33 (t, J=7.1 Hz, 6H).

Example 79: ¹H NMR (400 MHz, CDCl₃) δ: 7.82 (d, J=0.7 Hz, 1H), 7.80 (s, 1H), 7.68 (s, 1H), 7.61 (dd, J₁=1.4 Hz, J₂=8.3 Hz, 1H), 7.34 (d, J=8.3 Hz, 1H), 7.17 (dd, J₁=1.5 Hz, J₂=8.5 Hz, 1H), 6.78 (d, J=8.5 Hz, 1H), 4.61 (t, J=8.7 Hz, 2H), 3.67-3.74 (m, 4H), 3.26 (t, J=8.6 Hz, 2H), 2.03-2.13 (m, 4H).

Example 80: ¹H NMR (400 MHz, CDCl₃) δ: 7.90 (s, 1H), 7.79 (s br, 1H), 7.66-7.71 (m, 2H), 7.43 (d, J=8.3 Hz, 1H), 7.17 (d, J=8.3 Hz, 1H), 6.79 (d, J=8.5 Hz, 1H), 5.43 (d, J=7.5 Hz, 2H), 4.79 (d, J=7.5 Hz, 2H), 4.61 (t, J=8.7 Hz, 2H), 4.15 (t, J=7.3 Hz, 2H), 3.26 (t, J=8.6 Hz, 2H), 2.80 (t, J=7.2 Hz, 2H).

Example 81

2,3-Dihydro-benzofuran-5-carboxylic acid (2-piperidin-1-yl-benzothiazol-5-yl)-amide To a solution of 2-(piperidin-1-yl)benzo[d]thiazol-5-amine (53 mg, 226 µmol) and 2,3-dihydrobenzo[b]furan-5-carboxylic acid (37 mg, 226 µmol) in MeCN (2 mL) pyridine (0.18 mL) followed by POCl₃ (0.23 mL, 248 µmol) was added. The mixture was stirred at rt for 15 in before it was diluted with water (0.25 mL) and then concentrated. The residue was dissolved in DMF (1.5 mL) and formic acid (0.1 mL) and separated by prep. HPLC to give the title compound (31 mg) as a solid; LC-MS: $t_R$=0.76 min; [M+H]⁺=380.25; ¹H NMR (400 MHz, CDCl₃) δ: 7.80 (s, 2H), 7.66-7.71 (m, 2H), 7.56 (s, 2H), 6.86 (d, J=8.3 Hz, 1H), 4.68 (t, J=8.8 Hz, 2H), 3.60-3.67 (m, 4H), 3.29 (t, J=8.7 Hz, 2H), 1.68-1.78 (m, 6H).

Examples 82 TO 97

The following Example compounds were prepared in analogy to Example 81 starting from Intermediates D2 to D17 and 2,3-dihydrobenzo[b]furan-5-carboxylic acid.

| Example | Name | LC-MS $t_R$ [min] | [M + H]⁺ |
|---|---|---|---|
| 82 | 2,3-Dihydro-benzofuran-5-carboxylic acid (2-morpholin-4-yl-benzothiazol-5-yl)-amide | 0.76 | 382.23 |
| 83 | 2,3-Dihydro-benzofuran-5-carboxylic acid [2-(4-methyl-piperazin-1-yl)-benzothiazol-5-yl]-amide | 0.62 | 395.22 |
| 84 | 2,3-Dihydro-benzofuran-5-carboxylic acid (2-pyrrolidin-1-yl-benzothiazol-5-yl)-amide | 0.69 | 366.17 |
| 85 | 2,3-Dihydro-benzofuran-5-carboxylic acid (2-diethylamino-benzothiazol-5-yl)-amide | 0.73 | 367.98 |
| 86 | 2,3-Dihydro-benzofuran-5-carboxylic acid (2-dimethylamino-benzothiazol-5-yl)-amide | 0.66 | 344.01 |
| 87 | 2,3-Dihydro-benzofuran-5-carboxylic acid [2-(3,3-difluoro-azetidin-1-yl)-benzothiazol-5-yl]-amide | 0.85 | 388.11 |
| 88 | 2,3-Dihydro-benzofuran-5-carboxylic acid [2-(3,3-difluoro-pyrrolidin-1-yl)-benzothiazol-5-yl]-amide | 0.84 | 401.96 |
| 89 | 2,3-Dihydro-benzofuran-5-carboxylic acid [2-(3,3-difluoro-piperidin-1-yl)-benzothiazol-5-yl]-amide | 0.89 | 416.07 |
| 90 | 2,3-Dihydro-benzofuran-5-carboxylic acid [2-(6-oxa-1-aza-spiro[3.3]hept-1-yl)-benzothiazol-5-yl]-amide | 0.75 | 394.12 |
| 91 | 2,3-Dihydro-benzofuran-5-carboxylic acid [2-(2-oxa-6-aza-spiro[3.3]hept-6-yl)-benzothiazol-5-yl]-amide | 0.69 | 394.12 |
| 92 | 2,3-Dihydro-benzofuran-5-carboxylic acid [2-(1,1-dioxo-1l6-thiomorpholin-4-yl)-benzothiazol-5-yl]-amide | 0.78 | 430.01 |
| 93 | 2,3-Dihydro-benzofuran-5-carboxylic acid {2-[(2-dimethylamino-ethyl)-methyl-amino]-benzothiazol-5-yl}-amide | 0.64 | 397.16 |
| 94 | 2,3-Dihydro-benzofuran-5-carboxylic acid [2-(3-methoxy-pyrrolidin-1-yl)-benzothiazol-5-yl]-amide | 0.70 | 396.14 |
| 95 | 2,3-Dihydro-benzofuran-5-carboxylic acid [2-(4-methoxy-piperidin-1-yl)-benzothiazol-5-yl]-amide | 0.77 | 410.12 |

| Example | Name | LC-MS $t_R$ [min] | [M + H]⁺ |
|---|---|---|---|
| 96 | 2,3-Dihydro-benzofuran-5-carboxylic acid [2-(3-hydroxy-3-methyl-azetidin-1-yl)-benzothiazol-5-yl]-amide | 0.67 | 382.14 |
| 97 | 2,3-Dihydro-benzofuran-5-carboxylic acid [2-(4-dimethylamino-piperidin-1-yl)-benzothiazol-5-yl]-amide | 0.62 | 423.13 |

Example 82: ¹H NMR (400 MHz, CDCl₃) δ: 7.80 (s, 2H), 7.76 (d, J=1.7 Hz, 1H), 7.69 (dd, J₁=1.8 Hz, J₂=8.3 Hz, 1H), 7.58 (m, 2H), 6.86 (d, J=8.3 Hz, 1H), 4.69 (t, J=8.8 Hz, 2H), 3.86 (m, 4H), 3.66 (m, 4H), 3.30 (t, J=8.8 Hz, 2H).

Example 83: ¹H NMR (400 MHz, D₆-DMSO) δ: 10.06 (s, 1H), 7.98 (d, J=1.9 Hz, 1H), 7.89 (s, 1H), 7.80 (dd, J₁=1.8 Hz, J₂=8.4 Hz, 1H), 7.69 (d, J=8.5 Hz, 1H), 7.48 (dd, J₁=2.0 Hz, J₂=8.6 Hz, 1H), 6.89 (d, J=8.4 Hz, 1H), 4.64 (t, J=8.8 Hz, 2H), 3.56-3.61 (m, 4H), 3.27 (t, J=8.7 Hz, 2H), 2.49-2.53 (m, 4H), 2.30 (s, 3H).

Example 87: ¹H NMR (400 MHz, CDCl₃) δ: 7.84 (s, 1H), 7.81 (s, 2H), 7.69 (dd, J₁=1.8 Hz, J₂=8.8 Hz), 7.59-7.65 (m, 2H), 6.87 (d, J=8.3 Hz, 1H), 4.70 (t, J=8.8 Hz, 2H), 4.59 (t, J=11.7 Hz, 4H), 3.30 (t, J=8.7 Hz, 2H).

Example 90: ¹H NMR (400 MHz, D₆-DMSO) δ: 10.09 (s, 1H), 8.07 (s, 1H), 7.90 (s, 1H), 7.81 (d, J=8.1 Hz, 1H), 7.75 (d, J=8.3 Hz, 1H), 7.50 (d, J=8.6 Hz, 1H), 6.91 (d, J=8.2 Hz, 1H), 5.34 (d, J=7.2 Hz, 2H), 4.59-4.74 (m, 4H), 3.90-4.02 (m, 2H), 3.29 (t, J=8.7 Hz, 2H), 2.68-2.79 (m, 2H).

Example 92: ¹H NMR (400 MHz, D₆-DMSO) δ: 10.08 (s, 1H), 8.04 (d, J=1.9 Hz, 1H), 7.89 (s, 1H), 7.80 (dd, J₁=1.6 Hz, J₂=8.4 Hz, 1H), 7.74 (d, J=8.6 Hz, 1H), 7.51 (dd, J₁=1.9 Hz, J₂=8.6 Hz, 1H), 6.89 (d, J=8.4 Hz, 1H), 4.64 (t, J=8.8 Hz, 2H), 4.04-4.09 (m, 4H), 3.31-3.34 (m, 4H), 3.27 (t, J=8.8 Hz, 2H).

Example 96: ¹H NMR (400 MHz, D₆-DMSO) δ: 10.05 (s, 1H), 7.96 (d, J=1.9 Hz, 1H), 7.88 (s, 1H), 7.79 (dd, J₁=1.4 Hz, J₂=8.4 Hz, 1H), 7.68 (d, J=8.6 Hz, 1H), 7.48 (dd, J₁=1.9 Hz, J₂=8.6 Hz, 1H), 6.89 (d, J=8.4 Hz, 1H), 5.85 (s br, 1H), 4.64 (t, J=8.8 Hz, 2H), 3.95-4.04 (m, 4H), 3.27 (t, J=8.7 Hz, 2H), 1.47 (s, 3H).

Example 98

(S)—N-(2-(3-hydroxypyrrolidin-1-yl)benzo[d]thiazol-5-yl)-2,3-dihydrobenzofuran-5-carboxamide To a solution of (S)-pyrrolidin-3-ol (8 mg, 91 μmol) and Et₃N (51 μL, 362 μmol) in THF (0.6 mL) N-(2-chlorobenzo[d]thiazol-5-yl)-2,3-dihydrobenzofuran-5-carboxamide (30 mg, 72.5 μmol) was added and the mixture was stirred at 65° C. for 16 h. The mixture was concentrated, dissolved in DMSO (0.6 mL) and separated by prep. HPLC to give the title compound (17 mg) as a white solid; LC-MS: $t_R$=0.80 min; [M+H]⁺=382.00; ¹H NMR (400 MHz, DMSO) δ: 10.06 (s, 1H), 7.89 (s, 1H), 7.85 (s, H), 7.76 (d, J=8.3 Hz, 1H), 7.64 (d, J=8.6 Hz, 1H), 7.39 (d, J=8.3 Hz, 1H), 6.86 (d, J=8.3 Hz, 1H), 5.28 (d, J=3.2 Hz, 1H), 4.61 (t, J=8.6 Hz, 2H), 4.40-4.46 (m, 1H), 3.66-3.82 (m, 4H), 3.24 (t, J=8.6 Hz, 2H), 2.04-2.17 (m, 1H), 1.89-2.00 (m, 1H).

Examples 99 TO 117

The following Example compounds were prepared in analogy to Example 98 starting from Intermediate E1 and the appropriate amines.

| Example | Name | LC-MS $t_R$ [min] | [M + H]⁺ |
|---|---|---|---|
| 99 | 2,3-Dihydro-benzofuran-5-carboxylic acid [2-(2-oxa-7-aza-spiro[3.5]non-7-yl)-benzothiazol-5-yl]-amide | 0.91 | 421.68 |
| 100 | 2,3-Dihydro-benzofuran-5-carboxylic acid {2-[methyl-(1-oxetan-3-yl-piperidin-4-yl)-amino]-benzothiazol-5-yl}-amide | 0.87 | 465.05 |
| 101 | 2,3-Dihydro-benzofuran-5-carboxylic acid [2-(2-oxa-6-aza-spiro[3.5]non-6-yl)-benzothiazol-5-yl]-amide | 0.93 | 421.70 |
| 102 | 2,3-Dihydro-benzofuran-5-carboxylic acid [2-(4-oxetan-3-yl-piperazin-1-yl)-benzothiazol-5-yl]-amide | 0.84 | 437.02 |
| 103 | 2,3-Dihydro-benzofuran-5-carboxylic acid [2-(methyl-oxetan-3-yl-amino)-benzothiazol-5-yl]-amide | 0.87 | 382.01 |
| 104 | 2,3-Dihydro-benzofuran-5-carboxylic acid [2-(1-oxa-6-aza-spiro[3.3]hept-6-yl)-benzothiazol-5-yl]-amide | 0.88 | 394.01 |
| 105 | 2,3-Dihydro-benzofuran-5-carboxylic acid [2-(3-dimethylaminomethyl-pyrrolidin-1-yl)-benzothiazol-5-yl]-amide | 0.96 | 422.95 |
| 106 | 2,3-Dihydro-benzofuran-5-carboxylic acid [2-(3-isopropoxy-azetidin-1-yl)-benzothiazol-5-yl]-amide | 1.01 | 410.05 |
| 107 | 2,3-Dihydro-benzofuran-5-carboxylic acid [2-(2-ethoxymethyl-pyrrolidin-1-yl)-benzothiazol-5-yl]-amide | 1.07 | 424.05 |
| 108 | 2,3-Dihydro-benzofuran-5-carboxylic acid [2-(3-methoxy-piperidin-1-yl)-benzothiazol-5-yl]-amide | 0.98 | 410.02 |
| 109 | 2,3-Dihydro-benzofuran-5-carboxylic acid [2-(3-hydroxy-azetidin-1-yl)-benzothiazol-5-yl]-amide | 0.79 | 367.97 |
| 110 | 2,3-Dihydro-benzofuran-5-carboxylic acid [2-(4-hydroxy-piperidin-1-yl)-benzothiazol-5-yl]-amide | 0.83 | 395.99 |
| 111 | rac-2,3-Dihydro-benzofuran-5-carboxylic acid [2-(2-phenyl-azetidin-1-yl)-benzothiazol-5-yl]-amide | 1.10 | 428.00 |
| 112 | 2,3-Dihydro-benzofuran-5-carboxylic acid [2-((R)-3-hydroxy-pyrrolidin-1-yl)-benzothiazol-5-yl]-amide | 0.81 | 381.98 |

-continued

| Example | Name | LC-MS t$_R$ [min] | [M + H]$^+$ |
|---|---|---|---|
| 113 | 2,3-Dihydro-benzofuran-5-carboxylic acid [2-(2-methoxymethyl-pyrrolidin-1-yl)-benzothiazol-5-yl]-amide | 1.00 | 410.01 |
| 114 | 2,3-Dihydro-benzofuran-5-carboxylic acid [2-((S)-3-hydroxy-piperidin-1-yl)-benzothiazol-5-yl]-amide | 0.85 | 396.00 |
| 115 | 2,3-Dihydro-benzofuran-5-carboxylic acid [2-(2-oxa-6-aza-spiro[3.4]oct-6-yl)-benzothiazol-5-yl]-amide | 0.87 | 408.02 |
| 116 | 2,3-Dihydro-benzofuran-5-carboxylic acid [2-((R)-3-hydroxy-piperidin-1-yl)-benzothiazol-5-yl]-amide | 0.85 | 395.99 |
| 117 | 2,3-Dihydro-benzofuran-5-carboxylic acid [2-(2-dimethylaminomethyl-pyrrolidin-1-yl)-benzothiazol-5-yl]-amide | 1.05 | 422.94 |

Example 101: $^1$H NMR (400 MHz, D$_6$-DMSO) δ: 10.08 (s, 1H), 7.90 (s, 1H), 7.85 (s, 1H), 7.76 (d, J=8.5 Hz, 1H), 7.65 (d, J=8.5 Hz, 1H), 7.42 (dd, J$_1$=1.1 Hz, J$_2$=8.5 Hz, 1H), 6.86 (d, J=8.3 Hz, 1H), 4.61 (t, J=8.7 Hz, 2H), 4.31 (s br, 4H), 3.79-3.82 (m, 2H), 3.42-3.48 (m, 2H), 3.24 (t, J=8.7 Hz, 2H), 1.84-1.90 (m, 2H), 1.52-1.60 (m, 2H).

Example 102: $^1$H NMR (400 MHz, D$_6$-DMSO) δ: 10.09 (s, 1H), 7.91 (s, 1H), 7.84 (s, 1H), 7.75 (d, J=7.8 Hz, 1H), 7.66 (d, J=8.8 Hz, 1H), 7.42 (d, J=8.1 Hz, 1H), 6.86 (d, J=8.3 Hz, 1H), 4.61 (t, J=8.8 Hz, 2H), 4.53-4.58 (m, 2H), 4.44-4.49 (m, 2H), 3.62-3.70 (m, 2H), 3.54-3.60 (m, 2H), 3.43-3.49 (m, 1H), 3.24 (t, J=8.8 Hz, 2H), 2.36-2.42 (m, 4H).

Example 103: $^1$H NMR (400 MHz, D$_6$-DMSO) δ: 10.09 (s, 1H), 7.93 (d, J=1.4 Hz, 1H), 7.84 (s, 1H), 7.75 (d, J=8.4 Hz, 1H), 7.67 (d, J=8.6 Hz, 1H), 7.41 (dd, J$_1$=1.5 Hz, J$_2$=8.3 Hz, 1H), 6.86 (d, J=8.3 Hz, 1H), 5.25 (quint, J=6.8 Hz, 1H), 4.75-4.85 (m, 4H), 4.61 (t, J=8.6 Hz, 2H), 3.22-3.27 (t, J=8.6 Hz, 2H), 3.21 (s, 3H).

Example 109: $^1$H NMR (400 MHz, D$_6$-DMSO) δ:10.09 (s, 1H), 7.90 (s, 1H), 7.84 (s, 1H), 7.76 (d, J=8.4 Hz, 1H), 7.66 (d, J=8.5 Hz, 1H), 7.43 (d, J=8.5 Hz, 1H), 6.86 (d, J=8.4 Hz, 1H), 6.09 (d, J=6.5 Hz, 1H), 4.64-4.70 (m, 1H), 4.61 (t, J=8.6 Hz, 2H), 4.28-4.34 (m, 2H), 3.87 (dd, J$_1$=4.4 Hz, J$_2$=8.6 Hz, 2H), 3.24 (t, J=8.7 Hz, 2H).

Example 116: $^1$H NMR (400 MHz, D$_6$-DMSO) δ:10.07 (s, 1H), 7.85 (s, 1H), 7.83 (s, 1H), 7.75 (d, J=8.3 Hz, 1H), 7.62 (d, J=8.6 Hz, 1H), 7.38 (dd, J$_1$=1.0 Hz, J$_2$=8.6 Hz, 1H), 6.85 (d, J=8.3 Hz, 1H), 5.25 (d, J=3.9 Hz, 1H), 4.61 (t, J=8.8 Hz, 2H), 3.57-3.76 (m, 2H), 3.19-3.30 (m, 3H), 3.08 (dd, J$_1$=8.6 Hz, J$_2$=12.7 Hz, 1H), 1.75-1.91 (m, 2H), 1.40-1.54 (m, 2H).

Example 118

2,3-Dihydro-benzofuran-5-carboxylic acid (2-azetidin-1-yl-benzooxazol-5-yl)-amide A solution of 2,3-dihydrobenzo[b]furan-5-carboxylic acid (30.3 mg, 0.185 mmol), HBTU (70.1 mg, 0.185 mmol) and DIPEA (95 µL, 0.554 mmol) in DMF (1 mL) was stirred at rt for 30 min before 2-azetidin-1-yl-benzooxazol-5-ylamine (35 mg, 0.185 mmol, Intermediate A40) was added. The mixture was stirred at 50° C. for 16 h before it was separated by prep. HPLC to give the title compound (59 mg) as a colourless resin; LC-MS: t$_R$=0.72 min; [M+H]$^+$=336.09; $^1$H NMR (400 MHz, CDCl$_3$): δ 7.81 (s, 1H), 7.77 (s, 1H), 7.69 (d, J=8.3 Hz, 1H), 7.52 (s, 1H), 7.42 (d, J=8.7 Hz, 1H), 7.24 (d, J=8.6 Hz, 1H), 6.86 (d, J=8.3 Hz, 1H), 4.69 (t, J=8.8 Hz, 2H), 4.33 (t, J=7.6 Hz, 4H), 3.30 (t, J=8.7 Hz, 2H), 2.54 (quint, J=7.5 Hz).

Examples 119 TO 195

The following Example compounds were prepared in analogy to Example 118 starting from Intermediates A2 to A6, A8, A12, A16, A17, A25, A36, A37, and A40 to A48 and the appropriate benzoic acid derivatives.

| Example | Name | LC-MS t$_R$ [min] | [M + H]$^+$ |
|---|---|---|---|
| 119 | 2,3-Dihydro-benzofuran-5-carboxylic acid (2-ethylamino-benzooxazol-5-yl)-amide | 0.67 | 324.09 |
| 120 | 2,3-Dihydro-benzofuran-5-carboxylic acid [2-(3-pyridin-2-yl-azetidin-1-yl)-benzooxazol-5-yl]-amide | 0.66 | 413.26 |
| 121 | Benzo[1,3]dioxole-5-carboxylic acid [2-(3,3-difluoro-azetidin-1-yl)-benzooxazol-5-yl]-amide | 0.89 | 374.02 |
| 122 | Benzo[1,3]dioxole-5-carboxylic acid [2-(3-hydroxy-azetidin-1-yl)-benzooxazol-5-yl]-amide | 0.72 | 353.89 |
| 123 | Benzo[1,3]dioxole-5-carboxylic acid [2-(1-aza-spiro[3.3]hept-1-yl)-benzooxazol-5-yl]-amide | 1.01 | 378.07 |
| 124 | Benzo[1,3]dioxole-5-carboxylic acid [2-(6-oxa-1-aza-spiro[3.3]hept-1-yl)-benzooxazol-5-yl]-amide | 0.79 | 380.05 |
| 125 | Benzo[1,3]dioxole-5-carboxylic acid [2-(6-oxa-1-aza-spiro[3.4]oct-1-yl)-benzooxazol-5-yl]-amide | 0.83 | 394.06 |
| 126 | Benzo[1,3]dioxole-5-carboxylic acid [2-(7-oxa-1-aza-spiro[3.5]non-1-yl)-benzooxazol-5-yl]-amide | 0.85 | 408.10 |
| 127 | Benzo[1,3]dioxole-5-carboxylic acid (2-pyrrolidin-1-yl-benzooxazol-5-yl)-amide | 0.89 | 352.04 |
| 128 | Benzo[1,3]dioxole-5-carboxylic acid [2-(2-oxa-5-aza-spiro[3.4]oct-5-yl)-benzooxazol-5-yl]-amide | 0.76 | 394.26 |

| Example | Name | LC-MS | |
|---|---|---|---|
| | | $t_R$ [min] | $[M + H]^+$ |
| 129 | Benzo[1,3]dioxole-5-carboxylic acid (2-piperidin-1-yl-benzooxazol-5-yl)-amide | 0.97 | 266.04 |
| 130 | Benzo[1,3]dioxole-5-carboxylic acid [2-(3,3-difluoro-piperidin-1-yl)-benzooxazol-5-yl]-amide | 0.94 | 401.83 |
| 131 | Benzo[1,3]dioxole-5-carboxylic acid [2-(4-methoxy-piperidin-1-yl)-benzooxazol-5-yl]-amide | 0.88 | 396.08 |
| 132 | Benzo[1,3]dioxole-5-carboxylic acid [2-(2-oxa-7-aza-spiro[3.5]non-7-yl)-benzooxazol-5-yl]-amide | 0.83 | 408.10 |
| 133 | Benzo[1,3]dioxole-5-carboxylic acid [2-(2-oxa-6-aza-spiro[3.5]non-6-yl)-benzooxazol-5-yl]-amide | 0.84 | 408.10 |
| 134 | Benzo[1,3]dioxole-5-carboxylic acid [2-(4,4-difluoro-piperidin-1-yl)-benzooxazol-5-yl]-amide | 0.95 | 401.84 |
| 135 | Benzo[1,3]dioxole-5-carboxylic acid [2-(4-hydroxy-piperidin-1-yl)-benzooxazol-5-yl]-amide | 0.75 | 382.08 |
| 136 | Benzo[1,3]dioxole-5-carboxylic acid (2-morpholin-4-yl-benzooxazol-5-yl)-amide | 0.81 | 368.03 |
| 137 | Benzo[1,3]dioxole-5-carboxylic acid [2-(4-methyl-piperazin-1-yl)-benzooxazol-5-yl]-amide | 0.79 | 381.10 |
| 138 | Benzo[1,3]dioxole-5-carboxylic acid [2-(cyclopropyl-oxetan-3-yl-amino)-benzooxazol-5-yl]-amide | 0.84 | 394.07 |
| 139 | Benzo[1,3]dioxole-5-carboxylic acid (2-diethylamino-benzooxazol-5-yl)-amide | 0.95 | 353.90 |
| 140 | Chroman-6-carboxylic acid [2-(3-hydroxy-azetidin-1-yl)-benzooxazol-5-yl]-amide | 0.78 | 366.05 |
| 141 | Chroman-6-carboxylic acid [2-(3,3-difluoro-azetidin-1-yl)-benzooxazol-5-yl]-amide | 0.95 | 385.84 |
| 142 | Chroman-6-carboxylic acid [2-(1-aza-spiro[3.3]hept-1-yl)-benzooxazol-5-yl]-amide | 1.06 | 390.10 |
| 143 | Chroman-6-carboxylic acid [2-(6-oxa-1-aza-spiro[3.3]hept-1-yl)-benzooxazol-5-yl]-amide | 0.85 | 392.09 |
| 144 | Chroman-6-carboxylic acid [2-(6-oxa-1-aza-spiro[3.4]oct-1-yl)-benzooxazol-5-yl]-amide | 0.89 | 406.09 |
| 145 | Chroman-6-carboxylic acid [2-(7-oxa-1-aza-spiro[3.5]non-1-yl)-benzooxazol-5-yl]-amide | 0.91 | 420.13 |
| 146 | Chroman-6-carboxylic acid (2-pyrrolidin-1-yl-benzooxazol-5-yl)-amide | 0.94 | 364.06 |
| 147 | Chroman-6-carboxylic acid [2-(2-oxa-5-aza-spiro[3.4]oct-5-yl)-benzooxazol-5-yl]-amide | 0.80 | 406.28 |
| 148 | Chroman-6-carboxylic acid (2-piperidin-1-yl-benzooxazol-5-yl)-amide | 1.03 | 378.09 |
| 149 | Chroman-6-carboxylic acid [2-(4,4-difluoro-piperidin-1-yl)-benzooxazol-5-yl]-amide | 1.01 | 414.11 |
| 150 | Chroman-6-carboxylic acid [2-(3,3-difluoro-piperidin-1-yl)-benzooxazol-5-yl]-amide | 1.00 | 141.09 |
| 151 | Chroman-6-carboxylic acid [2-(4-hydroxy-piperidin-1-yl)-benzooxazol-5-yl]-amide | 0.81 | 394.10 |
| 152 | Chroman-6-carboxylic acid [2-(4-methoxy-piperidin-1-yl)-benzooxazol-5-yl]-amide | 0.94 | 408.13 |
| 153 | Chroman-6-carboxylic acid [2-(2-oxa-7-aza-spiro[3.5]non-7-yl)-benzooxazol-5-yl]-amide | 0.89 | 420.15 |
| 154 | Chroman-6-carboxylic acid [2-(2-oxa-6-aza-spiro[3.5]non-6-yl)-benzooxazol-5-yl]-amide | 0.90 | 420.14 |
| 155 | Chroman-6-carboxylic acid (2-morpholin-4-yl-benzooxazol-5-yl)-amide | 0.87 | 380.09 |
| 156 | Chroman-6-carboxylic acid [2-(4-methyl-piperazin-1-yl)-benzooxazol-5-yl]-amide | 0.85 | 393.11 |
| 157 | Chroman-6-carboxylic acid (2-diethylamino-benzooxazol-5-yl)-amide | 1.00 | 366.12 |
| 158 | Chroman-6-carboxylic acid [2-(cyclopropyl-oxetan-3-yl-amino)-benzooxazol-5-yl]-amide | 0.90 | 406.12 |
| 159 | 2,3-Dihydro-benzo[1,4]dioxine-6-carboxylic acid [2-(3-hydroxy-azetidin-1-yl)-benzooxazol-5-yl]-amide | 0.72 | 368.04 |
| 160 | 2,3-Dihydro-benzo[1,4]dioxine-6-carboxylic acid [2-(6-oxa-1-aza-spiro[3.3]hept-1-yl)-benzooxazol-5-yl]-amide | 0.79 | 394.07 |
| 161 | 2,3-Dihydro-benzo[1,4]dioxine-6-carboxylic acid [2-(1-aza-spiro[3.3]hept-1-yl)-benzooxazol-5-yl]-amide | 1.01 | 392.08 |
| 162 | 2,3-Dihydro-benzo[1,4]dioxine-6-carboxylic acid [2-(6-oxa-1-aza-spiro[3.4]oct-1-yl)-benzooxazol-5-yl]-amide | 0.83 | 408.11 |
| 163 | 2,3-Dihydro-benzo[1,4]dioxine-6-carboxylic acid [2-(7-oxa-1-aza-spiro[3.5]non-1-yl)-benzooxazol-5-yl]-amide | 0.86 | 422.12 |
| 164 | 2,3-Dihydro-benzo[1,4]dioxine-6-carboxylic acid (2-pyrrolidin-1-yl-benzooxazol-5-yl)-amide | 0.89 | 366.05 |
| 165 | 2,3-Dihydro-benzo[1,4]dioxine-6-carboxylic acid [2-(2-oxa-5-aza-spiro[3.4]oct-5-yl)-benzooxazol-5-yl]-amide | 0.76 | 408.27 |
| 166 | 2,3-Dihydro-benzo[1,4]dioxine-6-carboxylic acid (2-piperidin-1-yl-benzooxazol-5-yl)-amide | 0.98 | 380.09 |
| 167 | 2,3-Dihydro-benzo[1,4]dioxine-6-carboxylic acid [2-(4-hydroxy-piperidin-1-yl)-benzooxazol-5-yl]-amide | 0.75 | 396.09 |
| 168 | 2,3-Dihydro-benzo[1,4]dioxine-6-carboxylic acid [2-(3,3-difluoro-piperidin-1-yl)-benzooxazol-5-yl]-amide | 0.94 | 416.09 |

|   |   | LC-MS | |
|---|---|---|---|
| Example | Name | $t_R$ [min] | $[M + H]^+$ |
| 169 | 2,3-Dihydro-benzo[1,4]dioxine-6-carboxylic acid [2-(4-methoxy-piperidin-1-yl)-benzooxazol-5-yl]-amide | 0.88 | 410.11 |
| 170 | 2,3-Dihydro-benzo[1,4]dioxine-6-carboxylic acid [2-(4,4-difluoro-piperidin-1-yl)-benzooxazol-5-yl]-amide | 0.95 | 416.09 |
| 171 | 2,3-Dihydro-benzo[1,4]dioxine-6-carboxylic acid [2-(2-oxa-6-aza-spiro[3.5]non-6-yl)-benzooxazol-5-yl]-amide | 0.85 | 422.12 |
| 172 | 2,3-Dihydro-benzo[1,4]dioxine-6-carboxylic acid [2-(2-oxa-7-aza-spiro[3.5]non-7-yl)-benzooxazol-5-yl]-amide | 0.83 | 422.12 |
| 173 | 2,3-Dihydro-benzo[1,4]dioxine-6-carboxylic acid (2-morpholin-4-yl-benzooxazol-5-yl)-amide | 0.81 | 382.09 |
| 174 | 2,3-Dihydro-benzo[1,4]dioxine-6-carboxylic acid [2-(4-methyl-piperazin-1-yl)-benzooxazol-5-yl]-amide | 0.79 | 395.11 |
| 175 | 2,3-Dihydro-benzo[1,4]dioxine-6-carboxylic acid (2-diethylamino-benzooxazol-5-yl)-amide | 0.95 | 368.07 |
| 176 | 2,3-Dihydro-benzo[1,4]dioxine-6-carboxylic acid [2-(cyclopropyl-oxetan-3-yl-amino)-benzooxazol-5-yl]-amide | 0.85 | 408.10 |
| 177 | 4-Methyl-3,4-dihydro-2H-benzo[1,4]oxazine-6-carboxylic acid [2-(3-hydroxy-azetidin-1-yl)-benzooxazol-5-yl]-amide | 0.72 | 381.08 |
| 178 | 4-Methyl-3,4-dihydro-2H-benzo[1,4]oxazine-6-carboxylic acid [2-(3,3-difluoro-azetidin-1-yl)-benzooxazol-5-yl]-amide | 0.92 | 401.03 |
| 179 | 4-Methyl-3,4-dihydro-2H-benzo[1,4]oxazine-6-carboxylic acid [2-(1-aza-spiro[3.3]hept-1-yl)-benzooxazol-5-yl]-amide | 0.96 | 405.12 |
| 180 | 4-Methyl-3,4-dihydro-2H-benzo[1,4]oxazine-6-carboxylic acid [2-(6-oxa-1-aza-spiro[3.3]hept-1-yl)-benzooxazol-5-yl]-amide | 0.81 | 407.10 |
| 181 | 4-Methyl-3,4-dihydro-2H-benzo[1,4]oxazine-6-carboxylic acid [2-(6-oxa-1-aza-spiro[3.4]oct-1-yl)-benzooxazol-5-yl]-amide | 0.82 | 421.11 |
| 182 | 4-Methyl-3,4-dihydro-2H-benzo[1,4]oxazine-6-carboxylic acid [2-(7-oxa-1-aza-spiro[3.5]non-1-yl)-benzooxazol-5-yl]-amide | 0.83 | 435.13 |
| 183 | 4-Methyl-3,4-dihydro-2H-benzo[1,4]oxazine-6-carboxylic acid (2-pyrrolidin-1-yl-benzooxazol-5-yl)-amide | 0.79 | 379.13 |
| 184 | 4-Methyl-3,4-dihydro-2H-benzo[1,4]oxazine-6-carboxylic acid [2-(2-oxa-5-aza-spiro[3.4]oct-5-yl)-benzooxazol-5-yl]-amide | 0.78 | 421.26 |
| 185 | 4-Methyl-3,4-dihydro-2H-benzo[1,4]oxazine-6-carboxylic acid (2-piperidin-1-yl-benzooxazol-5-yl)-amide | 0.90 | 393.12 |
| 186 | 4-Methyl-3,4-dihydro-2H-benzo[1,4]oxazine-6-carboxylic acid [2-(4-hydroxy-piperidin-1-yl)-benzooxazol-5-yl]-amide | 0.74 | 409.13 |
| 187 | 4-Methyl-3,4-dihydro-2H-benzo[1,4]oxazine-6-carboxylic acid [2-(4,4-difluoro-piperidin-1-yl)-benzooxazol-5-yl]-amide | 0.97 | 429.12 |
| 188 | 4-Methyl-3,4-dihydro-2H-benzo[1,4]oxazine-6-carboxylic acid [2-(3,3-difluoro-piperidin-1-yl)-benzooxazol-5-yl]-amide | 0.97 | 429.14 |
| 189 | 4-Methyl-3,4-dihydro-2H-benzo[1,4]oxazine-6-carboxylic acid [2-(2-oxa-6-aza-spiro[3.5]non-6-yl)-benzooxazol-5-yl]-amide | 0.84 | 435.14 |
| 190 | 4-Methyl-3,4-dihydro-2H-benzo[1,4]oxazine-6-carboxylic acid [2-(2-oxa-7-aza-spiro[3.5]non-7-yl)-benzooxazol-5-yl]-amide | 0.82 | 435.13 |
| 191 | 4-Methyl-3,4-dihydro-2H-benzo[1,4]oxazine-6-carboxylic acid [2-(4-methoxy-piperidin-1-yl)-benzooxazol-5-yl]-amide | 0.86 | 423.15 |
| 192 | 4-Methyl-3,4-dihydro-2H-benzo[1,4]oxazine-6-carboxylic acid (2-morpholin-4-yl-benzooxazol-5-yl)-amide | 0.82 | 395.09 |
| 193 | 4-Methyl-3,4-dihydro-2H-benzo[1,4]oxazine-6-carboxylic acid [2-(4-methyl-piperazin-1-yl)-benzooxazol-5-yl]-amide | 0.67 | 408.15 |
| 194 | 4-Methyl-3,4-dihydro-2H-benzo[1,4]oxazine-6-carboxylic acid (2-diethylamino-benzooxazol-5-yl)-amide | 0.86 | 381.12 |
| 195 | 4-Methyl-3,4-dihydro-2H-benzo[1,4]oxazine-6-carboxylic acid [2-(cyclopropyl-oxetan-3-yl-amino)-benzooxazol-5-yl]-amide | 0.85 | 421.13 |

Example 124: $^1$H NMR (400 MHz, D$_6$-DMSO): δ 10.07 (s, 1H), 7.80 (s, 1H), 7.59 (d, J=8.0 Hz, 1H), 7.53 (d, J=0.7 Hz, 1H), 7.40-7.47 (m, 2H), 7.07 (d, J=8.2 Hz, 1H), 6.15 (s, 2H), 5.23 (d, J=7.4 Hz, 2H), 4.67 (d, J=7.4 Hz, 2H), 4.02 (t, J=7.2 Hz, 2H), 2.73 (t, J=7.1 Hz, 2H).

Example 133: $^1$H NMR (400 MHz, D$_6$-DMSO): δ 10.04 (s, 1H), 7.73 (s, 1H), 7.59 (d, J=8.2 Hz, 1H), 7.53 (s, 1H), 7.37 (s, 2H), 7.07 (d, J=8.1 Hz, 1H), 6.15 (s, 2H), 4.32 (s, 4H), 3.84 (s, 2H), 3.54 (t, J=5.1 Hz, 2H), 1.86-1.92 (m, 2H), 1.54-1.62 (m, 2H).

Example 144: $^1$H NMR (400 MHz, D$_6$-DMSO): δ 10.00 (s, 1H), 7.70-7.78 (m, 3H), 7.34-7.41 (m, 2H), 6.85 (d, J=8.3 Hz, 1H), 4.22 (t, J=4.8 Hz, 2H), 4.00-4.13 (m, 4H), 3.79-3.90 (m, 2H), 2.83 (t, J=6.1 Hz, 2H), 2.54-2.65 (m, 3H), 2.11-2.20 (m, 1H), 1.93-2.01 (m, 2H).

Example 159: $^1$H NMR (400 MHz, DMSO): δ 10.03 (s, 1H), 7.76 (s, 1H), 7.49-7.55 (m, 2H), 7.34-7.43 (m, 2H), 7.00 (d, J=8.4 Hz, 1H), 5.91 (d, J=6.7 Hz, 1H), 4.62-4.70 (m, 1H), 4.36-4.43 (m, 2H), 4.29-4.36 (m, 4H), 3.94-4.00 (m, 2H).

Example 176: $^1$H NMR (400 MHz, D$_6$-DMSO): δ 10.04 (s, 1H), 7.77 (s, 1H), 7.48-7.55 (m, 2H), 7.38-7.44 (m, 2H), 7.00 (d, J=8.3 Hz, 1H), 4.89-5.00 (m, 3H), 4.75 (t, J=6.2 Hz, 2H), 4.29-4.37 (m, 4H), 2.93-3.01 (m, 1H), 0.88-0.96 (m, 2H), 0.76-0.82 (m, 2H).

Example 186: $^1$H NMR (400 MHz, D$_6$-DMSO): δ 9.94 (s, 1H), 7.72 (s, 1H), 7.34 (s, 2H), 7.27 (m, 2H), 6.77-6.81 (m, 1H), 4.87 (d, J=4.0 Hz, 1H), 4.29-4.33 (m, 2H), 3.88-3.96 (m, 2H), 3.73-3.80 (m, 2H), 3.27-3.31 (m, 2H), 3.19 (d, J=5.2 Hz, 1H), 2.93 (s, 3H), 1.82-1.90 (m, 2H), 1.42-1.52 (m, 2H).

Example 196

2-Piperidin-1-yl-benzothiazole-5-carboxylic acid (2,3-dihydro-benzofuran-5-yl)-amide

To a solution of 2-chloro-N-(2,3-dihydrobenzofuran-5-yl)benzo[d]thiazole-5-carboxamide (62 mg, 0.174 mmol, Intermediate E2) and piperidine (17.2 µL, 0.174 mmol) in THF (1 mL), DIPEA (35 µL, 0.198 mmol) was added. The brown suspension was stirred at 70° C. for 6 h before another portion of piperidine (28 µL, 0.282 mmol) was added. Stirring was continued at 70° C. for 16 h. The mixture was concentrated and the residue was dissolved in DMF (2 mL) and purified by prep. HPLC to give the title compound (33 mg) as a pale yellow resin; LC-MS: $t_R$=0.84 min; [M+H]$^+$=380.22; $^1$H NMR (500 MHz, CDCl$_3$): δ 7.96 (d, J=1.5 Hz, 1H), 7.80 (s, 1H), 7.67-7.72 (m, 2H), 7.64 (dd, J$_1$=1.7 Hz, J$_2$=8.2 Hz, 1H), 7.16 (dd, J$_1$=2.2 Hz, J$_2$=8.5 Hz, 1H), 6.78 (d, J=8.5 Hz, 1H), 4.61 (t, J=8.7 Hz, 2H), 3.63-3.70 (m, 4H), 3.26 (t, J=8.7 Hz, 2H), 1.72-1.81 (m, 6H).

Examples 197 TO 212

The following Example compounds were prepared in analogy to Example 196 starting from Intermediates E2 to E4 and the appropriate aniline derivatives.

| Example | Name | LC-MS $t_R$ [min] | [M + H]$^+$ |
|---|---|---|---|
| 197 | 2-(6-Oxa-1-aza-spiro[3.3]hept-1-yl)-benzothiazole-5-carboxylic acid (2,3-dihydro-benzofuran-5-yl)-amide | 0.78 | 394.08 |
| 198 | 2-(4,4-Difluoro-piperidin-1-yl)-benzothiazole-5-carboxylic acid (2,3-dihydro-benzofuran-5-yl)-amide | 0.89 | 416.09 |
| 199 | 2-(1,1-Dioxo-thiomorpholin-4-yl)-benzothiazole-5-carboxylic acid (2,3-dihydro-benzofuran-5-yl)-amide | 0.76 | 430.06 |
| 200 | 2-(4-Methoxy-piperidin-1-yl)-benzothiazole-5-carboxylic acid (2,3-dihydro-benzofuran-5-yl)-amide | 0.82 | 410.11 |
| 201 | 2-(4-Methyl-piperazin-1-yl)-benzothiazole-5-carboxylic acid (2,3-dihydro-benzofuran-5-yl)-amide | 0.60 | 395.10 |
| 202 | 2-(6-Oxa-1-aza-spiro[3.4]oct-1-yl)-benzothiazole-5-carboxylic acid (2,3-dihydro-benzofuran-5-yl)-amide | 0.76 | 408.07 |
| 203 | 2-(6-Oxa-1-aza-spiro[3.3]hept-1-yl)-benzothiazole-5-carboxylic acid (2,3-dihydro-benzo[1,4]dioxin-6-yl)-amide | 0.79 | 410.04 |
| 204 | 2-(4,4-Difluoro-piperidin-1-yl)-benzothiazole-5-carboxylic acid (2,3-dihydro-benzo[1,4]dioxin-6-yl)-amide | 0.89 | 432.07 |
| 205 | 2-(4-Methoxy-piperidin-1-yl)-benzothiazole-5-carboxylic acid (2,3-dihydro-benzo[1,4]dioxin-6-yl)-amide | 0.83 | 426.08 |
| 206 | 2-(4-Methyl-piperazin-1-yl)-benzothiazole-5-carboxylic acid (2,3-dihydro-benzo[1,4]dioxin-6-yl)-amide | 0.60 | 411.00 |
| 207 | 2-Piperidin-1-yl-benzothiazole-5-carboxylic acid (2,3-dihydro-benzo[1,4]dioxin-6-yl)-amide | 0.85 | 396.06 |
| 208 | 2-(6-Oxa-1-aza-spiro[3.4]oct-1-yl)-benzothiazole-5-carboxylic acid (2,3-dihydro-benzo[1,4]dioxin-6-yl)-amide | 0.77 | 424.09 |
| 209 | 2-(6-Oxa-1-aza-spiro[3.3]hept-1-yl)-benzothiazole-5-carboxylic acid benzo[1,3]dioxol-5-ylamide | 0.79 | 396.00 |
| 210 | 2-(4-Methoxy-piperidin-1-yl)-benzothiazole-5-carboxylic acid benzo[1,3]dioxol-5-ylamide | 0.83 | 411.96 |
| 211 | 2-(4-Methyl-piperazin-1-yl)-benzothiazole-5-carboxylic acid benzo[1,3]dioxol-5-ylamide | 0.60 | 397.06 |

Example 197. $^1$H NMR (500 MHz, D$_6$-DMSO): δ 10.08 (s, 1H), 8.21 (d, J=1.6 Hz, 1H), 7.95 (d, J=8.2 Hz, 1H), 7.71-7.73 (m, 1H), 7.70 (dd, J$_1$=1.7 Hz, J$_2$=8.2 Hz, 1H), 7.46 (dd, J$_1$=2.2 Hz, J$_2$=8.5 Hz, 1H), 6.74 (d, J=8.5 Hz, 1H), 5.35 (d, J=7.8 Hz, 2H), 4.68 (d, J=7.9 Hz, 2H), 4.53 (t, J=8.7 Hz, 2H), 3.97 (t, J=7.1 Hz, 2H), 3.20 (m, J=8.7 Hz, 2H), 2.74 (t, J=7.2 Hz, 2H), 1.23-1.30 (m, 2H).

Example 198. $^1$H NMR (500 MHz, DMSO): δ 10.07 (s, 1H), 8.10 (d, J=1.6 Hz, 1H), 7.93 (d, J=8.3 Hz, 1H), 7.69-7.71 (m, 1H), 7.69 (d, J, =1.7 Hz, J$_2$=8.4 Hz, 1H), 7.44 (dd, J$_1$=2.2 Hz, J$_2$=8.5 Hz, 1H), 6.74 (d, J=8.5 Hz, 1H), 4.53 (t, J=8.7 Hz, 2H), 3.74-3.79 (m, 4H), 3.20 (t, J=8.7 Hz, 2H), 2.12-2.21 (m, 4H).

Example 207. $^1$H NMR (400 MHz, D$_6$-DMSO): δ 10.05 (s, 1H), 8.04 (d, J=1.5 Hz, 1H), 7.88 (d, J=8.2 Hz, 1H), 7.62 (dd, J$_1$=1.6 Hz, J$_2$=8.2 Hz, 1H), 7.43 (d, J=2.4 Hz, 1H), 7.25 (dd, J$_1$=2.4 Hz, J$_2$=8.8 Hz, 1H), 6.82 (d, J=8.8 Hz, 1H), 4.15-4.32 (m, 4H), 3.56-3.65 (m, 4H), 1.57-1.73 (m, 6H).

Example 211. $^1$H NMR (500 MHz, D$_6$-DMSO): δ 10.13 (s, 1H), 8.06 (d, J=1.6 Hz, 1H), 7.91 (d, J=8.2 Hz, 1H), 7.65 (dd, J$_1$=1.7 Hz, J$_2$=8.2 Hz, 1H), 7.48 (d, J=2.0 Hz, 1H), 7.24 (dd, J$_1$=2.1 Hz, J$_2$=8.4 Hz, 1H), 6.90 (d, J=8.4 Hz, 1H), 6.01 (s, 2H), 3.60 (m, 4H), 2.44-2.48 (m, 4H), 2.25 (s, 3H).

Biological Assays

The nucleotide sequence and the amino acid sequence for the human NOX4 (Entrez Gene ID 50507) is known in the art and are published. The potency and efficacy of the compounds of Formula (I) are assessed for their potential to inhibit the formation of ROS in a cellular assay.

Plasmid Production

The full-length human NOX4 (NM_016931.3) transcript was cloned into the pDONR™221 vector (Life Technologies™) in order to generate, by site-specific integration according to the recommendation of the manufacturer (Life Technologies™), a recombinant pJTI™ R4 DEST CMV-TO vector containing the NOX4 coding information controlled by tetracycline (tet) responsive tet-on cytomegalovirus promoter (hNOX4 pDEST).

Cell Culture and Transfection

Modified human embryonic kidney cells overexpressing a tet receptor (Jump-In™ T-REx™ HEK293; Life Technologies™) were transfected with the NOX4-containing tet-on vector (hNOX4 pDEST) to generate a stable recombinant cell pool (hNOX4 T-REx-293). hNOX4 T-REx-293 cells were cultured in DMEM containing 4.5 g/L glucose supplemented with 10% fetal calf serum, penicillin (100 U/mL), streptomycin (100 μg/mL), geneticin (1 mg/mL), and blasticidin (5 μg/mL) at 37° C. in air with 5% CO2. Human Nox4 expression was induced with tet (1 μg/mL) for 24 h and extracellular $H_2O_2$ was quantified using the Amplex Red reagent (Life Technologies™).

Amplex Red Activity Assay

Inhibitory activities on NOX4 have been measured for each example compound using the following procedure:

Compounds were prepared as 10 mM stock solution in DMSO vehicle, then diluted in 384-well plates using DMSO followed by a transfer of the dilutions into the assay plate. As a control, diphenylene iodonium was included at a final concentration of 10 μM. Compounds were tested at 10 concentrations in the range from 50 μM highest to 100 nM lowest.

Cellular $H_2O_2$ formation was measured using the Amplex Red reagent. Cells were washed with 1×PBS, trypsinized with 1×Trypsin-EDTA, collected by centrifugation and resuspended in 1×PBS. Cells were seeded into 384-well clear bottom plates at a density of 20 000 cells per well in presence or absence of compounds. The assay was started by the addition of Amplex Red and horseradish peroxidase at final concentrations of 25 μM and 0.1 U/mL, respectively. All wells contained 1.25% of DMSO. The plates were kept at 25° C. for 60 min. The amount of produced resorufin was detected with the Synergy™ Mx microplate reader (BioTek) with excitation and emission wavelengths set to 550 nm and 600 nm, respectively. Fluorescence was measured for each well and the fluorescence at 600 nm wavelength was compared to the fluorescence of the vehicle in place of compound. Inhibitory activities of example compounds were determined by calculating the $IC_{50}$ value (the concentration of compound needed to inhibit 50% of the enzyme activity). The calculated $IC_{50}$ values may fluctuate depending on the daily cellular assay performance. Fluctuations of this kind are known to those skilled in the art. In the case where $IC_{50}$ values have been determined several times for the same compound, the geometric mean is given. $IC_{50}$ values of exemplified compounds are displayed in the Table below.

Amplex Red Counter Screen Assay

In order to identify compounds that interfere with the activity assay either by inhibiting the activity of horseradish peroxidase or by directly interacting with the formed $H_2O_2$ a counter screen assay was established. This control assay is almost identical to the described Amplex Red activity assay with the only difference that the $H_2O_2$— generating cells are replaced by 1562.5 nM $H_2O_2$ in 1×PBS.

TABLE 1

| Compound of Example | $IC_{50}$ Amplex [nM] | $IC_{50}$ Control [μM] |
|---|---|---|
| 1 | 344 | >50 |
| 2 | 639 | >50 |
| 3 | 899 | >50 |
| 4 | 967 | >50 |
| 5 | 627 | >50 |
| 6 | 559 | >50 |
| 7 | 358 | >50 |
| 8 | 1890 | >50 |
| 9 | 573 | >50 |
| 10 | 711 | >50 |
| 11 | 358 | >50 |
| 12 | 688 | >50 |
| 13 | 5360 | >50 |
| 14 | 1700 | >50 |
| 15 | 405 | >50 |

TABLE 1-continued

| Compound of Example | $IC_{50}$ Amplex [nM] | $IC_{50}$ Control [μM] |
|---|---|---|
| 16 | 389 | >50 |
| 17 | 2300 | >50 |
| 18 | 568 | >50 |
| 19 | 2890 | >50 |
| 20 | 1400 | >50 |
| 21 | 1610 | >50 |
| 22 | 505 | >50 |
| 23 | 1470 | >50 |
| 24 | 352 | >50 |
| 25 | 804 | >50 |
| 26 | 1490 | >50 |
| 27 | 729 | >50 |
| 28 | 695 | >50 |
| 29 | 541 | >50 |
| 30 | 1230 | >50 |
| 31 | 2170 | >50 |
| 32 | 2410 | >50 |
| 33 | 2140 | >50 |
| 34 | 1220 | >50 |
| 35 | 379 | >50 |
| 36 | 404 | >50 |
| 37 | 841 | >50 |
| 38 | 1750 | >50 |
| 39 | 444 | >50 |
| 40 | 812 | >50 |
| 41 | 2520 | >50 |
| 42 | 566 | >50 |
| 43 | 541 | >50 |
| 44 | 1140 | >50 |
| 45 | 573 | >50 |
| 46 | 570 | >50 |
| 47 | 657 | >50 |
| 48 | 448 | >50 |
| 49 | 1230 | >50 |
| 50 | 451 | >50 |
| 51 | 4570 | >50 |
| 52 | 899 | >50 |
| 53 | 913 | >50 |
| 54 | 2910 | >50 |
| 55 | 400 | >50 |
| 56 | 906 | >50 |
| 57 | 681 | >50 |
| 58 | 1330 | >50 |
| 59 | 731 | >50 |
| 60 | 1670 | >50 |
| 61 | 5240 | >50 |
| 62 | 702 | >50 |
| 63 | 359 | >50 |
| 64 | 2130 | >50 |
| 65 | 851 | >50 |
| 66 | 4170 | >50 |
| 67 | 3080 | >50 |
| 68 | 1790 | >50 |
| 69 | 1930 | >50 |
| 70 | 889 | >50 |
| 71 | 336 | >50 |
| 72 | 524 | >50 |
| 73 | 4100 | >50 |
| 74 | 1080 | >50 |
| 75 | 421 | >50 |
| 76 | 414 | >50 |
| 77 | 548 | >50 |
| 78 | 417 | >50 |
| 79 | 585 | >50 |
| 80 | 312 | >50 |
| 81 | 2450 | >50 |
| 82 | 2350 | >50 |
| 83 | 3540 | >50 |
| 84 | 1320 | >50 |
| 85 | 1650 | >50 |
| 86 | 2680 | >50 |
| 87 | 4100 | >50 |
| 88 | 3660 | >50 |
| 89 | 1920 | >50 |
| 90 | 361 | >50 |
| 91 | 4331 | >50 |

TABLE 1-continued

| Compound of Example | IC$_{50}$ Amplex [nM] | IC$_{50}$ Control [μM] |
|---|---|---|
| 92 | 2460 | >50 |
| 93 | 10300 | >50 |
| 94 | 3290 | >50 |
| 95 | 2140 | >50 |
| 96 | 2670 | >50 |
| 97 | 6303 | >50 |
| 98 | 2530 | >50 |
| 99 | 3080 | >50 |
| 100 | 3390 | >50 |
| 101 | 2370 | >50 |
| 102 | 9170 | >50 |
| 103 | 3210 | >50 |
| 104 | 6870 | >50 |
| 105 | 14800 | >50 |
| 106 | 9390 | >50 |
| 107 | 9510 | >50 |
| 108 | 2540 | >50 |
| 109 | 1780 | >50 |
| 110 | 2030 | >50 |
| 111 | 1090 | >50 |
| 112 | 2270 | >50 |
| 113 | 3250 | >50 |
| 114 | 2940 | >50 |
| 115 | 3410 | >50 |
| 116 | 2170 | >50 |
| 117 | 3760 | >50 |
| 118 | 504 | >50 |
| 119 | 990 | >50 |
| 120 | 2340 | >50 |
| 121 | 9530 | >50 |
| 122 | 2110 | >50 |
| 123 | 434 | >50 |
| 124 | 414 | >50 |
| 125 | 772 | >50 |
| 126 | 757 | >50 |
| 127 | 1250 | >50 |
| 128 | 1740 | >50 |
| 129 | 857 | >50 |
| 130 | 991 | >50 |
| 131 | 1050 | >50 |
| 132 | 1080 | >50 |
| 133 | 614 | >50 |
| 134 | 870 | >50 |
| 135 | 1090 | >50 |
| 136 | 1280 | >50 |
| 137 | 1640 | >50 |
| 138 | 1480 | >50 |
| 139 | 1090 | >50 |
| 140 | 2520 | >50 |
| 141 | 10600 | >50 |
| 142 | 891 | >50 |
| 143 | 681 | >50 |
| 144 | 1540 | >50 |
| 145 | 1400 | >50 |
| 146 | 3180 | >50 |
| 147 | 379 | >50 |
| 148 | 1880 | >50 |
| 149 | 1430 | >50 |
| 150 | 2200 | >50 |
| 151 | 1410 | >50 |
| 152 | 1350 | >50 |
| 153 | 1300 | >50 |
| 154 | 1130 | >50 |
| 155 | 756 | >50 |
| 156 | 1790 | >50 |
| 157 | 2030 | >50 |
| 158 | 2860 | >50 |
| 159 | 1480 | >50 |
| 160 | 541 | >50 |
| 161 | 665 | >50 |
| 162 | 954 | >50 |
| 163 | 1140 | >50 |
| 164 | 1280 | >50 |
| 165 | 764 | >50 |
| 166 | 1500 | >50 |
| 167 | 1220 | >50 |
| 168 | 1140 | >50 |
| 169 | 793 | >50 |
| 170 | 899 | >50 |
| 171 | 792 | >50 |
| 172 | 8850 | >50 |
| 173 | 1420 | >50 |
| 174 | 1390 | >50 |
| 175 | 1350 | >50 |
| 176 | 2970 | >50 |
| 177 | 6870 | >50 |
| 178 | 21800 | >50 |
| 179 | 1740 | >50 |
| 180 | 1770 | >50 |
| 181 | 2440 | >50 |
| 182 | 3390 | >50 |
| 183 | 8700 | >50 |
| 184 | 1890 | >50 |
| 185 | 3860 | >50 |
| 186 | 3450 | >50 |
| 187 | 3390 | >50 |
| 188 | 3640 | >50 |
| 189 | 2190 | >50 |
| 190 | 3580 | >50 |
| 191 | 4380 | >50 |
| 192 | 4320 | >50 |
| 193 | 4040 | >50 |
| 194 | 3580 | >50 |
| 195 | 4440 | >50 |
| 196 | 2560 | >50 |
| 197 | 728 | >50 |
| 198 | 45200 | >50 |
| 199 | 23900 | >50 |
| 200 | 2750 | >50 |
| 201 | 2870 | >50 |
| 202 | 729 | >50 |
| 203 | 1840 | >50 |
| 204 | 25500 | >50 |
| 205 | 26800 | >50 |
| 206 | 21200 | >50 |
| 207 | 12800 | >50 |
| 208 | 2710 | >50 |
| 209 | 1500 | >50 |
| 210 | 6900 | >50 |
| 211 | 8900 | >50 |

The invention claimed is:

1. A compound of the Formula (I),

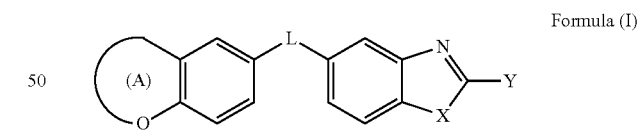

Formula (I)

wherein ring (A) represents a non-aromatic 5- to 7-membered heterocyclic ring which is fused to the phenyl group; wherein said 5- to 7-membered heterocyclic ring contains one oxygen ring atom and optionally one further ring heteroatom independently selected from oxygen or nitrogen;

wherein said 5- to 7-membered heterocyclic ring independently is unsubstituted, or mono-, or di-substituted, wherein the substituents are independently selected from:

one oxo substituent attached to a ring carbon atom in alpha position to a ring oxygen and/or a ring nitrogen atom; and/or one C$_{1-3}$-alkyl attached to a ring nitrogen atom having a free valency; or
two fluoro substituents attached to the same ring carbon atom;
L represents —NH—CO—* or —CO—NH—*, wherein the asterisks (*) indicate the bond that is linked to the benzothiazole moiety;
X represents S; and
Y represents
—NR$^1$R$^2$ wherein
R$^1$ represents
C$_{1-4}$-alkyl;
C$_{2-4}$-alkyl which is mono-substituted with di-(C$_{1-3}$-alkyl)amino, hydroxy or C$_{1-3}$-alkoxy;
C$_{3-5}$-cycloalkyl-L$^1$-, wherein L$^1$ represents a direct bond or C$_{1-3}$-alkylene; and wherein the C$_{3-5}$-cycloalkyl optionally contains one oxygen ring atom, and wherein said C$_{3-5}$-cycloalkyl is unsubstituted, or mono-substituted with methyl or fluoro; or
a piperidin-3-yl, piperidin-4-yl or pyrrolidin-3-yl group, which groups are substituted on the ring nitrogen atom with C$_{3-5}$-cycloalkyl, wherein said C$_{3-5}$-cycloalkyl optionally contains one oxygen ring atom; and
R$^2$ represents hydrogen, C$_{1-3}$-alkyl, or C$_{3-5}$-cycloalkyl;
or Y represents a saturated 4- to 7-membered monocyclic heterocyclyl selected from:
morpholin-4-yl; 2-oxo-pyrrolidin-1-yl; 1,1-dioxido-thiomorpholin-4-yl; or piperazin-1-yl optionally mono-substituted in position 4 with oxetan-3-yl or C$_{1-3}$-alkyl;
or azetidin-1-yl, pyrrolidin-1-yl, or piperidin-1-yl; wherein said azetidin-1-yl, pyrrolidin-1-yl, or piperidin-1-yl independently is unsubstituted, or substituted with:
two fluoro substituents attached to the same ring carbon atom; or
one substituent selected from unsubstituted phenyl, or unsubstituted 5- or 6-membered heteroaryl; or
one substituent selected from hydroxy; C$_{1-3}$-alkoxy; —CO—C$_{1-4}$-alkoxy; di-(C$_{1-3}$-alkyl)amino; and C$_{1-3}$-alkyl which is mono-substituted with di-(C$_{1-3}$-alkyl)amino, hydroxy, or C$_{1-3}$-alkoxy; or
two substituents, wherein one of said substituents is C$_{1-4}$-alkyl, and the other is independently selected from hydroxy, or di-(C$_{1-3}$-alkyl)amino; or
one substituent selected from morpholin-4-yl; 1,1-dioxidothiomorpholin-4-yl; or piperazin-1-yl which is optionally mono-substituted in position 4 with C$_{1-3}$-alkyl; or
one substituent selected from azetidin-1-yl, pyrrolidin-1-yl, or piperidin-1-yl; wherein said groups independently are unsubstituted, or mono-substituted with hydroxy, or di-substituted with methyl and hydroxy;
or Y represents saturated 7- to 11-membered fused, bridged, or spiro-bicyclic heterocyclyl containing at least one nitrogen atom, wherein said nitrogen atom is bound to the benzothiazole moiety, and wherein said heterocyclyl optionally contains one further ring heteroatom independently selected from oxygen, nitrogen and sulfur; wherein said heterocyclyl is unsubstituted, or substituted with:
two oxo substituents at a ring sulfur ring atom; or
one C$_{1-3}$-alkyl substituent attached to a ring nitrogen atom having a free valency;
or a pharmaceutically acceptable salt thereof.

2. A compound according to claim 1, wherein the fragment

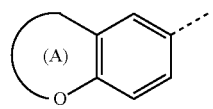

represents a group selected from:

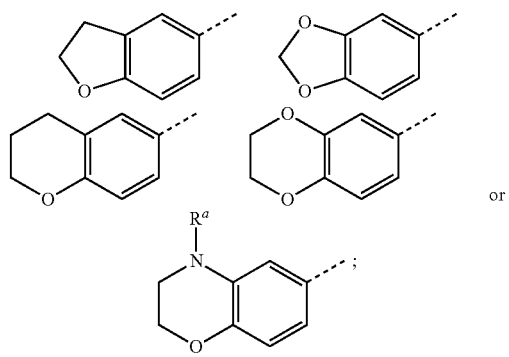

wherein R$^a$ represents hydrogen, or C$_{1-3}$-alkyl;
or a pharmaceutically acceptable salt thereof.

3. A compound according to claim 1, wherein the fragment

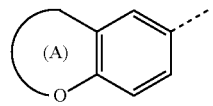

represents

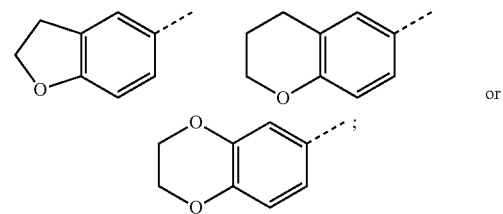

or a pharmaceutically acceptable salt thereof.

4. A compound according to claim 1; wherein L represents —CO—NH—*, wherein the asterisk (*) indicates the bond that is linked to the benzothiazole moiety; or a pharmaceutically acceptable salt thereof.

5. A compound according to claim 1; wherein X represents S; or a pharmaceutically acceptable salt thereof.

6. A compound according to claim 1; wherein
Y represents a group —NR$^1$R$^2$, wherein
R$^1$ represents
C$_{1-4}$-alkyl;
C$_{2-4}$-alkyl which is mono-substituted with di-(C$_{1-3}$-alkyl)amino;

$C_{3-5}$-cycloalkyl-$L^1$-, wherein $L^1$ represents a direct bond or $C_{1-3}$-alkylene; and wherein the $C_{3-5}$-cycloalkyl optionally contains one oxygen ring atom, and wherein said $C_{3-5}$-cycloalkyl is unsubstituted, or mono-substituted with methyl or fluoro; or 1-(oxetan-3-yl)-piperidin-4-yl; and $R^2$ represents hydrogen, $C_{1-3}$-alkyl, or $C_{3-5}$-cycloalkyl; or Y represents a group

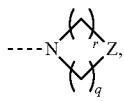

wherein r and q both represent the integer 2; and

Z represents O, $SO_2$, or $NR^{Y1}$, wherein $R^{Y1}$ represents oxetan-3-yl or $C_{1-3}$-alkyl;

or r represents the integer 0, 1, 2, or 3; q represents the integer 1, 2, 3, or 4; and the sum of r and q is 2, 3, or 4;

Z represents $CH_2$, $CHR^{Y2}$, or $CR^{Y3}R^{Y4}$;

wherein $R^{Y2}$ represents unsubstituted phenyl, or unsubstituted 5- or 6-membered heteroaryl;

hydroxy; $C_{1-3}$-alkoxy; —CO—$C_{1-4}$-alkoxy; di-($C_{1-3}$-alkyl)amino; or $C_{1-3}$-alkyl which is mono-substituted with di-($C_{1-3}$-alkyl)amino, hydroxy, or $C_{1-3}$-alkoxy;

morpholin-4-yl; 1,1-dioxidothiomorpholin-4-yl; or piperazin-1-yl which is optionally mono-substituted in position 4 with $C_{1-3}$-alkyl; or azetidin-1-yl, pyrrolidin-1-yl, or piperidin-1-yl; wherein said groups independently are unsubstituted, or mono-substituted with hydroxy, or di-substituted with methyl and hydroxy;

and $R^{Y3}$ represents $C_{1-4}$-alkyl; and $R^{Y4}$ independently represents hydroxy, or di-($C_{1-3}$-alkyl)amino;

or $R^{Y3}$ and $R^{Y4}$ both represent fluoro;

or $R^{Y3}$ and $R^{Y4}$ together with the carbon atom to which they are attached to form a 4- to 6-membered saturated carbocyclic ring; or a 4- to 6-membered saturated heterocyclic ring, wherein said heterocyclic ring contains one ring heteroatom independently selected from oxygen, nitrogen and sulfur; and wherein said heterocyclic ring is unsubstituted, or substituted with:

two oxo substituents at a ring sulfur ring atom; or one $C_{1-3}$-alkyl substituent attached to a ring nitrogen atom having a free valency;

or a pharmaceutically acceptable salt thereof.

7. A compound according to claim 1; wherein Y represents

N—($C_{1-3}$-alkyl)amino, N,N-di-($C_{1-3}$-alkyl)-amino, N-[2-(di-$C_{1-3}$-alkyl)amino)-ethyl]-N—($C_{1-3}$-alkyl)-amino, N—($C_{1-4}$-alkyl)-N-(oxetan-3-yl)-amino, N—($C_{3-5}$-cycloalkyl)-N-(oxetan-3-yl)-amino, N—($C_{1-4}$-alkyl)-N-(oxetan-3-yl-methyl)-amino, N-(3-methyl-oxetan-3-yl)-N-methylamino, N-(3-fluoro-oxetan-3-yl-methyl)-N-methylamino, or N-methyl-((N-(oxetan-3-yl)-piperidin)-4-yl)-amino;

or Y represents a saturated 4- to 7-membered monocyclic heterocyclyl selected from:

morpholin-4-yl; 2-oxo-pyrrolidin-1-yl; 1,1-dioxidothiomorpholin-4-yl; or piperazin-1-yl optionally mono-substituted in position 4 with oxetan-3-yl or $C_{1-3}$-alkyl;

or azetidin-1-yl which is unsubstituted, or substituted with:

two fluoro substituents attached to the same ring carbon atom; or one phenyl or pyridinyl substituent, wherein said phenyl or pyridinyl is unsubstituted; or one substituent selected from hydroxy; $C_{1-3}$-alkoxy; —CO—$C_{1-4}$-alkoxy; di-($C_{1-3}$-alkyl)amino; and $C_{1-3}$-alkyl which is mono-substituted with di-($C_{1-3}$-alkyl)amino, hydroxy, or $C_{1-3}$-alkoxy; or two substituents, wherein one of said substituents is $C_{1-4}$-alkyl, and the other is independently selected from hydroxy, or di-($C_{1-3}$-alkyl)amino; or one substituent selected from morpholin-4-yl; 1,1-dioxidothiomorpholin-4-yl;

one substituent selected from azetidin-1-yl, pyrrolidin-1-yl, or piperidin-1-yl; wherein said groups independently are unsubstituted, or mono-substituted with hydroxy, or di-substituted with methyl and hydroxy;

or pyrrolidin-1-yl, or piperidin-1-yl; wherein said pyrrolidin-1-yl, or piperidin-1-yl independently is unsubstituted, or substituted with:

two fluoro substituents attached to the same ring carbon atom; or one substituent selected from hydroxy; $C_{1-3}$-alkoxy; or di-($C_{1-3}$-alkyl)amino;

or Y represents saturated 7- to 11-membered spirobicyclic heterocyclyl containing at least one nitrogen atom, wherein said nitrogen atom is bound to the benzothiazole moiety, and wherein said heterocyclyl optionally contains one further ring heteroatom independently selected from oxygen, nitrogen and sulfur; wherein said heterocyclyl is unsubstituted, or substituted with:

two oxo substituents at a ring sulfur ring atom; or one $C_{1-3}$-alkyl substituent attached to a ring nitrogen atom having a free valency;

or a pharmaceutically acceptable salt thereof.

8. A compound according to claim 1; wherein Y represents a group independently selected from the following groups A), B), C), or D):

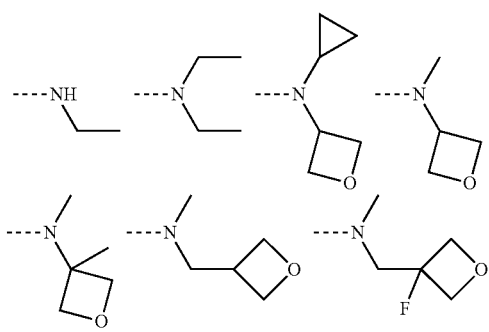

A)

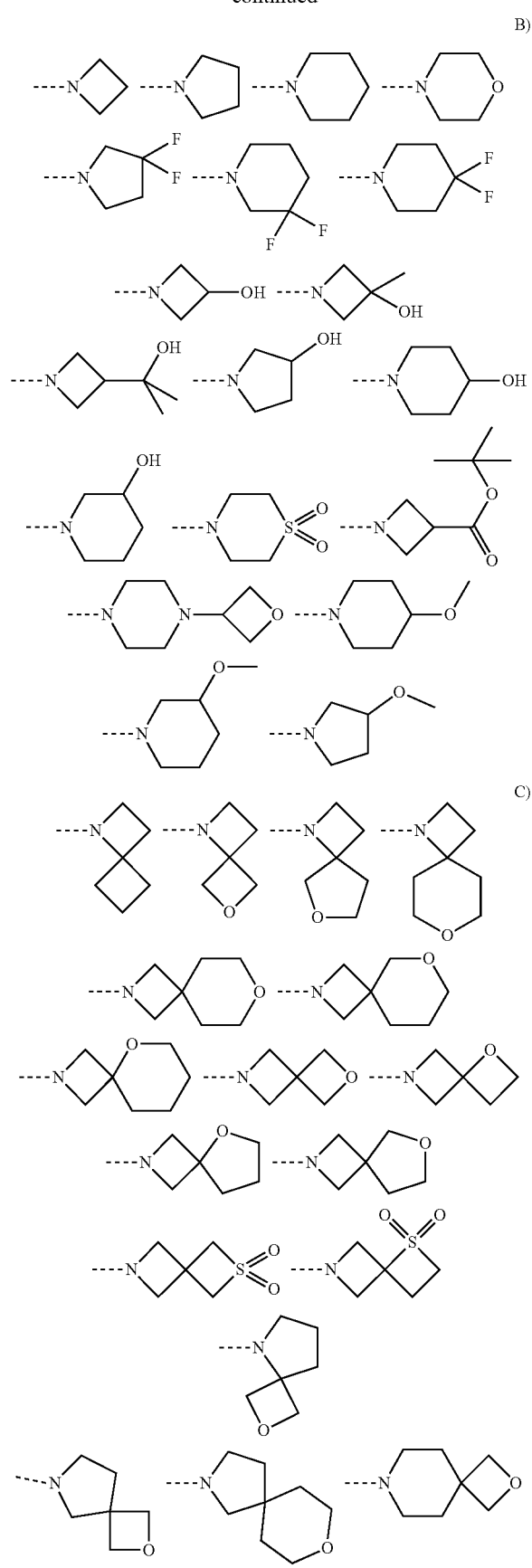
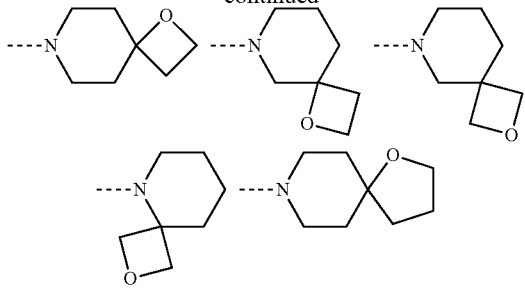
or a pharmaceutically acceptable salt thereof.
9. A compound according to claim 1; wherein Y represents a group independently selected from the following groups A) or B):
A)
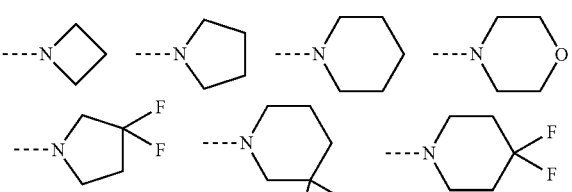
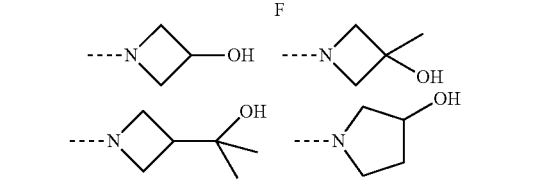
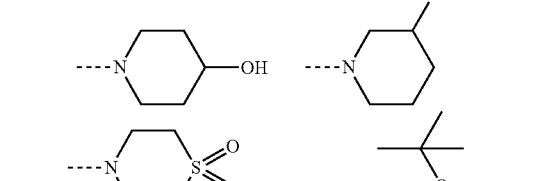
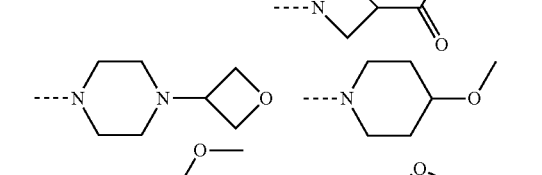
B)
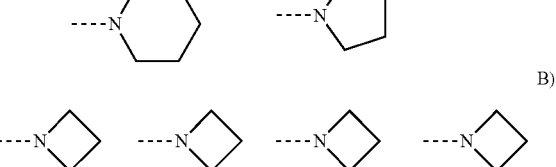

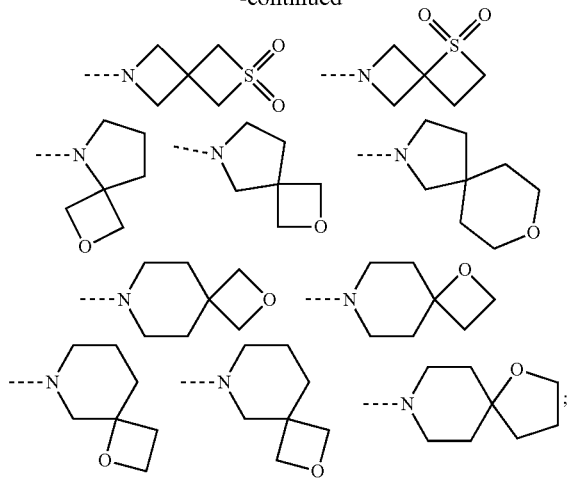

or a pharmaceutically acceptable salt thereof.

10. A compound according to claim 1, which is selected from the group consisting of:
- 2,3-Dihydro-benzofuran-5-carboxylic acid (2-piperidin-1-yl-benzothiazol-5-yl)-amide;
- 2,3-Dihydro-benzofuran-5-carboxylic acid (2-morpholin-4-yl-benzothiazol-5-yl)-amide;
- 2,3-Dihydro-benzofuran-5-carboxylic acid [2-(4-methyl-piperazin-1-yl)-benzothiazol-5-yl]-amide;
- 2,3-Dihydro-benzofuran-5-carboxylic acid (2-pyrrolidin-1-yl-benzothiazol-5-yl)-amide;
- 2,3-Dihydro-benzofuran-5-carboxylic acid (2-diethylamino-benzothiazol-5-yl)-amide;
- 2,3-Dihydro-benzofuran-5-carboxylic acid (2-dimethylamino-benzothiazol-5-yl)-amide;
- 2,3-Dihydro-benzofuran-5-carboxylic acid [2-(3,3-difluoro-azetidin-1-yl)-benzothiazol-5-yl]-amide;
- 2,3-Dihydro-benzofuran-5-carboxylic acid [2-(3,3-difluoro-pyrrolidin-1-yl)-benzothiazol-5-yl]-amide;
- 2,3-Dihydro-benzofuran-5-carboxylic acid [2-(3,3-difluoro-piperidin-1-yl)-benzothiazol-5-yl]-amide;
- 2,3-Dihydro-benzofuran-5-carboxylic acid [2-(6-oxa-1-aza-spiro[3.3]hept-1-yl)-benzothiazol-5-yl]-amide;
- 2,3-Dihydro-benzofuran-5-carboxylic acid [2-(2-oxa-6-aza-spiro[3.3]hept-6-yl)-benzothiazol-5-yl]-amide;
- 2,3-Dihydro-benzofuran-5-carboxylic acid [2-(1,1-dioxo-1l6-thiomorpholin-4-yl)-benzothiazol-5-yl]-amide;
- 2,3-Dihydro-benzofuran-5-carboxylic acid [2-(3-methoxy-pyrrolidin-1-yl)-benzothiazol-5-yl]-amide;
- 2,3-Dihydro-benzofuran-5-carboxylic acid [2-(4-methoxy-piperidin-1-yl)-benzothiazol-5-yl]-amide;
- 2,3-Dihydro-benzofuran-5-carboxylic acid [2-(3-hydroxy-3-methyl-azetidin-1-yl)-benzothiazol-5-yl]-amide;
- (S)—N-(2-(3-hydroxypyrrolidin-1-yl)benzo[d]thiazol-5-yl)-2,3-dihydrobenzofuran-5-carboxamide;
- 2,3-Dihydro-benzofuran-5-carboxylic acid [2-(2-oxa-7-aza-spiro[3.5]non-7-yl)-benzothiazol-5-yl]-amide;
- 2,3-Dihydro-benzofuran-5-carboxylic acid {2-[methyl-(1-oxetan-3-yl-piperidin-4-yl)-amino]-benzothiazol-5-yl}-amide;
- 2,3-Dihydro-benzofuran-5-carboxylic acid [2-(2-oxa-6-aza-spiro[3.5]non-6-yl)-benzothiazol-5-yl]-amide;
- 2,3-Dihydro-benzofuran-5-carboxylic acid [2-(methyl-oxetan-3-yl-amino)-benzothiazol-5-yl]-amide;
- 2,3-Dihydro-benzofuran-5-carboxylic acid [2-(3-methoxy-piperidin-1-yl)-benzothiazol-5-yl]-amide;
- 2,3-Dihydro-benzofuran-5-carboxylic acid [2-(3-hydroxy-azetidin-1-yl)-benzothiazol-5-yl]-amide;
- 2,3-Dihydro-benzofuran-5-carboxylic acid [2-(4-hydroxy-piperidin-1-yl)-benzothiazol-5-yl]-amide;
- 2,3-Dihydro-benzofuran-5-carboxylic acid [2-(2-phenyl-azetidin-1-yl)-benzothiazol-5-yl]-amide;
- 2,3-Dihydro-benzofuran-5-carboxylic acid [2-((R)-3-hydroxy-pyrrolidin-1-yl)-benzothiazol-5-yl]-amide;
- 2,3-Dihydro-benzofuran-5-carboxylic acid [2-(2-methoxymethyl-pyrrolidin-1-yl)-benzothiazol-5-yl]-amide;
- 2,3-Dihydro-benzofuran-5-carboxylic acid [2-((S)-3-hydroxy-piperidin-1-yl)-benzothiazol-5-yl]-amide;
- 2,3-Dihydro-benzofuran-5-carboxylic acid [2-(2-oxa-6-aza-spiro[3.4]oct-6-yl)-benzothiazol-5-yl]-amide;
- 2,3-Dihydro-benzofuran-5-carboxylic acid [2-((R)-3-hydroxy-piperidin-1-yl)-benzothiazol-5-yl]-amide;
- 2,3-Dihydro-benzofuran-5-carboxylic acid [2-(2-dimethylaminomethyl-pyrrolidin-1-yl)-benzothiazol-5-yl]-amide;
- 2-Piperidin-1-yl-benzothiazole-5-carboxylic acid (2,3-dihydro-benzofuran-5-yl)-amide;
- 2-(6-Oxa-1-aza-spiro[3.3]hept-1-yl)-benzothiazole-5-carboxylic acid (2,3-dihydro-benzofuran-5-yl)-amide;
- 2-(4-Methoxy-piperidin-1-yl)-benzothiazole-5-carboxylic acid (2,3-dihydro-benzofuran-5-yl)-amide;
- 2-(4-Methyl-piperazin-1-yl)-benzothiazole-5-carboxylic acid (2,3-dihydro-benzofuran-5-yl)-amide;
- 2-(6-Oxa-1-aza-spiro[3.4]oct-1-yl)-benzothiazole-5-carboxylic acid (2,3-dihydro-benzofuran-5-yl)-amide;
- 2-(6-Oxa-1-aza-spiro[3.3]hept-1-yl)-benzothiazole-5-carboxylic acid (2,3-dihydro-benzo[1,4]dioxin-6-yl)-amide;
- 2-(6-Oxa-1-aza-spiro[3.4]oct-1-yl)-benzothiazole-5-carboxylic acid (2,3-dihydro-benzo[1,4]dioxin-6-yl)-amide; and
- 2-(6-Oxa-1-aza-spiro[3.3]hept-1-yl)-benzothiazole-5-carboxylic acid benzo[1,3]dioxol-5-ylamide;

or a pharmaceutically acceptable salt thereof.

11. A pharmaceutical composition comprising, as active principle, one or more compounds according to claim 1, or a pharmaceutically acceptable salt thereof, and at least one therapeutically inert excipient.

12. A method of inhibition of myofibroblast differentiation in a patient in need thereof, comprising administering to said patient in need thereof an effective amount of the compound of claim 1, in free or pharmaceutically acceptable salt form.

13. The method according to claim 12, wherein the patient is suffering from a disease or disorder selected from a fibrotic disease; pulmonary hypertension; hypertension; asthma; acute respiratory distress syndrome; myocardial infarction; acute heart failure; cardiac and skeletal myopathy; stroke; traumatic brain injury; neuropathic pain; ataxia telangiectasia; ocular diseases; and cancer.

14. The method according to claim 13, wherein said fibrotic disease is pulmonary fibrosis; scleroderma; pancreatic fibrosis; liver fibrosis; chronic kidney disease; or cardiomyopathy.

15. The method according to claim 13, wherein the disease or disorder is Barth syndrome.

* * * * *